US012589123B2

(12) United States Patent
Lee et al.

(10) Patent No.: US 12,589,123 B2
(45) Date of Patent: Mar. 31, 2026

(54) COMPOSITIONS AND METHODS COMPRISING CLOSTRIDIUM BUTYRICUM FOR THE TREATMENT OF CANCER

(71) Applicant: City of Hope, Duarte, CA (US)

(72) Inventors: Peter P. Lee, San Marino, CA (US); Sumanta Kumar Pal, Brea, CA (US)

(73) Assignee: City of Hope, Duarte, CA (US)

( * ) Notice: Subject to any disclaimer, the term of this patent is extended or adjusted under 35 U.S.C. 154(b) by 644 days.

(21) Appl. No.: 17/996,779

(22) PCT Filed: Apr. 20, 2021

(86) PCT No.: PCT/US2021/028251
§ 371 (c)(1),
(2) Date: Oct. 20, 2022

(87) PCT Pub. No.: WO2021/216618
PCT Pub. Date: Oct. 28, 2021

(65) Prior Publication Data

US 2023/0149479 A1 May 18, 2023

Related U.S. Application Data

(60) Provisional application No. 63/013,141, filed on Apr. 21, 2020.

(51) Int. Cl.

| | |
|---|---|
| ***A61K 35/742*** | (2015.01) |
| ***A61K 45/06*** | (2006.01) |
| ***A61P 35/00*** | (2006.01) |

(52) U.S. Cl.
CPC ............ *A61K 35/742* (2013.01); *A61K 45/06* (2013.01); *A61P 35/00* (2018.01); *A61K 2300/00* (2013.01)

(58) Field of Classification Search
None
See application file for complete search history.

(56) References Cited

FOREIGN PATENT DOCUMENTS

| | | | |
|---|---|---|---|
| CN | 109 771 445 | A | 5/2019 |
| JP | S6153219 | A | 3/1986 |
| JP | 2009-269836 | A | 11/2009 |
| WO | WO-2018064165 | A2 | 4/2018 |
| WO | WO-2018115519 | A1 | 6/2018 |
| WO | WO-2019165285 | A1 | 8/2019 |
| WO | WO-2019178542 | A1 | 9/2019 |

OTHER PUBLICATIONS

Eso et al (J Gastroenterol 55:15-26, 2020).*
International Search Report and Written Opinion of PCT/US2021/28251, mailed Jul. 28, 2021.
Kamatham et al., Circulating Tumor DNA-Based Detection of Microsatelite Instability and Response to Immunotherapy in Pancreatic Cancer, Frontiers in Pharmacology, vol. 11, Art. 23, Feb. 10, 2020, p. 1-6.
Tomita et al., Association of Probiotic Clostridium butyricum Therapy with Survival and Response to Immune Checkpoint Blockade in Patients with Lung Cancer, Cancer Immunology Research, vol. 8, No. 10, Oct. 2020, published online Jul. 14, 2020, p. 1236-1242.
Bergerot, P.G. et al. (2020). A phase I trial to assess the biologic effect of CBM588 (*Clostridium butyricum*) in combination with nivolumab plus ipilimumab (nivo/ipi) in patients with metastatic renal cell carcinoma (mRCC). Database Accession No. EMB-631170140, Journal of Clinical Oncology 2020 American Society of Clinical Oncology vol. 38, No. 6, Supplement, 2020, ISSN: 1527-7755.
Choueiri, T.K. et al. (Jan. 26, 2017). "Systemic Therapy for Metastatic Renal-Cell Carcinoma," *N Engl J Med* 376(4):354-366.
Derosa, L. et al. (Jun. 1, 2018). "Negative association of antibiotics on clinical activity of immune checkpoint inhibitors in patients with advanced renal cell and non-small-cell lung cancer," *Ann Oncol* 29(6):1437-1444.
Extended European Search Report mailed on Apr. 17, 2024, for EP Patent Application No. 21793748.1, 14 pages.
Gopalakrishnan, V. et al. (Jan. 5, 2018, e-published Nov. 2, 2017). "Gut microbiome modulates response to anti-PD-1 immunotherapy in melanoma patients," *Science* 359(6371):97-103.
Isa, K. et al. (Aug. 2016, e-published Oct. 5, 2015). "Safety assessment of the Clostridium butyricum MIYAIRI 588® probiotic strain including evaluation of antimicrobial sensitivity and presence of Clostridium toxin genes in vitro and teratogenicity in vivo," *Hum Exp Toxicol* 35(8):818-832.
Motzer, R.J. et al. (Apr. 5, 2018). "Nivolumab plus Ipilimumab versus Sunitinib in Advanced Renal-Cell Carcinoma," *N Engl J Med* 378(14):1277-1290.
Seki, H. et al. (Feb. 2003). "Prevention of antibiotic-associated diarrhea in children by Clostridium butyricum MIYAIRI," *Pediatr Int* 45:86-90.
Sivan, A. et al. (Nov. 27, 2015, e-published Nov. 5, 2015). "Commensal Bifidobacterium promotes antitumor immunity and facilitates anti-PD-L1 efficacy," *Science* 350(6264):1084-1089.
Vetizou, M. et al. (Nov. 27, 2015, e-published Nov. 5, 2015). "Anticancer immunotherapy by CTLA-4 blockade relies on the gut microbiota," *Science* 350(6264):1079-1084.
Xin, M. et al. (Nov. 2019). "Synergistic anti-tumour effects of Clostridium butyricum in combination with apatinib in CT26 colorectal tumour-bearing mice," *Anti-Cancer Drugs* 30(10):991-997.

* cited by examiner

*Primary Examiner* — Brian J Gangle
(74) *Attorney, Agent, or Firm* — Kilpatrick Townsend and Stockton LLP

(57) ABSTRACT

Provided herein, inter alia, are methods and compositions for the treatment of cancer. The compositions include one or more anti-cancer agents and *Clostridium butyricum*. Administration of *Clostridium butyricum* can enhance the therapeutic effects of anti-cancer agents, thereby increasing the efficacy of said agents for cancer treatment.

15 Claims, 28 Drawing Sheets

Specification includes a Sequence Listing.

COMPOSITIONS AND METHODS COMPRISING CLOSTRIDIUM BUTYRICUM FOR THE TREATMENT OF CANCER

CROSS-REFERENCES TO RELATED APPLICATIONS

This application is a national stage entry, filed under 35 U.S.C. § 371, of International Application No. PCT/US2021/028251, filed Apr. 20, 2021, which claims the benefit of U.S. Provisional Application No. 63/013,141, filed Apr. 21, 2020, the contents of which are incorporated herein by reference in their entirety and for all purposes.

REFERENCE TO A "SEQUENCE LISTING," A TABLE, OR A COMPUTER PROGRAM LISTING APPENDIX SUBMITTED AS AN ASCII FILE

The Sequence Listing written in file 048440-758N01US SL.XML, created Oct. 17, 2022, 6,000 bytes, machine format IBM-PC, MS Windows operating system, is hereby incorporated by reference.

BACKGROUND OF THE INVENTION

More than 65,000 patients will be diagnosed with renal cell carcinoma in 2018 in the United States.[1] At the time of initial presentation, one-third of the cases are metastatic, and the remainder have varying rates of progression to metastatic disease. The current treatment algorithm includes surgery followed by a sequence of FDA-approved agents. In the last decade, multiple agents have been approved for treatment of metastatic renal cell carcinoma (mRCC) including targeted therapies (sunitinib, sorafenib, axitinib, pazopanib, everolimus, axitinib, cabozantinib) or immunotherapy with either nivolumab monotherapy or the combination of nivolumab and ipilimumab.[2] Nivolumab and ipilimumab are fully human monoclonal antibodies targeting the programmed cell death protein 1 (PD-1) and the cytotoxic T lymphocyte antigen 4 (CTLA-4) pathway respectively. Inhibition of the PD-1 and CTLA-4 immune checkpoint pathways overcomes the immune escape mechanisms of the tumor cells and allow for enhanced antitumor activity.

In the CheckMate214 trial,[3] the combination of nivolumab and ipilimumab was compared with sunitinib, which was considered the standard of care treatment for patients with mRCC.[4] Overall survival and objective response rate were significantly improved with the immunotherapy combination versus sunitinib (18-month overall survival 75% vs 60%, objective response rate 42% vs 27%, respectively). While these response rates are impressive, it is important to note that they reflect the minority of patients with mRCC. Furthermore, approximately 20% of patients who receive the nivolumab/ipilimumab combination in the front-line setting will develop progressive disease. Thus, there are currently significant efforts to build on this regimen and identify novel approaches to improve on the clinical efficacy of the nivolumab/ipilimumab combination.[3] Provided herein are, inter alia, solutions to these and other problems in the art.

BRIEF SUMMARY OF THE INVENTION

In an aspect is provided a method for treating cancer in a subject in need thereof, the method including administering to the subject a therapeutically effective amount of an anti-cancer agent and *Clostridium butyricum.*

In an aspect is provided a method for treating cancer in a subject in need thereof, the method including administering to the subject an effective amount of an anti-cancer agent and *Clostridium butyricum* MIYAIRI 588 live biotherapeutic product (CBM588 LBP).

In another aspect a pharmaceutical composition including an anti-cancer agent in a first dosage form and *Clostridium butyricum* in a second dosage form is provided.

In another aspect is provided a pharmaceutical composition including an anti-cancer agent and *Clostridium butyricum* MIYAIRI 588 (CBM588 LBP).

In another aspect is provided a kit including: (a) a first pharmaceutical composition including an anticancer agent in a first dosage form and a pharmaceutically acceptable excipient in a suitable container or with suitable packaging; and (b) a second pharmaceutical composition including *Clostridium butyricum* in a second dosage form in a suitable container or with suitable packaging.

In an aspect is provided a kit including: (a) a first pharmaceutical composition including an anti-cancer agent in a first dosage form and a pharmaceutically acceptable excipient in a suitable container or with suitable packaging; and (b) a second pharmaceutical composition including a *Clostridium butyricum* MIYAIRI 588 (CBM588 LBP) preparation in a second dosage form in a suitable container or with suitable packaging.

FIGS. 10A-10F are graphs showing relative abundance of Butyricimonas *faecalis* (FIG. 10A), *Finegoldia magna* (FIG. 10B), *Clostridioides difficile* (FIG. 10C), *Ruminococcus albus* (FIG. 10D), *Treponema* sp. RCC2812 (FIG. 10E), and *Thermoanaerobacter kivui* (FIG. 10F) in patients who were responsive (Rs) to CBM588 treatment as compared to patients who were non-responsive (NRs) to CBM588 at Time 1 and Time 2 treatment.

Figure 11A:
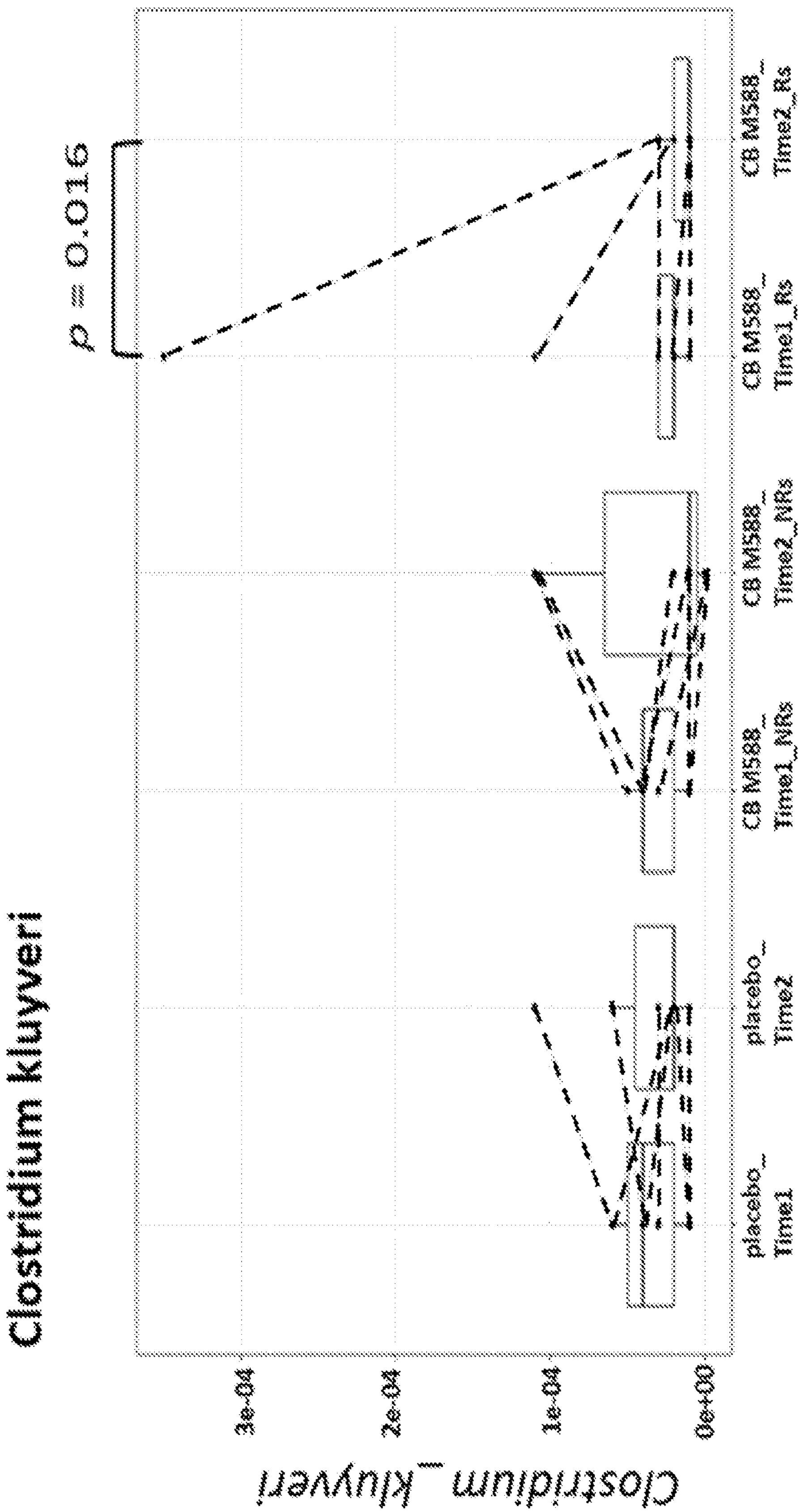
Figure 11B:
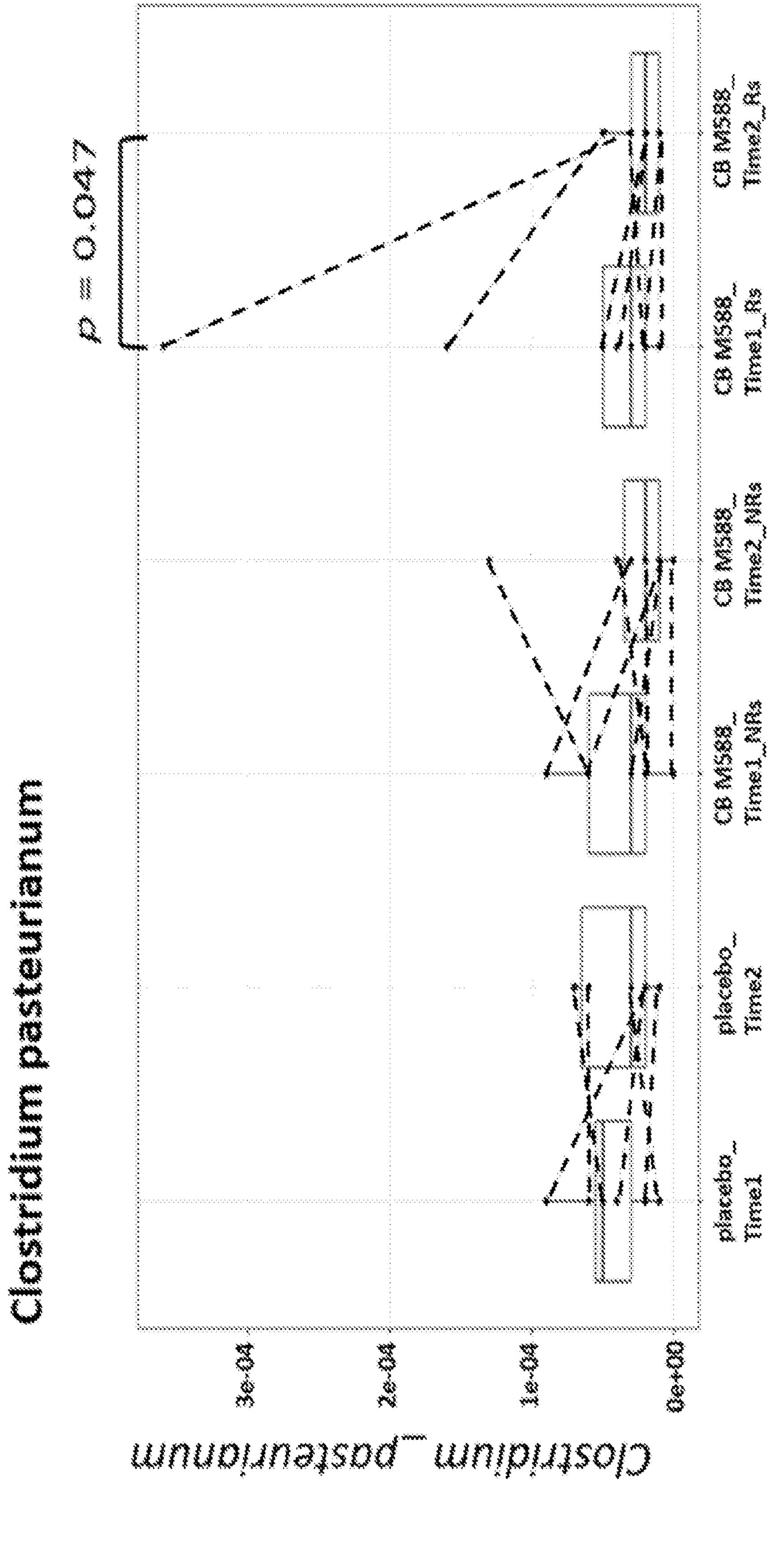
Figure 11C:
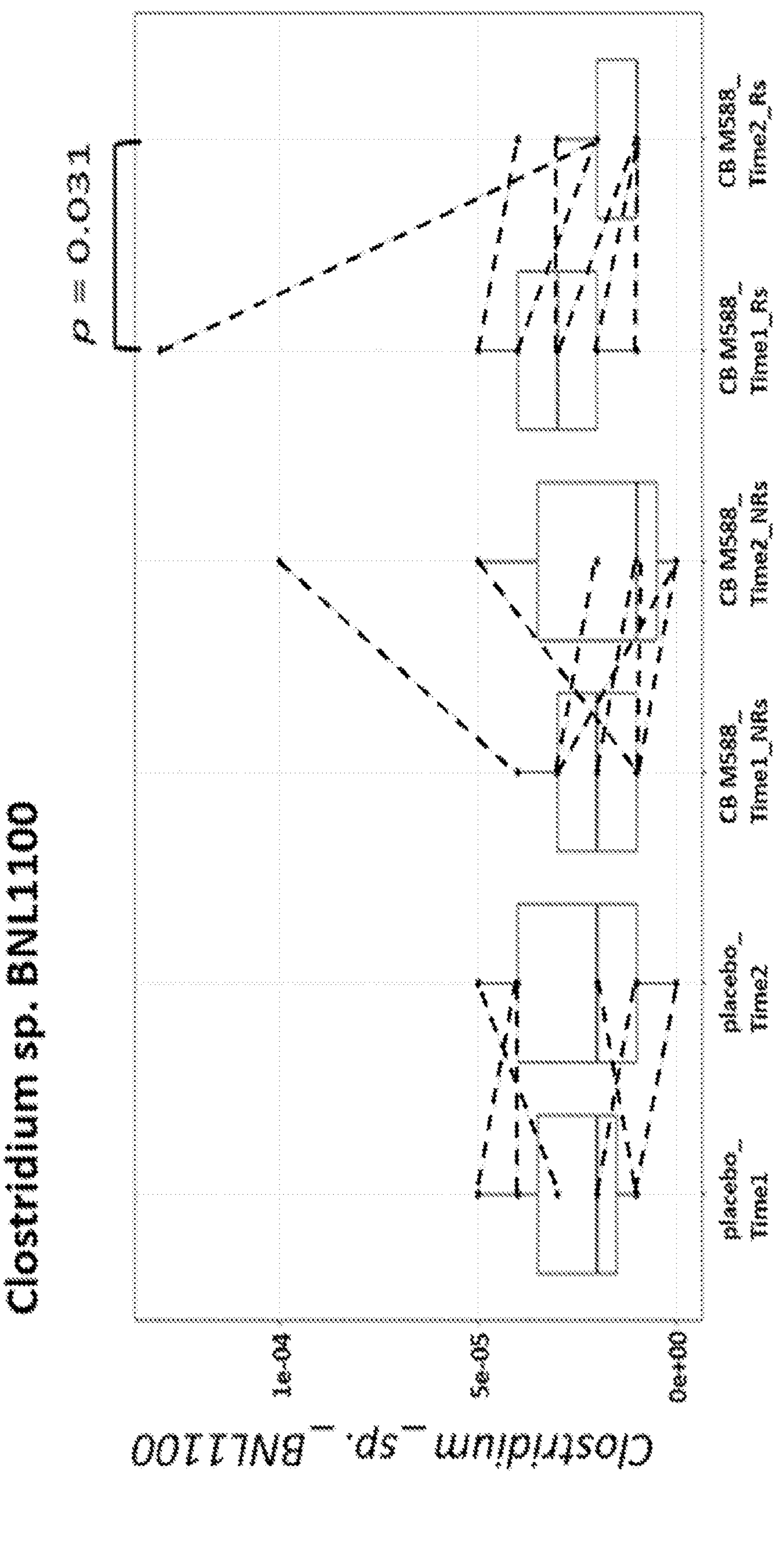

FIGS. 11A-11C are graphs illustrating comparative analysis of relative abundance of species of the family Clostridiaceae including *Clostridium kluyveri* (FIG. 11A), *Clostridium pasteurianum* (FIG. 11B), and *Clostridium* sp. BNL1100 (FIG. 11C) in patients who were responsive (Rs) to CBM588 treatment as compared to patients who were non-responsive (NRs) to CBM588 treatment at Time 1 and Time 2.

Figure 12A:
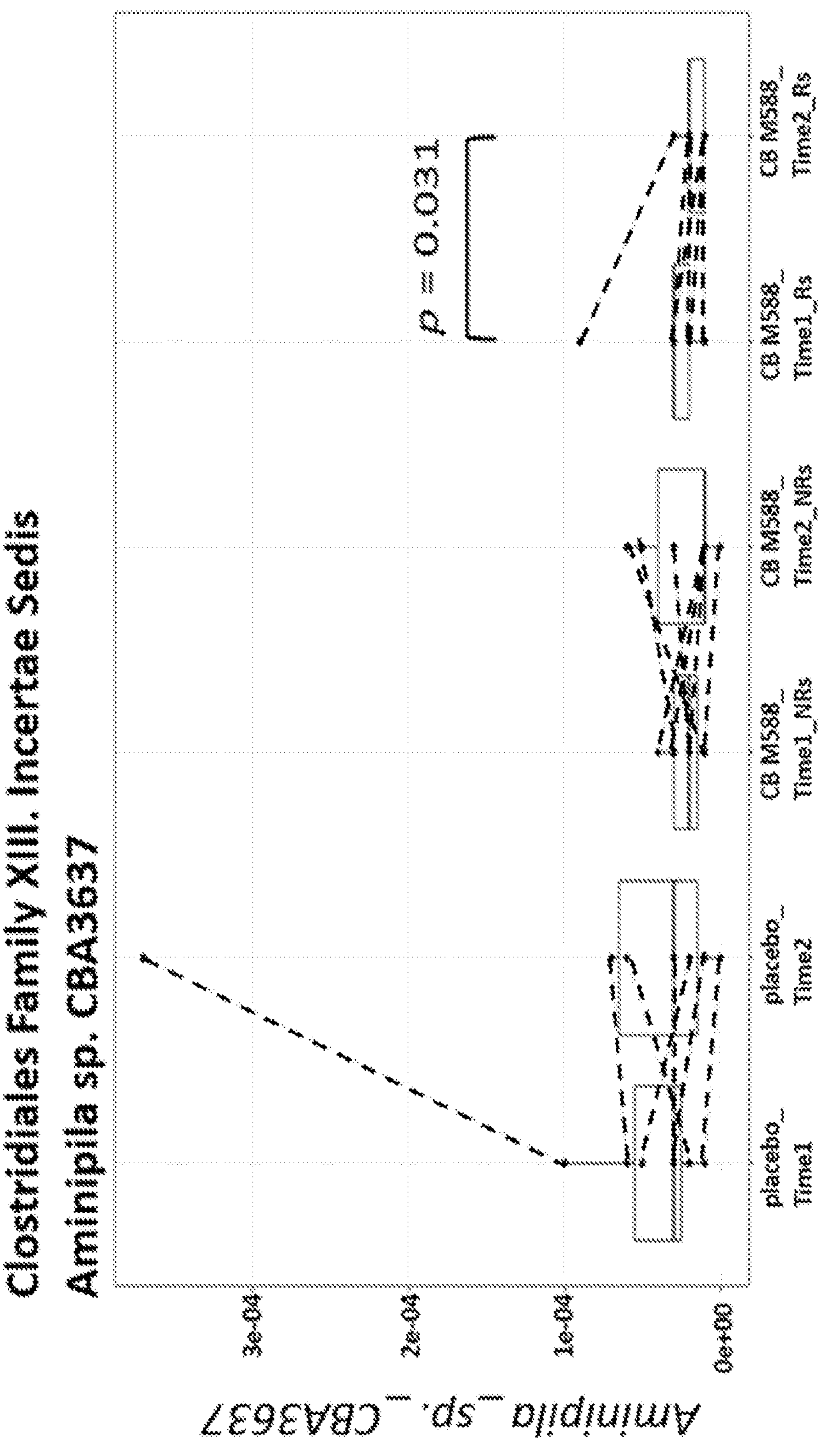
Figure 12B:
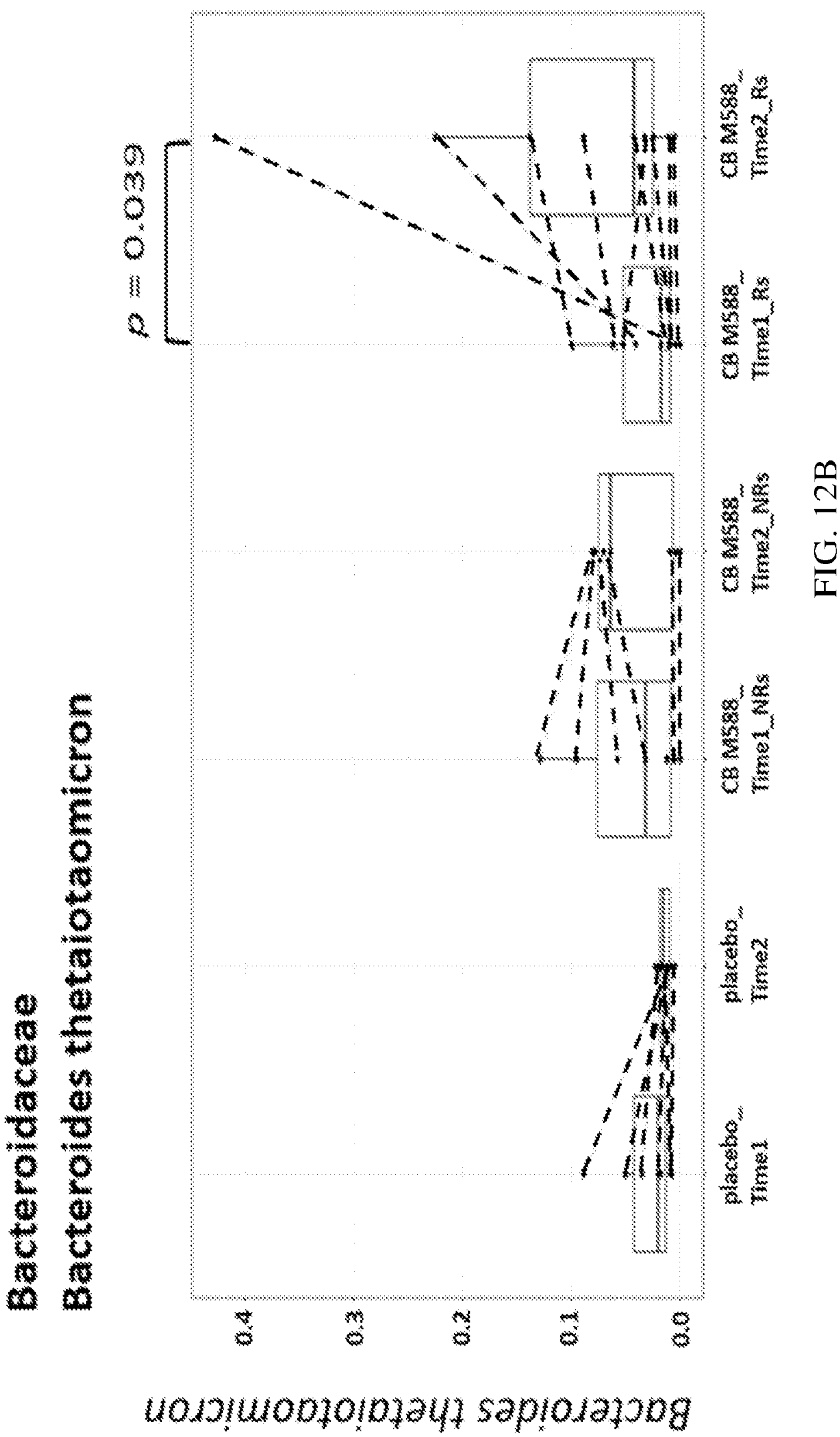
Figure 12C:
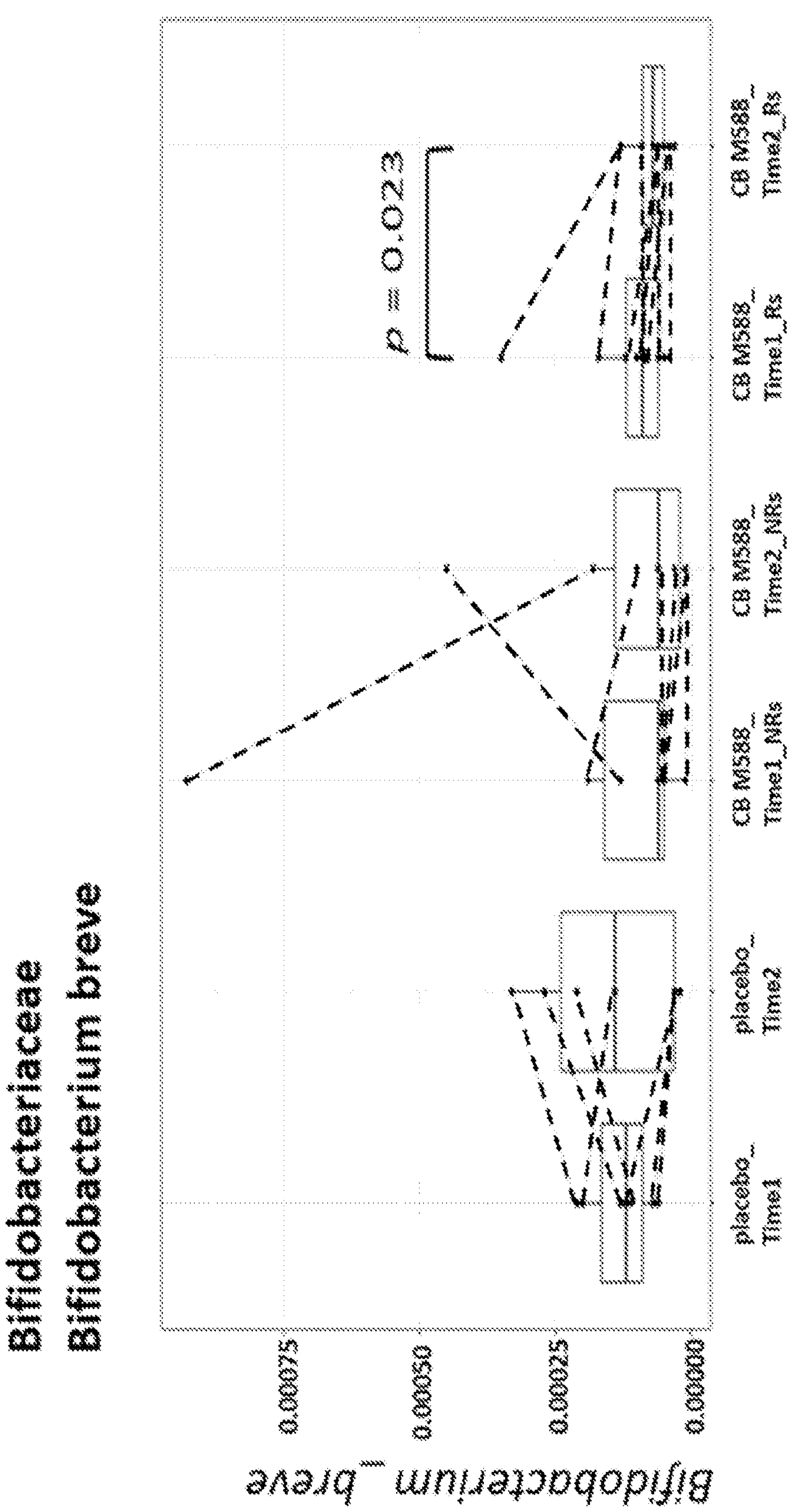
Figure 13A:
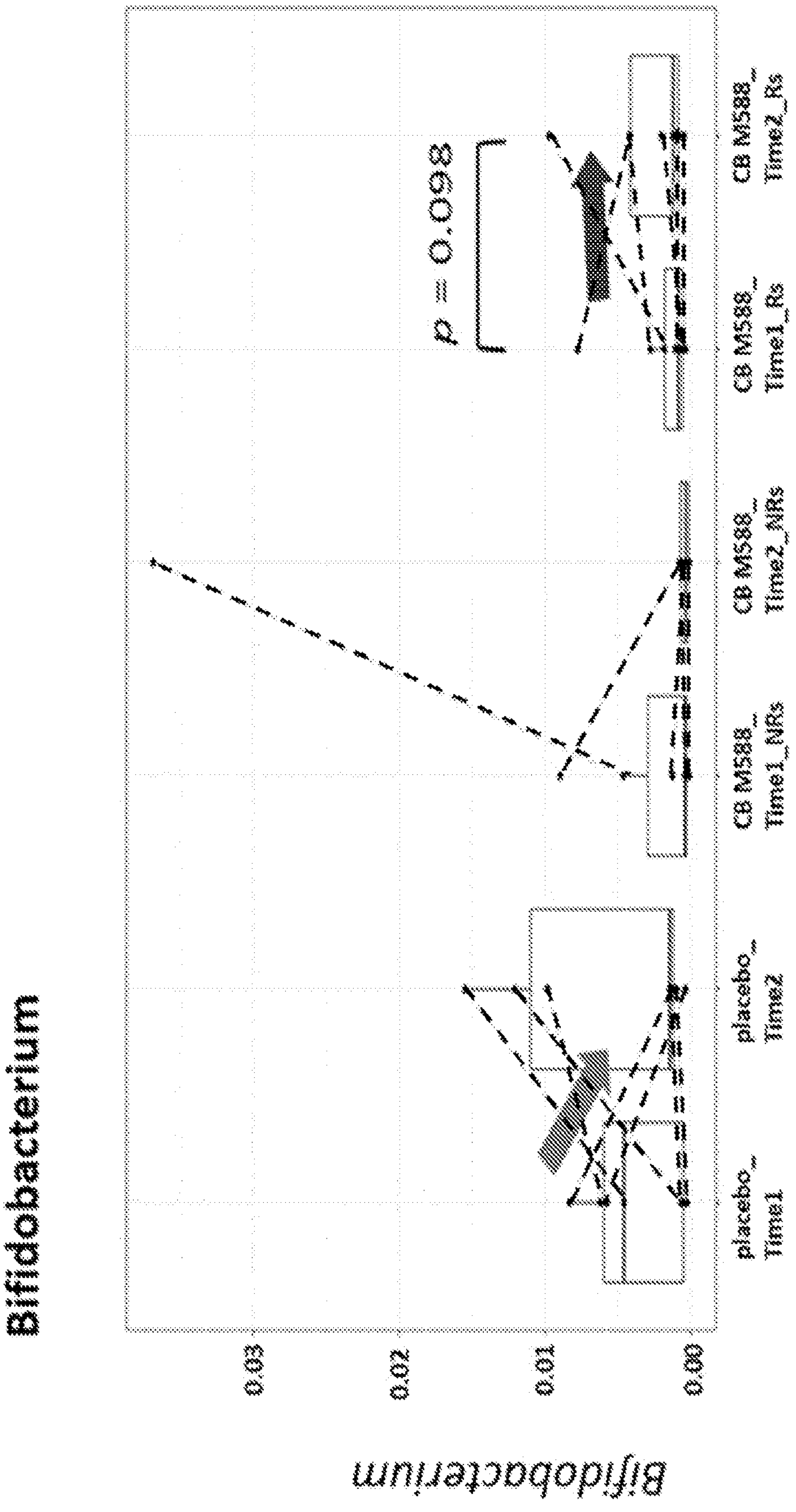
Figure 13B:
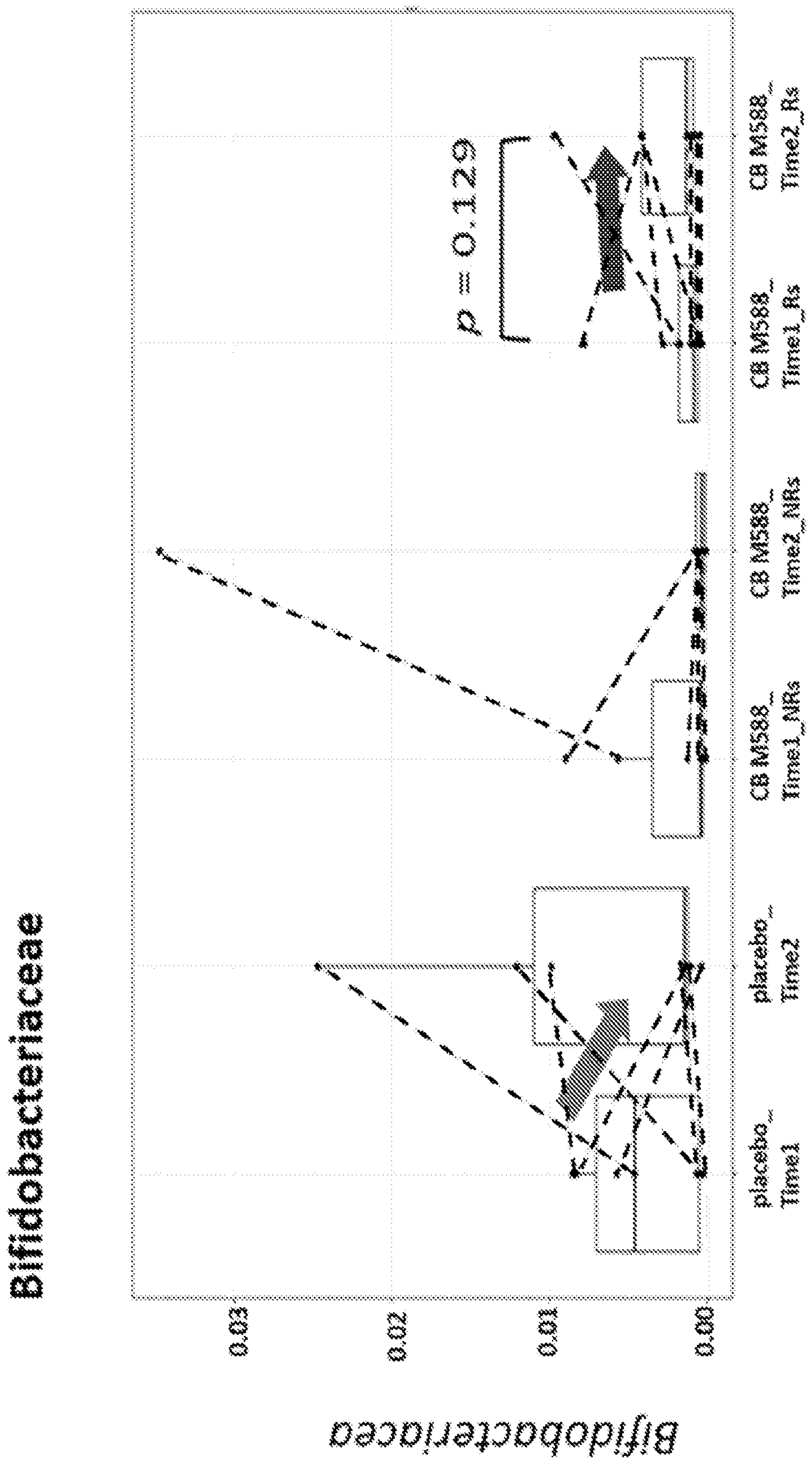
Figure 13C:
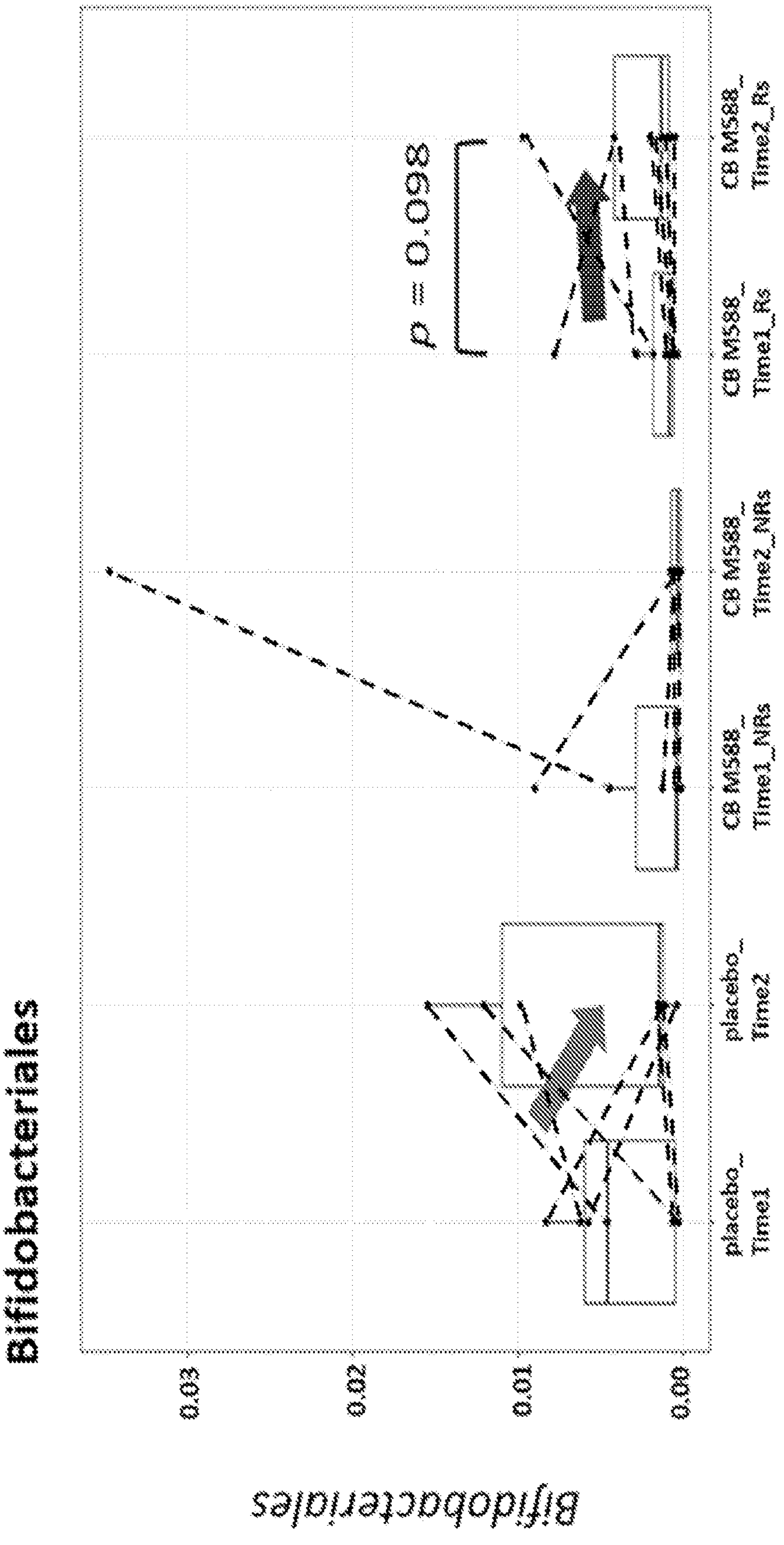
Figure 13D:
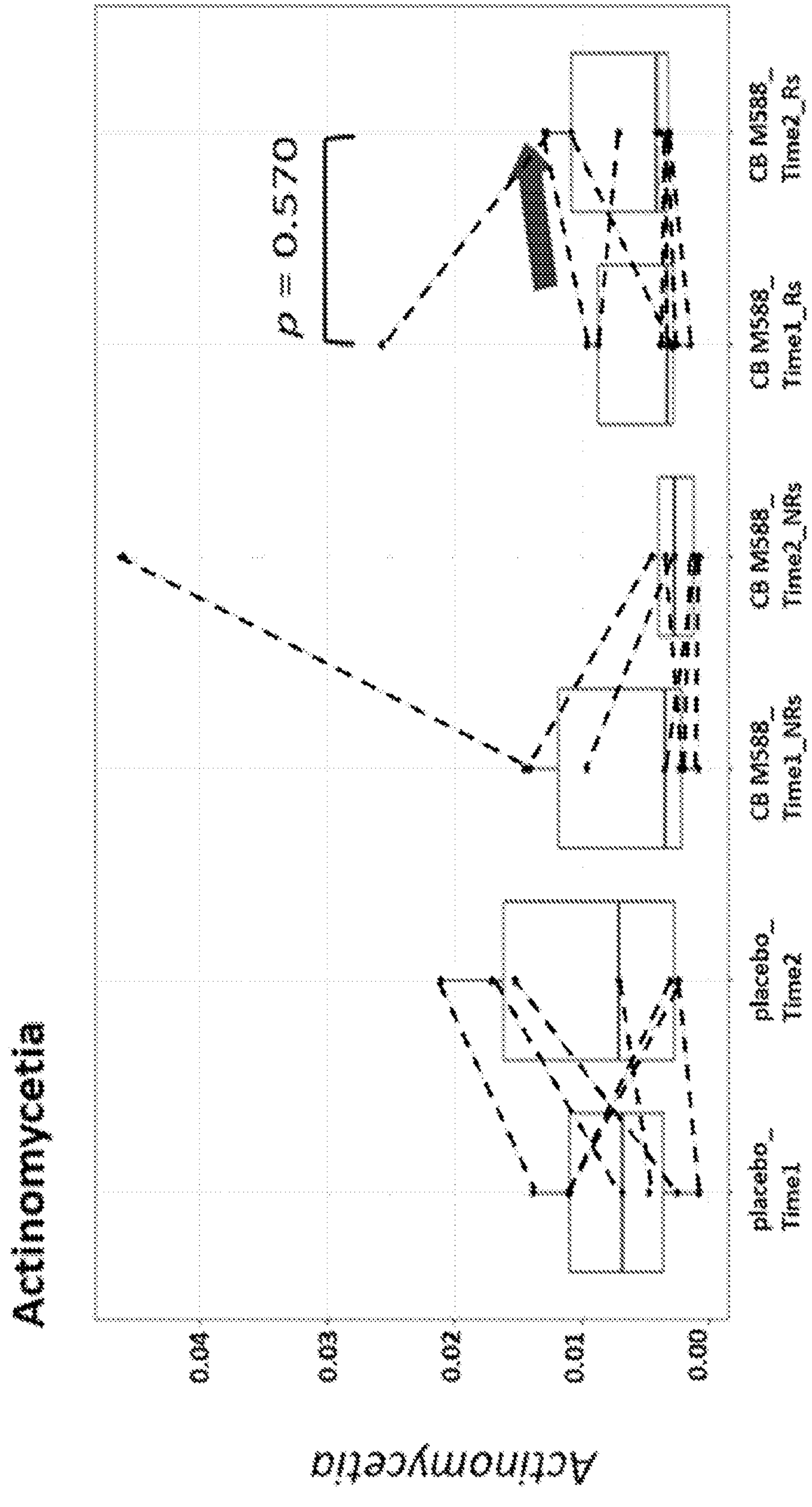
Figure 13E:
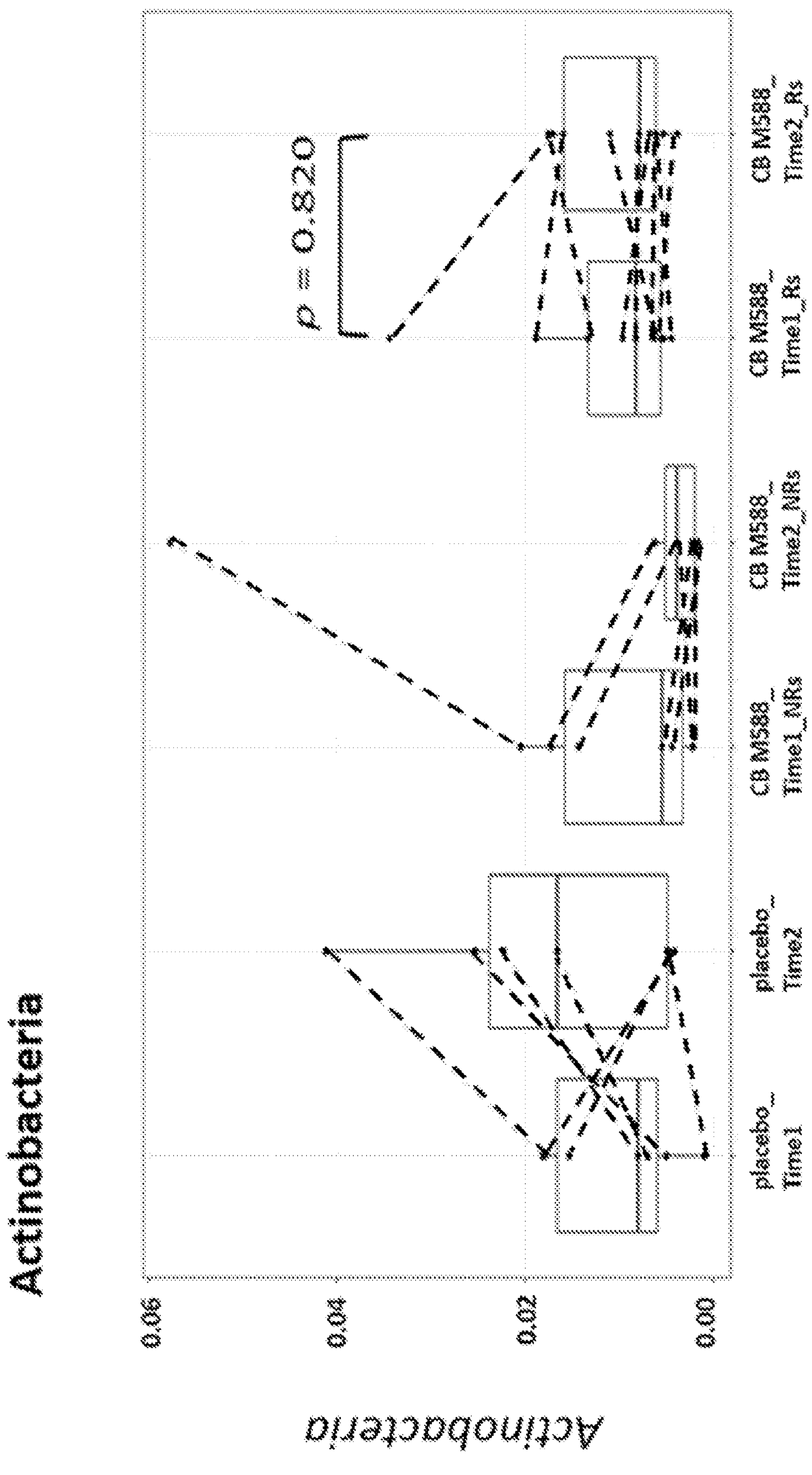

FIGS. 12A-12C are graphs illustrating the relative abundance of bacterial species including *Aminipila* sp. CBA3637 (FIG. 12A), *Bacteroides thetaiotaomicron* (FIG. 12B), and *Bifidobacterium breve* (FIG. 12C) in patients who were responsive (Rs) to CBM588 treatment as compared to patients who were non-responsive (NRs) to CBM588 treatment at Time 1 and Time 2.

FIGS. 13A-13E are graphs showing analysis of the relative abundance of the phylum Actinobacteria (FIG. 13E), the class Actinomycetia (FIG. 13D), the order Bifidobacteriales (FIG. 13C), family Bifidobacteriaceae (FIG. 13B) and genus *Bifidobacterium* (FIG. 13A) in patients who were responsive (Rs) to CBM588 treatment as compared to patients who were non-responsive (NRs) to CBM588 treatment at Time 1 and Time 2.

DETAILED DESCRIPTION OF THE INVENTION

Studies described herein illustrate that presence of types of gut bacteria (e.g., *Bifidobacterium*) in patients receiving immunotherapy (e.g. checkpoint inhibitors) for treatment of cancer (e.g. metastatic cancer, microsatellite instability high cancer, etc.) may be indicative of predisposed responsiveness to the immunotherapy. For example, butyric acid bacteria (e.g. *Clostridium butyricum* MIYAIRI 588), have immunomodulatory and anti-inflammatory effects on the intestinal epithelium, and may restore bacterial species, including *Bifidobacterium* spp and *Lactobacillus* spp, in the gut. Described herein are compositions and methods including administration of combination treatments (e.g. anti-cancer therapeutics and *Clostridium butyricum*) to subjects in need thereof. Applicants have identified the biologic effect of *Clostridium butyricum* in combination with anti-cancer agents (e.g. checkpoint inhibitors (nivolumab, ipilimumab, etc.)), and showed the efficacy of the combination treatment for treatment of cancers.

While various embodiments and aspects of the present invention are shown and described herein, it will be obvious to those skilled in the art that such embodiments and aspects are provided by way of example only. Numerous variations, changes, and substitutions will now occur to those skilled in the art without departing from the invention. It should be understood that various alternatives to the embodiments of the invention described herein may be employed in practicing the invention.

The section headings used herein are for organizational purposes only and are not to be construed as limiting the subject matter described. All documents, or portions of documents, cited in the application including, without limitation, patents, patent applications, articles, books, manuals, and treatises are hereby expressly incorporated by reference in their entirety for any purpose.

Unless defined otherwise, technical and scientific terms used herein have the same meaning as commonly understood by a person of ordinary skill in the art. See, e.g., Singleton et al., DICTIONARY OF MICROBIOLOGY AND MOLECULAR BIOLOGY 2nd ed., J. Wiley & Sons (New York, NY 1994); Sambrook et al., MOLECULAR CLONING, A LABORATORY MANUAL, Cold Springs Harbor Press (Cold Springs Harbor, N Y 1989). Any methods, devices and materials similar or equivalent to those described herein can be used in the practice of this invention. The following definitions are provided to facilitate understanding of certain terms used frequently herein and are not meant to limit the scope of the present disclosure.

Definitions

An amino acid residue in a protein "corresponds" to a given residue when it occupies the same essential structural position within the protein as the given residue.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid. The terms "non-naturally occurring amino acid" and "unnatural amino acid" refer to amino acid analogs, synthetic amino acids, and amino acid mimetics which are not found in nature.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

The terms "polypeptide," "peptide" and "protein" are used interchangeably herein to refer to a polymer of amino acid residues, wherein the polymer may in embodiments be conjugated to a moiety that does not consist of amino acids. The terms apply to amino acid polymers in which one or more amino acid residue is an artificial chemical mimetic of a corresponding naturally occurring amino acid, as well as to naturally occurring amino acid polymers and non-naturally occurring amino acid polymers. A "fusion protein" refers to a chimeric protein encoding two or more separate protein sequences that are recombinantly expressed as a single moiety.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the disclosure.

"Percentage of sequence identity" is determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The terms "identical" or percent "identity," in the context of two or more nucleic acids or polypeptide sequences, refer to two or more sequences or subsequences that are the same or have a specified percentage of amino acid residues or nucleotides that are the same (i.e., about 60% identity, preferably 65%, 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters described below, or by manual alignment and visual inspection (see, e.g., NCBI web site http://www.ncbi.nlm.nih.gov/BLAST/ or the like). Such sequences are then said to be "substantially identical." This definition also refers to, or may be applied to, the compliment of a test sequence. The definition also includes sequences that have deletions and/or additions, as well as those that have substitutions. As described below, the preferred algorithms can account for gaps and the like. Preferably, identity exists over a region that is at least about 25 amino acids or nucleotides in length, or more preferably over a region that is 50-100 amino acids or nucleotides in length.

An amino acid or nucleotide base "position" is denoted by a number that sequentially identifies each amino acid (or nucleotide base) in the reference sequence based on its position relative to the N-terminus (or 5'-end). Due to deletions, insertions, truncations, fusions, and the like that must be taken into account when determining an optimal alignment, in general the amino acid residue number in a test sequence determined by simply counting from the N-terminus will not necessarily be the same as the number of its corresponding position in the reference sequence. For example, in a case where a variant has a deletion relative to an aligned reference sequence, there will be no amino acid in the variant that corresponds to a position in the reference sequence at the site of deletion. Where there is an insertion in an aligned reference sequence, that insertion will not correspond to a numbered amino acid position in the reference sequence. In the case of truncations or fusions there can be stretches of amino acids in either the reference or aligned sequence that do not correspond to any amino acid in the corresponding sequence.

The terms "numbered with reference to" or "corresponding to," when used in the context of the numbering of a given amino acid or polynucleotide sequence, refers to the numbering of the residues of a specified reference sequence when the given amino acid or polynucleotide sequence is compared to the reference sequence.

The term "amino acid side chain" refers to the functional substituent contained on amino acids. For example, an amino acid side chain may be the side chain of a naturally occurring amino acid. Naturally occurring amino acids are those encoded by the genetic code (e.g., alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, or valine), as well as those amino acids that are later modified, e.g., hydroxyproline, γ-carboxyglutamate, and O-phosphoserine. In embodiments, the amino acid side chain may be a non-natural amino acid side chain. In embodiments, the amino acid side chain is H,

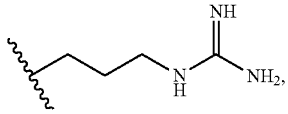 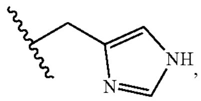,

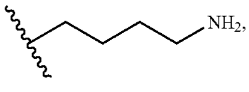 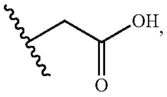,

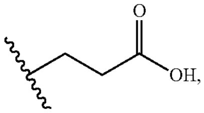 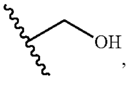, 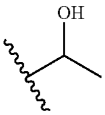,

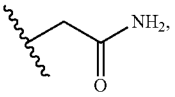 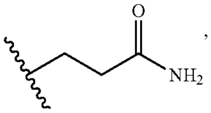, 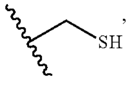,

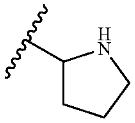, 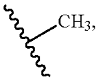 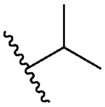, 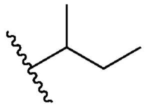,

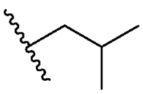, 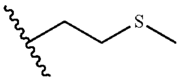, 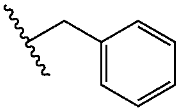,

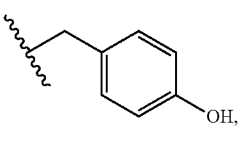 or 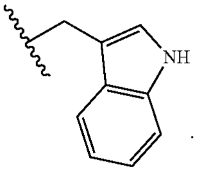.

The term "antibody" refers to a polypeptide encoded by an immunoglobulin gene or functional fragments thereof that specifically binds and recognizes an antigen. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

The phrase "specifically (or selectively) binds" to an antibody or "specifically (or selectively) immunoreactive with," when referring to a protein or peptide, refers to a binding reaction that is determinative of the presence of the protein, often in a heterogeneous population of proteins and other biologics. Thus, under designated immunoassay conditions, the specified antibodies bind to a particular protein at least two times the background and more typically more than 10 to 100 times background. Specific binding to an antibody under such conditions requires an antibody that is selected for its specificity for a particular protein. For example, polyclonal antibodies can be selected to obtain only a subset of antibodies that are specifically immunoreactive with the selected antigen and not with other proteins. This selection may be achieved by subtracting out antibodies that cross-react with other molecules. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, Using Antibodies, A Laboratory Manual (1998) for a description of immunoassay formats and conditions that can be used to determine specific immunoreactivity).

An exemplary immunoglobulin (antibody) structural unit comprises a tetramer. Each tetramer is composed of two identical pairs of polypeptide chains, each pair having one "light" (about 25 kDa) and one "heavy" chain (about 50-70 kDa). The N-terminus of each chain defines a variable region of about 100 to 110 or more amino acids primarily responsible for antigen recognition. The terms "variable heavy chain," "$V_H$," or "VH" refer to the variable region of an immunoglobulin heavy chain, including an Fv, scFv, dsFv or Fab; while the terms "variable light chain," "$V_L$" or "VL" refer to the variable region of an immunoglobulin light chain, including of an Fv, scFv, dsFv or Fab.

Examples of antibody functional fragments include, but are not limited to, complete antibody molecules, antibody fragments, such as Fv, single chain Fv (scFv), complementarity determining regions (CDRs), VL (light chain variable region), VH (heavy chain variable region), Fab, F(ab)2' and any combination of those or any other functional portion of an immunoglobulin peptide capable of binding to target antigen (see, e.g., FUNDAMENTAL IMMUNOLOGY (Paul ed., 4th ed. 2001). As appreciated by one of skill in the art, various antibody fragments can be obtained by a variety of methods, for example, digestion of an intact antibody with an enzyme, such as pepsin; or de novo synthesis. Antibody fragments are often synthesized de novo either chemically or by using recombinant DNA methodology. Thus, the term antibody, as used herein, includes antibody fragments either produced by the modification of whole antibodies, or those synthesized de novo using recombinant DNA methodologies (e.g., single chain Fv) or those identified using phage display libraries (see, e.g., McCafferty et al., (1990) *Nature* 348:552). The term "antibody" also includes bivalent or bispecific molecules, diabodies, triabodies, and tetrabodies. Bivalent and bispecific molecules are described in, e.g., Kostelny et al. (1992) *J. Immunol.* 148:1547, Pack and Pluckthun (1992) *Biochemistry* 31:1579, Hollinger et al. (1993), *PNAS*. USA 90:6444, Gruber et al. (1994) *J Immunol.* 152:5368, Zhu et al. (1997) *Protein Sci.* 6:781, Hu et al. (1996) *Cancer Res.* 56:3055, Adams et al. (1993) *Cancer Res.* 53:4026, and McCartney, et al. (1995) *Protein Eng.* 8:301.

A "chimeric antibody" is an antibody molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity. The preferred antibodies of, and for use according to the invention include humanized and/or chimeric monoclonal antibodies.

The term "isolated", when applied to a nucleic acid or protein, denotes that the nucleic acid or protein is essentially free of other cellular components with which it is associated in the natural state. It can be, for example, in a homogeneous state and may be in either a dry or aqueous solution. Purity and homogeneity are typically determined using analytical chemistry techniques such as polyacrylamide gel electrophoresis or high performance liquid chromatography. A protein that is the predominant species present in a preparation is substantially purified.

"Percentage of sequence identity" is determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The terms "identical" or percent "identity," in the context of two or more nucleic acids or polypeptide sequences, refer to two or more sequences or subsequences that are the same or have a specified percentage of amino acid residues or nucleotides that are the same (i.e., about 60% identity, preferably 65%, 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters described below, or by manual alignment and visual inspection (see, e.g., NCBI web site http://www.ncbi.nlm.nih.gov/BLAST/ or the like). Such sequences are then said to be "substantially identical." This definition also refers to, or may be applied to, the compliment of a test sequence. The definition also includes sequences that have deletions and/or additions, as well as those that have substitutions. As described below, the preferred algorithms can account for gaps and the like. Preferably, identity exists over a region that is at least about 25 amino acids or nucleotides in length, or more preferably over a region that is 50-100 amino acids or nucleotides in length.

For specific proteins described herein, the named protein includes any of the protein's naturally occurring forms, variants or homologs that maintain the protein transcription factor activity (e.g., within at least 50%, 80%, 90%, 95%, 96%, 97%, 98%, 99% or 100% activity compared to the native protein). In some embodiments, variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring form. In other embodiments, the protein is the protein as identified by its NCBI sequence reference. In other embodiments, the protein is the protein as identified by its NCBI sequence reference, homolog or functional fragment thereof.

The term "CTLA-4" or "CTLA-4 protein" as provided herein includes any of the recombinant or naturally-occurring forms of the cytotoxic T-lymphocyte-associated protein 4 (CTLA-4) or variants or homologs thereof that maintain CTLA-4 protein activity (e.g. within at least 50%, 80%, 90%, 95%, 96%, 97%, 98%, 99% or 100% activity compared to CTLA-4). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring CTLA-4 polypeptide. In embodiments, CTLA-4 is the protein as identified by the UniProt reference number P16410, homolog or functional fragment thereof.

A "PD-1 protein" or "PD-1" as referred to herein includes any of the recombinant or naturally-occurring forms of the Programmed cell death protein 1 (PD-1) also known as cluster of differentiation 279 (CD 279) or variants or homologs thereof that maintain PD-1 protein activity (e.g. within at least 50%, 80%, 90%, 95%, 96%, 97%, 98%, 99% or 100% activity compared to PD-1 protein). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring PD-1 protein. In embodiments, the PD-1 protein is substantially identical to the protein identified by the UniProt reference number Q15116 or a variant or homolog having substantial identity thereto. In embodiments, the PD-1 protein is substantially identical to the protein identified by the UniProt reference number Q02242 or a variant or homolog having substantial identity thereto.

A "PD-L1" or "PD-L1 protein" as referred to herein includes any of the recombinant or naturally-occurring forms of programmed death ligand 1 (PD-L1) also known as cluster of differentiation 274 (CD 274) or variants or homologs thereof that maintain PD-L1 activity (e.g. within at least 50%, 80%, 90%, 95%, 96%, 97%, 98%, 99% or 100% activity compared to PD-L1). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring PD-L1 protein. In embodiments, the PD-L1 protein is substantially identical to the protein identified by the UniProt reference number Q9NZQ7 or a variant or homolog having substantial identity thereto.

The terms "disease" or "condition" refer to a state of being or health status of a patient or subject capable of being treated with the compounds or methods provided herein. The disease may be a cancer. The disease may be an autoimmune disease. The disease may be an inflammatory disease. The disease may be an infectious disease. In some further instances, "cancer" refers to human cancers and carcinomas, sarcomas, adenocarcinomas, lymphomas, leukemias, etc., including solid and lymphoid cancers, kidney, breast, lung, bladder, colon, ovarian, prostate, pancreas, stomach, brain, head and neck, skin, uterine, testicular, glioma, esophagus, and liver cancer, including hepatocarcinoma, lymphoma, including B-acute lymphoblastic lymphoma, non-Hodgkin's lymphomas (e.g., Burkitt's, Small Cell, and Large Cell lymphomas), Hodgkin's lymphoma, leukemia (including AML, ALL, and CML), or multiple myeloma.

As used herein, the term "cancer" refers to all types of cancer, neoplasm or malignant tumors found in mammals (e.g. humans), including leukemias, lymphomas, carcinomas and sarcomas. Exemplary cancers that may be treated with a composition, compound or method provided herein include metastatic renal cell carcinoma (mRCC), non-small cell lung cancer, melanoma, sarcoma, lymphoma, breast cancer, bladder cancer, cervical cancer, colon cancer, head and neck cancer, liver cancer, stomach cancer, or rectal cancer. The cancer may be a microsatellite-instability high cancer. Additional examples include, cervix, uterus, gastric, thyroid carcinoma, cholangiocarcinoma, pancreatic adenocarcinoma, skin cutaneous melanoma, colon adenocarcinoma, rectum adenocarcinoma, stomach adenocarcinoma, esophageal carcinoma, head and neck squamous cell carcinoma, breast invasive carcinoma, lung adenocarcinoma, lung squamous cell carcinoma, non-small cell lung carcinoma, mesothelioma, multiple myeloma, medulloblastoma, neuroblastoma, glioma, glioblastoma multiforme, ovarian cancer, rhabdomyosarcoma, primary thrombocytosis, primary macroglobulinemia, primary brain tumors, neuroblastoma, malignant pancreatic insulanoma, malignant carcinoid, urinary bladder cancer, premalignant skin lesions, testicular cancer, thyroid cancer, Hodgkin's Disease, Non-Hodgkin's Lymphomas, esophageal cancer, genitourinary tract cancer, malignant hypercalcemia, endometrial cancer, adrenal cortical cancer, neoplasms of the endocrine or exocrine pancreas, medullary thyroid cancer, medullary thyroid carcinoma, melanoma, colorectal cancer, papillary thyroid cancer, hepatocellular carcinoma, or prostate cancer.

As used herein, the terms "metastasis" and "metastatic" can be used interchangeably and refer to the spread of a proliferative disease or disorder, e.g., cancer, from one organ or another non-adjacent organ or body part. "Metastatic cancer" may also be called "Stage IV cancer." Cancer occurs at an originating site, e.g., kidney, which site is referred to as a primary tumor, e.g., primary kidney cancer. Some cancer cells in the primary tumor or originating site acquire the ability to penetrate and infiltrate surrounding normal tissue in the local area and/or the ability to penetrate the walls of the lymphatic system or vascular system circulating through the system to other sites and tissues in the body. A second clinically detectable tumor formed from cancer cells of a primary tumor is referred to as a metastatic or secondary tumor. When cancer cells metastasize, the metastatic tumor and its cells are presumed to be similar to those of the original tumor. Thus, the phrase metastatic cancer may refer to a disease in which a subject has or had a primary tumor and has one or more secondary tumors. The phrases non-metastatic cancer or subjects with cancer that is not metastatic may refer to diseases in which subjects have a primary tumor but not one or more secondary tumors.

As used herein, the term "chemotherapeutic resistant cancer" or "chemotherapeutic resistant" refers to lack of intended response of a cancer to a chemotherapy. Chemotherapeutic resistance may refer to decreased sensitivity of the cancer to a chemotherapy compared to previous sensitivity to the chemotherapy. Thus, chemotherapeutic resistance may occur despite the cancer previously responding to the chemotherapy. Chemotherapeutic resistance may refer to the ability of cancer cells to survive and grow despite chemotherapy treatment.

The terms "treating", or "treatment" refers to any indicia of success in the therapy or amelioration of an injury, disease, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters; including the results of a physical examination, neuropsychiatric exams, and/or a psychiatric evaluation. The term "treating" and conjugations thereof, may include prevention of an injury, pathology, condition, or disease. In embodiments, treating is preventing. In embodiments, treating does not include preventing.

"Treating" or "treatment" as used herein (and as well-understood in the art) also broadly includes any approach for obtaining beneficial or desired results in a subject's condition, including clinical results. Beneficial or desired clinical results can include, but are not limited to, alleviation or amelioration of one or more symptoms or conditions, diminishment of the extent of a disease, stabilizing (i.e., not worsening) the state of disease, prevention of a disease's transmission or spread, delay or slowing of disease progression, amelioration or palliation of the disease state, diminishment of the reoccurrence of disease, and remission, whether partial or total and whether detectable or undetectable. In other words, "treatment" as used herein includes any cure, amelioration, or prevention of a disease. Treatment may prevent the disease from occurring; inhibit the disease's spread; relieve the disease's symptoms, fully or partially remove the disease's underlying cause, shorten a disease's duration, or do a combination of these things.

"Treating" and "treatment" as used herein include prophylactic treatment. Treatment methods include administering to a subject a therapeutically effective amount of an active agent. The administering step may consist of a single administration or may include a series of administrations. The length of the treatment period depends on a variety of factors, such as the severity of the condition, the age of the patient, the concentration of active agent, the activity of the compositions used in the treatment, or a combination thereof. It will also be appreciated that the effective dosage of an agent used for the treatment or prophylaxis may increase or decrease over the course of a particular treatment or prophylaxis regime. Changes in dosage may result and become apparent by standard diagnostic assays known in the art. In some instances, chronic administration may be required. For example, the compositions are administered to the subject in an amount and for a duration sufficient to treat the patient. In embodiments, the treating or treatment is no prophylactic treatment.

The term "prevent" refers to a decrease in the occurrence of disease symptoms in a patient. As indicated above, the prevention may be complete (no detectable symptoms) or partial, such that fewer symptoms are observed than would likely occur absent treatment.

"Patient" or "subject in need thereof" refers to a living organism suffering from or prone to a disease (e.g. cancer) or condition that can be treated by administration of a pharmaceutical composition as provided herein. Non-limiting examples include humans, other mammals, bovines, rats, mice, dogs, monkeys, goat, sheep, cows, deer, and other non-mammalian animals. In some embodiments, a patient is human.

A "effective amount" is an amount sufficient for a compound to accomplish a stated purpose relative to the absence of the compound (e.g. achieve the effect for which it is administered, treat a disease, reduce enzyme activity, increase enzyme activity, reduce a signaling pathway, or reduce one or more symptoms of a disease or condition). An example of an "effective amount" is an amount sufficient to contribute to the treatment, prevention, or reduction of a symptom or symptoms of a disease (e.g. cancer), which could also be referred to as a "therapeutically effective amount." A "reduction" of a symptom or symptoms (and grammatical equivalents of this phrase) means decreasing of the severity or frequency of the symptom(s), or elimination of the symptom(s). A "prophylactically effective amount" of a drug is an amount of a drug that, when administered to a subject, will have the intended prophylactic effect, e.g., preventing or delaying the onset (or reoccurrence) of an injury, disease, pathology or condition, or reducing the likelihood of the onset (or reoccurrence) of an injury, disease, pathology, or condition, or their symptoms. The full prophylactic effect does not necessarily occur by administration of one dose, and may occur only after administration of a series of doses. Thus, a prophylactically effective amount may be administered in one or more administrations. An "activity decreasing amount," as used herein, refers to an amount of antagonist required to decrease the activity of an enzyme relative to the absence of the antagonist. A "function disrupting amount," as used herein, refers to the amount of antagonist required to disrupt the function of an enzyme or protein relative to the absence of the antagonist. The exact amounts will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy,* 20th Edition, 2003, Gennaro, Ed., Lippincott, Williams & Wilkins).

By "therapeutically effective dose or amount" as used herein is meant a dose that produces effects for which it is administered (e.g. treating or preventing a disease). The exact dose and formulation will depend on the purpose of the treatment, and will be ascertainable by one skilled in the art using known techniques (see, e.g., Lieberman, Pharmaceutical Dosage Forms (vols. 1-3, 1992); Lloyd, The Art, Science and Technology of Pharmaceutical Compounding (1999); *Remington: The Science and Practice of Pharmacy,* 20th Edition, *Gennaro, Editor* (2003), and Pickar, Dosage Calculations (1999)). For example, for the given parameter, a therapeutically effective amount will show an increase or decrease of at least 5%, 10%, 15%, 20%, 25%, 40%, 50%, 60%, 75%, 80%, 90%, or at least 100%. Therapeutic efficacy can also be expressed as "-fold" increase or decrease. For example, a therapeutically effective amount can have at least a 1.2-fold, 1.5-fold, 2-fold, 5-fold, or more effect over a standard control. A therapeutically effective dose or amount may ameliorate one or more symptoms of a disease. A therapeutically effective dose or amount may prevent or delay the onset of a disease or one or more symptoms of a disease when the effect for which it is being administered is to treat a person who is at risk of developing the disease.

For any compound described herein, the therapeutically effective amount can be initially determined from cell culture assays. Target concentrations will be those concentrations of active compound(s) that are capable of achieving the methods described herein, as measured using the methods described herein or known in the art.

As is well known in the art, therapeutically effective amounts for use in humans can also be determined from animal models. For example, a dose for humans can be formulated to achieve a concentration that has been found to be effective in animals. The dosage in humans can be adjusted by monitoring compounds effectiveness and adjusting the dosage upwards or downwards, as described above. Adjusting the dose to achieve maximal efficacy in humans based on the methods described above and other methods is well within the capabilities of the ordinarily skilled artisan.

Dosages may be varied depending upon the requirements of the patient and the compound being employed. The dose administered to a patient, in the context of the present disclosure, should be sufficient to effect a beneficial therapeutic response in the patient over time. The size of the dose also will be determined by the existence, nature, and extent of any adverse side-effects. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached. Dosage amounts and intervals can be adjusted individually to provide levels of the administered compound effective for the particular clinical indication being treated. This will provide a therapeutic regimen that is commensurate with the severity of the individual's disease state.

As used herein, the term "administering" means oral administration, administration as a suppository, topical contact, intravenous, parenteral, intraperitoneal, intramuscular, intralesional, intrathecal, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc. In embodiments, the administering does not include administration of any active agent other than the recited active agent.

"Co-administer" it is meant that a composition described herein is administered at the same time, just prior to, or just after the administration of one or more additional therapies. The compounds provided herein can be administered alone or can be coadministered to the patient. Coadministration is meant to include simultaneous or sequential administration of the compounds individually or in combination (more than one compound). Thus, the preparations can also be combined, when desired, with other active substances (e.g. to reduce metabolic degradation). The compositions of the present disclosure can be delivered transdermally, by a topical route, or formulated as applicator sticks, solutions, suspensions, emulsions, gels, creams, ointments, pastes, jellies, paints, powders, and aerosols.

As used herein, "sequential administration" includes that the administration of two agents (e.g., the compounds or compositions described herein) occurs separately on the same day or do not occur on a same day (e.g., occurs on consecutive days).

As used herein, "concurrent administration" includes overlapping in duration at least in part. For example, when two agents (e.g., any of the agents or class of agents described herein that has bioactivity) are administered concurrently, their administration occurs within a certain desired time. The agents administration may begin and end on the same day. The administration of one agent can also precede the administration of a second agent by day(s) as long as both agents are taken on the same day at least once. Similarly, the administration of one agent can extend beyond the administration of a second agent as long as both agents are taken on the same day at least once. The bioactive agents/agents do not have to be taken at the same time each day to include concurrent administration.

As used herein, "intermittent administration includes the administration of an agent for a period of time (which can be considered a "first period of administration"), followed by a time during which the agent is not taken or is taken at a lower maintenance dose (which can be considered "off-period") followed by a period during which the agent is administered again (which can be considered a "second period of administration"). Generally, during the second phase of administration, the dosage level of the agent will match that administered during the first period of administration but can be increased or decreased as medically necessary.

"Control" or "control experiment" is used in accordance with its plain ordinary meaning and refers to an experiment in which the subjects or reagents of the experiment are treated as in a parallel experiment except for omission of a procedure, reagent, or variable of the experiment. In some instances, the control is used as a standard of comparison in evaluating experimental effects. In some embodiments, a control is the measurement of the activity of a protein in the absence of a compound as described herein (including embodiments and examples).

Cancer model organism, as used herein, is an organism exhibiting a phenotype indicative of cancer, or the activity of cancer causing elements, within the organism. The term cancer is defined above. A wide variety of organisms may serve as cancer model organisms, and include for example, cancer cells and mammalian organisms such as rodents (e.g. mouse or rat) and primates (such as humans). Cancer cell lines are widely understood by those skilled in the art as cells exhibiting phenotypes or genotypes similar to in vivo cancers. Cancer cell lines as used herein includes cell lines from animals (e.g. mice) and from humans.

An "anti-cancer agent" as used herein refers to a molecule (e.g. compound, peptide, protein, nucleic acid) used to treat cancer through destruction or inhibition of cancer cells or tissues. Anti-cancer agents may be selective for certain cancers or certain tissues. In embodiments, the anticancer agent is a checkpoint inhibitor. For example the anticancer agent may be a PD-1 inhibitor.

"Anti-cancer agent" and "anticancer agent" are used in accordance with their plain ordinary meaning and refers to a composition (e.g. compound, drug, antagonist, inhibitor, modulator) having antineoplastic properties or the ability to inhibit the growth or proliferation of cells. In embodiments, an anti-cancer agent is a chemotherapeutic. In embodiments, an anti-cancer agent is an agent identified herein having utility in methods of treating cancer. In embodiments, an anti-cancer agent is an agent approved by the FDA or similar regulatory agency of a country other than the USA, for treating cancer.

"Selective" or "selectivity" or the like of a compound refers to the compound's ability to discriminate between molecular targets.

"Specific", "specifically", "specificity", or the like of a compound refers to the compound's ability to cause a particular action, such as inhibition, to a particular molecular target with minimal or no action to other proteins in the cell.

A "cell" as used herein, refers to a cell carrying out metabolic or other function sufficient to preserve or replicate its genomic DNA. A cell can be identified by well-known methods in the art including, for example, presence of an intact membrane, staining by a particular dye, ability to produce progeny or, in the case of a gamete, ability to combine with a second gamete to produce a viable offspring. Cells may include prokaryotic and eukaroytic cells. Prokaryotic cells include but are not limited to bacteria. Eukaryotic cells include but are not limited to yeast cells and cells derived from plants and animals, for example mammalian, insect (e.g., *spodoptera*) and human cells. Cells may be useful when they are naturally nonadherent or have been treated not to adhere to surfaces, for example by trypsinization.

"Biological sample" or "sample" refer to materials obtained from or derived from a subject or patient. A biological sample includes sections of tissues such as biopsy and autopsy samples, and frozen sections taken for histological purposes. Such samples include bodily fluids such as blood and blood fractions or products (e.g., serum, plasma, platelets, red blood cells, and the like), sputum, tissue, cultured cells (e.g., primary cultures, explants, and transformed cells) stool, urine, synovial fluid, joint tissue, synovial tissue, synoviocytes, fibroblast-like synoviocytes, macrophage-like synoviocytes, immune cells, hematopoietic cells, fibroblasts, macrophages, T cells, etc. A biological sample is typically obtained from a eukaryotic organism, such as a mammal such as a primate e.g., chimpanzee or human; cow; dog; cat; a rodent, e.g., guinea pig, rat, mouse; rabbit; or a bird; reptile; or fish.

The terms "immune response" and the like refer, in the usual and customary sense, to a response by an organism that protects against disease. The response can be mounted by the innate immune system or by the adaptive immune system, as well known in the art.

The terms "modulating immune response" and the like refer to a change in the immune response of a subject as a consequence of administration of an agent, e.g., a compound or composition as disclosed herein, including embodiments thereof. Accordingly, an immune response can be activated or deactivated as a consequence of administration of an agent, e.g., a compound or composition as disclosed herein, including embodiments thereof.

"B Cells" or "B lymphocytes" refer to their standard use in the art. B cells are lymphocytes, a type of white blood cell (leukocyte), that develops into a plasma cell (a "mature B cell"), which produces antibodies. An "immature B cell" is a cell that can develop into a mature B cell. Generally, pro-B cells undergo immunoglobulin heavy chain rearrangement to become pro B pre B cells, and further undergo immunoglobulin light chain rearrangement to become an immature B cells. Immature B cells include T1 and T2 B cells.

"T cells" or "T lymphocytes" as used herein are a type of lymphocyte (a subtype of white blood cell) that plays a central role in cell-mediated immunity. They can be distinguished from other lymphocytes, such as B cells and natural killer cells, by the presence of a T-cell receptor on the cell surface. T cells include, for example, natural killer T (NKT) cells, cytotoxic T lymphocytes (CTLs), regulatory T (Treg) cells, and T helper cells. Different types of T cells can be distinguished by use of T cell detection agents.

A "memory T cell" is a T cell that has previously encountered and responded to its cognate antigen during prior infection, encounter with cancer or previous vaccination. At a second encounter with its cognate antigen memory T cells can reproduce (divide) to mount a faster and stronger immune response than the first time the immune system responded to the pathogen.

A "regulatory T cell" or "suppressor T cell" is a lymphocyte which modulates the immune system, maintains tolerance to self-antigens, and prevents autoimmune disease.

As used herein, the terms "immune checkpoint molecule", "immune checkpoint protein" or "checkpoint protein" may be used interchangeably and refer to molecules capable of modulating the duration and amplitude of physiological immune responses. Immune checkpoint molecules may inhibit (decrease) an immune response. Examples of inhibitory checkpoint molecules include, but are not limited to, PD-1, PD-L1, CTLA-4, adenosine A2A receptor (A2AR), B7-H3, B7-H4, BTLA, indoleamine 2,3-dioxygenase (IDO), killer immunoglobulin-like receptors (KIR), LAGS, PD-1, TIM-3, and V-domain immunoglobulin suppressor of T-cell activation (VISTA) protein. Alternatively, immune checkpoint molecules may stimulate (increase) an immune response. Examples of stimulatory checkpoint molecules include, but are not limited to, members of the tumor necrosis factor (TNF) receptor superfamily (e.g. CD27, CD40, OX40, glucocorticoid-induced TNFR family related gene (GITR), and CD137), members of the B7-CD28 superfamily (e.g. CD28 itself and Inducible T-cell costimulator (ICOS)).

Likewise, an "immune checkpoint inhibitor" or "checkpoint inhibitor" as provided herein refers to a substance (e.g., an antibody or fragment thereof, a small molecule) that is capable of inhibiting, or negatively affecting (e.g., decreasing) the activity or function of a checkpoint protein (e.g., decreasing expression or decreasing the activity of a checkpoint protein) relative to the activity or function of the checkpoint protein in the absence of the inhibitor. The checkpoint inhibitor may at least in part, partially or totally block stimulation, decrease, prevent, or delay activation, or inactivate, desensitize, or down-regulate signal transduction or enzymatic activity or the amount of a checkpoint protein. A "checkpoint inhibitor" may inhibit a checkpoint protein, e.g., by binding, partially or totally blocking, decreasing, preventing, delaying, inactivating, desensitizing, or down-regulating activity of the checkpoint protein. In embodiments, the checkpoint inhibitor is a small molecule. In embodiments, the checkpoint inhibitor is an antibody. In embodiments, the checkpoint inhibitor is an antibody fragment. In embodiments, the checkpoint inhibitor is an antibody variant. Thus, a PD-1 inhibitor is a molecule that negatively affects (e.g., decreases) the activity or function of PD-1. In embodiments, the PD-1 inhibitor is pembrolizumab, nivolumab, or cemiplimab. A PD-L1 inhibitor is a molecule that negatively affects (e.g., decreases) the activity or function of PD-L1. In embodiments, the PD-L1 inhibitor is atezolizumab, avelumab, or durvalumab. A CTLA-4 inhibitor is a molecule that negatively affects (e.g., decreases) the activity or function of CTLA-4. In embodiments, the CTLA-4 inhibitor is ipilimumab or tremelimumab.

The term "pharmaceutically acceptable salts" is meant to include salts of the active compounds that are prepared with relatively nontoxic acids or bases, depending on the particular substituents found on the compounds described herein. When compounds of the present disclosure contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present disclosure contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, oxalic, methanesulfonic, and the like. Also included are salts of amino acids such as arginate and the like, and salts of organic acids like glucuronic or galactunoric acids and the like (see, for example, Berge et al., "Pharmaceutical Salts", *Journal of Pharmaceutical Science,* 1977, 66, 1-19). Certain specific compounds of the present disclosure contain both basic and acidic functionalities that allow the compounds to be converted into either base or acid addition salts.

In addition to salt forms, the present disclosure provides compounds, which are in a prodrug form. Prodrugs of the compounds described herein are those compounds that readily undergo chemical changes under physiological conditions to provide the compounds of the present disclosure. Prodrugs of the compounds described herein may be converted in vivo after administration. Additionally, prodrugs can be converted to the compounds of the present disclosure by chemical or biochemical methods in an ex vivo environment, such as, for example, when contacted with a suitable enzyme or chemical reagent.

Certain compounds of the present disclosure can exist in unsolvated forms as well as solvated forms, including hydrated forms. In general, the solvated forms are equivalent to unsolvated forms and are encompassed within the scope of the present disclosure. Certain compounds of the present disclosure may exist in multiple crystalline or amorphous forms. In general, all physical forms are equivalent for the uses contemplated by the present disclosure and are intended to be within the scope of the present disclosure.

"Pharmaceutically acceptable excipient" and "pharmaceutically acceptable carrier" refer to a substance that aids the administration of an active agent to and absorption by a subject and can be included in the compositions of the present disclosure without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethycellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the disclosure. One of skill in the art will recognize that other pharmaceutical excipients are useful in the present disclosure.

The term "preparation" is intended to include the formulation of the active compound with or without carriers.

The terms "dose" and "dosage" are used interchangeably herein. A dose refers to the amount of active ingredient given to an individual at each administration. The dose will vary depending on a number of factors, including the range of normal doses for a given therapy, frequency of administration; size and tolerance of the individual; severity of the condition; risk of side effects; and the route of administration. One of skill will recognize that the dose can be modified depending on the above factors or based on therapeutic progress. The term "dosage form" refers to the particular format of the pharmaceutical or pharmaceutical composition, and depends on the route of administration. For example, a dosage form can be in a liquid form for nebulization, e.g., for inhalants, in a tablet or liquid, e.g., for oral delivery, or a saline solution, e.g., for injection. Dosage forms may include sachets, capsules, chewable gels, granules, powders, tablets, wafers, or the like.

As used herein, the term "about" means a range of values including the specified value, which a person of ordinary skill in the art would consider reasonably similar to the specified value. In embodiments, about means within a standard deviation using measurements generally acceptable in the art. In embodiments, about means a range extending to +/−10% of the specified value. In embodiments, about includes the specified value.

*Clostridium butyricum* is an anaerobic endospore-forming Gram-positive butyric acid-producing *bacillus. Clostridium butyricum* can be found in human and animal gastrointestinal tracts. *Clostridium butyricum* MIYAIRI 588, also known as CBM or CBM588, is a strain of the bacteria *Clostridium butyricum. Clostridium butyricum* MIYAIRI 588 may have immunomodulatory, anti-inflammatory and antineoplastic properties. *Clostridium butyricum* MIYAIRI 588 may restore gut microbiota, and therefore may normalize intestinal immune responses.

*Bifidobacterium* is a genus of gram-positive anaerobic bacteria. *Bifidobacterium* may reside in the gastrointestinal tract, vagina and mouth (*B. dentium*) of mammals, including humans. Bifidobacteria are one of the major genera of bacteria that make up the gastrointestinal tract microbiota in mammals. In embodiments, strains of *Bifidobacterium* may be included in live biotherapeutic products. In embodiments, *Bifidobacterium* may normalize intestinal immune responses when used by itself or in combination with other bacteria as a live biotherapeutic product.

*Dorea* is a Gram-positive and non-spore-forming bacterial genus from the family Lachnospiraceae, and may be found in mammalian guts and may occur in which occur in human feces. Elevated levels of *Dorea* may be found in individuals with autoimmune conditions. *Dorea* may normalize intestinal immune responses when used by itself or in combination with other bacteria as a live biotherapeutic product.

*Blautia* a gut microbial genus that is commonly found in the mammalian gut. *Blautia* produces butyric acid, which is used for cell processes throughout the body. Butyric acid can be used as a therapy for Irritable Bowel Syndrome (IBS); therefore *Blautia* may be a target for treating IBS. *Blautia* may have anti-inflammatory properties and may make the gut environment less tolerable to pathogenic bacteria. In embodiments, *Blautia* may be used by itself or in combination with other bacteria as a live biotherapeutic product.

*Akkermansia municiphila* is a species of human intestinal mucin-degrading bacterium. *Akkermansia municiphila* may be a target for treatment of obesity, diabetes, and inflammation. In embodiments, *Akkermansia municiphila* may be used by itself or in combination with other bacteria as a live biotherapeutic product.

A "live biotherapeutic product" or "LBP", as used herein, refers to a biological product that contains live organisms and may be used for the prevention, treatment, or cure of a disease. For example, the live biotherapeutic product may contain microorganisms including live bacteria or yeast. The microorganisms may be naturally occurring, recombinant, or clonally selected. The live biotherapeutic product may be dried and remain alive for an extended period of time (e.g. 1-2 years). In embodiments, the live biotherapeutic product is a bacteria. In embodiments, the live biotherapeutic product is *Clostridium butyricum* Miyairi 588 (CBM588). In embodiments, the live biotherapeutic product is CBM588 in combination with another bacterial species, including but not limited to another strain of *Clostridium butyricum*, a strain from the genus *Bifidobacterium*, a strain from the genus *Dorea*, a strain from the genus *Blautia*, or *Akkermansia municiphila*. In embodiments, the live biotherapeutic product is CBM588 in combination with multiple other bacterial species, including but not limited to one or more other strains of *Clostridium butyricum*, one or more strains from the genus *Bifidobacterium*, one or more strains from the genus *Dorea*, one or more strains from the genus *Blautia*, or *Akkermansia municiphila*.

As used herein, a "recombinant live biotherapeutic product" or "recombinant LBP" refers to a live biotherapeutic product including microorganisms that have been genetically modified through the purposeful addition, deletion, or modification of genetic material.

The term "*Clostridium butyricum* MIYAIRI 588 live biotherapeutic product" or "CBM588 LBP" as used herein refers to *Clostridium butyricum* MIYAIRI 588 when used for the prevention, treatment, or cure of a disease. CBM588 is described in further detail in Japanese patent JPH1142081A ("Production of *Clostridium butyricum*", published Feb. 16, 1999), which is incorporated herein by reference in its entirety for all purposes. CBM588 was deposited with the Ministry of International Trade and Industry Agency of Industrial Science Research Institute under the accession number of FERM BP-2789 (FERM BP-2789). In embodiments, CBM588 LBP may be an anti-cancer agent when administered with other anti-cancer agents (e.g. immune checkpoint inhibitors). In embodiments, CBM388 LBP is administered in combination with another bacterial species, including but not limited to another strain of *Clostridium butyricum*, a strain from the genus *Bifidobacterium*, a strain from the genus *Dorea*, a strain from the genus *Blautia*, or *Akkermansia municiphila*. In embodiments, CBM388 LBP is administered in combination with multiple other bacterial species, including but not limited to one or more other strains of *Clostridium butyricum*, one or more strains from the genus *Bifidobacterium*, one or more strains from the genus *Dorea*, one or more strains from the genus *Blautia*, and/or *Akkermansia municiphila*.

Methods

Described herein are methods for treating cancer, the methods including administering to a subject in need thereof *Clostridium butyricum* and an anti-cancer agent. Without wishing to be bound by scientific theory, *Clostridium butyricum* (e.g. *Clostridium butyricum* MIYAIRI 588 live biotherapeutic product (CBM588 LBP)) is contemplated to modulate levels of specific types of bacteria (e.g. *bifidobacterium*) in the gastrointestinal tract microbiome. In embodiments, increases or decreases in levels of specific types of bacteria enhances the therapeutic effects of the anti-cancer agent (e.g. an immune checkpoint inhibitor). Thus, the *Clostridium butyricum* (e.g. CBM588 LBP) provided herein including embodiments thereof is contemplated to enhance the therapeutic effects of the anti-cancer agent.

Thus, in an aspect is provided a method for treating cancer in a subject in need thereof, the method including administering to the subject a therapeutically effective amount of an anti-cancer agent and *Clostridium butyricum*. In embodiments, the *Clostridium butyricum* is a live biotherapeutic product. In embodiments, the *Clostridium butyricum* live biotherapeutic product is *Clostridium butyricum* MIYAIRI 588 live biotherapeutic product (CBM588 LBP).

For the method provided herein, in embodiments, the anti-cancer agent is a checkpoint inhibitor. In embodiments, the checkpoint inhibitor is a PD-1, PD-L1 or CTLA-4 inhibitor. In embodiments, the checkpoint inhibitor is a PD-1 inhibitor. In embodiments, the checkpoint inhibitor is a PD-L1 inhibitor. In embodiments, the checkpoint inhibitor is a CTLA-4 inhibitor. In embodiments, the checkpoint inhibitor is nivolumab, ipilimumab, pembrolizumab, cemiplimab, durvalumab, daclizumab, avelumab, or atezolizumab. In embodiments, the checkpoint inhibitor is pembrolizumab. In embodiments, the checkpoint inhibitor is cemiplimab. In embodiments, the checkpoint inhibitor is durvalumab. In embodiments, the checkpoint inhibitor is daclizumab. In embodiments, the checkpoint inhibitor is avelumab. In embodiments, the checkpoint inhibitor is atezolizumab. In embodiments the checkpoint inhibitor is nivolumab. In embodiments the checkpoint inhibitor is ipilimumab. In embodiments the checkpoint inhibitor is nivolumab or ipilimumab.

For the method provided herein, in embodiments, the method further includes administering a second anti-cancer agent. In embodiments, the second anti-cancer agent is different from the first anti-cancer agent. In embodiments, the second anti-cancer agent is a second checkpoint inhibitor. In embodiments, the second checkpoint inhibitor is a PD-1, PD-L1 or CTLA-4 inhibitor. In embodiments, the second checkpoint inhibitor is a PD-1 inhibitor. In embodiments, the second checkpoint inhibitor is a PD-L1 inhibitor. In embodiments, the second checkpoint inhibitor is a CTLA-4 inhibitor. In embodiments, the second checkpoint inhibitor is nivolumab, ipilimumab, pembrolizumab, cemiplimab, durvalumab, daclizumab, avelumab, or atezolizumab. In embodiments, the second checkpoint inhibitor is pembrolizumab. In embodiments, the second checkpoint inhibitor is cemiplimab. In embodiments, the second checkpoint inhibitor is durvalumab. In embodiments, the second checkpoint inhibitor is daclizumab. In embodiments, the second checkpoint inhibitor is avelumab. In embodiments, the second checkpoint inhibitor is atezolizumab. In embodiments the second checkpoint inhibitor is nivolumab. In embodiments the second checkpoint inhibitor is ipilimumab. In embodiments, the second checkpoint inhibitor is nivolumab or ipilimumab.

In embodiments, the method includes simultaneous administration of an anti-cancer agent (e.g. a checkpoint inhibitor) and *Clostridium butyricum*, wherein the administration includes separate dosage forms or a single dosage form. In embodiments, the method includes simultaneous administration using separate dosage forms. In embodiments, the method includes simultaneous administration using a single dosage form. In embodiments, the method includes consecutive administration of the therapeutically effective amount of the anti-cancer agent (e.g. a checkpoint inhibitor) and *Clostridium butyricum* in either order, where there may be a time period when both (or all) active agents simultaneously exert their biological activities. Preparation and dosing schedules for such anti-cancer agents may be used according to manufacturers' instructions or as determined empirically by the skilled practitioner. Thus, for the method provided herein, in embodiments, the anti-cancer agent (e.g. a checkpoint inhibitor) and *Clostridium butyricum* are administered sequentially. In embodiments, the anti-cancer agent (e.g. a checkpoint inhibitor) and *Clostridium butyricum* are administered simultaneously.

In embodiments, the method provided herein includes administration of an anti-cancer agent (e.g. a checkpoint inhibitor) and *Clostridium butyricum*, and does not include administration of another active agent (e.g. another anti-cancer agent, live biotherapeutic product, microorganism, etc.). In embodiments, the method provided herein includes administration of a first anti-cancer agent (e.g. a first checkpoint inhibitor), a second anti-cancer agent (e.g. a second checkpoint inhibitor) and *Clostridium butyricum*, and does not include administration of another active agent (e.g. another anti-cancer agent, live biotherapeutic product, microorganism, etc.).

In another aspect is provided a method for treating cancer in a subject in need thereof, the method including administering to the subject an effective amount of an anti-cancer agent and *Clostridium butyricum* MIYAIRI 588 live biotherapeutic product (CBM588 LBP). In embodiments, the CBM588 LBP is administered in combination with another strain of *Clostridium butyricum*, a strain from the genus *Bifidobacterium*, a strain from the genus *Dorea*, a strain from the genus *Blautia*, or *Akkermansia municiphila*. In embodiments, the CBM588 LBP is administered with another strain of *Clostridium butyricum*. In embodiments, the CBM588 LBP is administered with a strain from the genus *Bifidobacterium*. In embodiments, the CBM588 LBP is administered with a strain from the genus *Dorea*. In embodiments, the CBM588 LBP is administered with a strain from the genus *Blautia*. In embodiments, the CBM588 LBP is administered with *Akkermansia municiphila*. In embodiments the CBM388 LBP is administered in combination with of one or more of other bacterial species, including but not limited to one or more other strains of *Clostridium butyricum*, one or more strains from the genus *Bifidobacterium*, one or more strains from the genus *Dorea*, one or more strains from the genus *Blautia*, and/or *Akkermansia municiphila*.

The method provided herein, including embodiments thereof is contemplated to be effective for treating cancer in a subject in need thereof. In embodiments, the cancer is metastatic renal cell carcinoma (mRCC), non-small cell lung cancer, melanoma, sarcoma, lymphoma, breast cancer, bladder cancer, cervical cancer, colon cancer, head and neck cancer, liver cancer, stomach cancer, or rectal cancer. In embodiments the cancer is metastatic renal cell carcinoma. In embodiments, the cancer is non-small cell lung cancer. In embodiments, the cancer is melanoma. In embodiments, the cancer is sarcoma. In embodiments, the cancer is lymphoma. In embodiments, the cancer is breast cancer. In embodiments, the cancer is bladder cancer. In embodiments, the cancer is cervical cancer. In embodiments, the cancer is colon cancer. In embodiments, the cancer is head and neck cancer. In embodiments, the cancer is liver cancer. In embodiments, the cancer is stomach cancer. In embodiments, the cancer is rectal cancer. In embodiments, the cancer is a metastatic cancer. In embodiments, the cancer is a chemotherapeutic resistant cancer.

As used herein, the terms "resistance" or "resistant" refer to lack of sensitivity or intended response of a cancer cell or cancer to a therapeutic agent, for example, an anti-cancer agent. For example, resistance to an anti-cancer agent can refer to loss of the anti-cancer effects (e.g. reduction in tumor volume or tumor volume growth) of the agent. In embodiments, resistance is resistance to a chemotherapeutic. Thus, a "chemotherapeutic resistant cancer" is a cancer that lacks sensitivity or the intended response to a chemotherapeutic.

In embodiments, the cancer is a recurrence of cancer. In embodiments, recurrence of cancer refers to a cancer that is detected after treatment, and after a period of time when the cancer was not detected. In embodiments, the recurrent cancer is found in the same region where it started (e.g. local recurrence). In embodiments, the recurrent cancer is found in a different region of the body from where it started (e.g. distant recurrence). In embodiments, the cancer is found in the lymph nodes near where it started (e.g. regional recurrence).

In embodiments, the cancer includes any solid tumor that is unable to or deficient in repairing error in DNA occurring during DNA replication. In embodiments, the cancer includes defective mismatch repair (MMR) genes. In embodiments, the cancer is a microsatellite instability high (MSI-H) cancer. As used herein, the term "microsatellite-instability high cancer" or "MSI-H cancer" refers to cancers with mutations in short, repeated sequences of DNA, referred to as microsatellites. In embodiments, MSI-H cancers result from dysfunction of mismatch repair genes due to mutations in genes that code for mismatch repair proteins. Due to accumulations in DNA microsatellites, MSI-H tumors may express high numbers of neoantigens. Thus, MSI-H tumors may be susceptible to immunotherapies. MSI-H cancers include colon cancer, gastric cancer, endometrium cancer, ovarian cancer, hepatobiliary tract cancer, urinary tract cancer, brain cancer, and skin cancers. In embodiments, the MSI-H cancer is endometrial cancer. In embodiments, the MSI-H cancer is colon cancer. In embodiments, the MSI-H cancer is gastric cancer. In embodiments, the MSI-H cancer is esophageal cancer. In embodiments, the MSI-H cancer is gastroesophageal junction cancer. In embodiments, the MSI-H cancer is ovarian cancer. In embodiments, the MSI-H cancer is urinary tract cancer. In embodiments, the MSI-H cancer is bladder cancer. In embodiments, the MSI-H cancer is renal cancer. In embodiments, the MSI-H cancer is hepatobiliary tract cancer. In embodiments, the MSI-H cancer is brain cancer. In embodiments, the MSI-H cancer is skin cancer. In embodiments, the MSI-H cancer is breast cancer. In embodiments, the MSI-H cancer is pancreatic cancer. In embodiments, the MSI-H cancer is prostate cancer. In embodiments, the MSI-H cancer is retroperitoneal adenocarcinoma. In embodiments, the MSI-H cancer is sarcoma. In embodiments, the MSI-H cancer is small cell lung cancer. In embodiments, the MSI-H cancer is small intestinal cancer. In embodiments, the MSI-H cancer is thyroid cancer.

The method provided herein including embodiments thereof, may cause a reduction in tumor volume or tumor volume growth, or other indicia of cancer growth inhibition or reduction. In embodiments, the method may reduce tumor volume or tumor volume growth or other indicia of cancer activity 10%, 20%, 30%, 40%, 50%, 60%, 70%, 80%, 90% or more in comparison to a control in the absence of said method. In embodiments, the method may reduce tumor volume or tumor volume growth or other indicia of cancer activity 1.5-fold, 2-fold, 3-fold, 4-fold, 5-fold, 10-fold or lower in comparison to a control in the absence of said method. In embodiments, the method may reduce tumor volume or tumor volume growth or other indicia of cancer activity 10%, 20%, 30%, 40%, 50%, 60%, 70%, 80%, 90% or more in comparison to treatment with an immune checkpoint inhibitor or *Clostridium butyricum* (e.g. CBM588 LBP). In embodiments, the methods can reduce tumor volume or tumor volume growth or other indicia of cancer activity 1.5-fold, 2-fold, 3-fold, 4-fold, 5-fold, 10-fold or lower in comparison to a treatment with an anti-cancer agent (e.g. a checkpoint inhibitor) or *Clostridium butyricum* (e.g. CBM588 LBP).

*Clostridium butyricum* is contemplated to enhance the anti-cancer effects of anti-cancer agents (e.g. checkpoint inhibitors). In instances, the anti-cancer effect is prolonged survival of a subject, decrease in tumor volume, decrease in the number of cancer cells, or other indicia of cancer growth inhibition or reduction. For example, the anti-cancer agent may result in about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% greater decrease in tumor volume or number of cancer cells compared to when the anti-cancer agent is used individually and separately from *Clostridium butyricum*. For example, the anti-cancer agent may result in about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% prolonged survival of the subject compared to when the anti-cancer agent is used individually and separately from *Clostridium butyricum*.

In embodiments, the anti-cancer agent is therapeutically effective at a dosage below its therapeutically effective amount when used in the absence of *Clostridium butyricum* for treating cancer. In embodiments, the therapeutically effect amount of the anti-cancer agent may be about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% of the therapeutically effective amount of the anti-cancer agent when used separately from *Clostridium butyricum*.

In embodiments, the method provided herein includes administering to the subject a therapeutically effective amount of an anti-cancer agent (e.g. a checkpoint inhibitor) and *Clostridium butyricum* (e.g. CBM588 LBP), as described above, wherein the combination has synergistic effect. In embodiments, the method provided herein includes administering to the subject a therapeutically effective amount of a first anti-cancer agent (e.g. a first checkpoint inhibitor), a second anti-cancer agent (e.g. a second checkpoint inhibitor) and *Clostridium butyricum*, as described above, wherein the combination has synergistic effect. In embodiments, the synergistic effect is more than a sum of effects from individual administration of the anti-cancer agent or *Clostridium butyricum*.

In instances, the synergistic effect is cancer cell death. Cancer cell death can be quantified, for example, by a decrease in tumor volume or decrease in the number of cancer cells. In embodiments, synergy between the anti-cancer agent (e.g. checkpoint inhibitor) and *Clostridium butyricum* may result in about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% greater decrease in tumor volume or number of cancer cells than the sum of the decrease when the anti-cancer agent (e.g. checkpoint inhibitor) and *Clostridium butyricum* (e.g. CBM588 LBP) are used individually and separately.

In embodiments, synergy between the anti-cancer agent (e.g. checkpoint inhibitor) and *Clostridium butyricum* may result in 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% greater inhibition of the activity of one or more of an immune checkpoint molecule (e.g. CTLA-4, PD-1, PD-L1, etc.) than the sum of the inhibition when the anti-cancer agent (e.g. checkpoint inhibitor) and *Clostridium butyricum* (e.g. CBM588 LBP) are used individually and separately.

In instances, the synergistic effect is inhibition of metastasis of cancer in a subject. In embodiments, synergy between the anti-cancer agent (e.g. checkpoint inhibitor) and *Clostridium butyricum* (e.g. CBM588 LBP) may result in 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% greater inhibition of metastasis of a cancer in a subject than the sum of the inhibition when the anti-cancer agent (e.g. checkpoint inhibitor) and *Clostridium butyricum* (e.g. CBM588 LBP) are used individually and separately.

In instances, the synergistic effect is prolonged survival of a subject having cancer. In embodiments, synergy between the anti-cancer agent (e.g. checkpoint inhibitor) and *Clostridium butyricum* (e.g. CBM588 LBP) may result in 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% prolonged survival in a subject compared to when the anti-cancer agent (e.g. checkpoint inhibitor) and *Clostridium butyricum* (e.g. CBM588 LBP) are used individually and separately.

A "synergistic amount" as used herein refers to the sum of a first amount (e.g., an amount of an anti-cancer agent) and a second amount (e.g. an amount of *Clostridium butyricum*) that results in a synergistic effect (i.e. an effect greater than an additive effect). Therefore, the terms "synergy", "synergism", "synergistic", "combined synergistic amount", and "synergistic therapeutic effect" which are used herein interchangeably, refer to a measured effect of the compound administered in combination where the measured effect is greater than the sum of the individual effects of each of the compounds provided herein administered alone as a single agent. More specifically, a "combined synergistic amount" is a combined amount of a first agent (e.g. an anti-cancer agent (e.g. a checkpoint inhibitor)) and second agent (e.g. *Clostridium butyricum*) effective to provide a synergistic effect (e.g. for treating cancer, including embodiments described herein). In embodiments, the methods herein including administering anti-cancer agent (e.g. a checkpoint inhibitor) and *Clostridium butyricum*, include administering a combined synergistic amount of the anti-cancer agent (e.g. a checkpoint inhibitor) and *Clostridium butyricum*. In embodiments, the pharmaceutical compositions herein including a anti-cancer agent (e.g. a checkpoint inhibitor) and *Clostridium butyricum*, include a combined synergistic amount of the anti-cancer agent (e.g. a checkpoint inhibitor) and *Clostridium butyricum* (e.g. CBM588 LBP).

In embodiments, a synergistic amount may be about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% of the amount of anti-cancer agent (e.g. a first checkpoint inhibitor, a second checkpoint inhibitor) provided herein when used separately from *Clostridium butyricum* (e.g. CBM588 LBP).

Pharmaceutical Compositions

Applicants have discovered that the composition described herein including embodiments thereof are surprisingly useful for treating cancers. The *Clostridium butyricum* described herein may enhance the therapeutic effect of an anti-cancer agent (e.g. a first checkpoint inhibitor, a second checkpoint inhibitor) when administered in combination or coadministered with the anti-cancer agent.

Thus, in an aspect is provided a pharmaceutical composition including an anti-cancer agent in a first dosage form and *Clostridium butyricum* in a second dosage form. In embodiments, the *Clostridium butyricum* is a live biotherapeutic product. In embodiments, the *Clostridium butyricum* live biotherapeutic product is *Clostridium butyricum* MIYAIRI 588 live biotherapeutic product (CBM588 LBP).

For the pharmaceutical compositions provided herein, in embodiments, the anti-cancer agent is an immune checkpoint inhibitor. Immune checkpoint proteins may inhibit or decrease an immune response, and a checkpoint inhibitor may downregulate or inhibit the effect of the checkpoint protein. In embodiments, the checkpoint inhibitor is a PD-1, PD-L1 or CTLA-4 inhibitor. In embodiments, the checkpoint inhibitor is a PD-1 inhibitor. In embodiments, the checkpoint inhibitor is a PD-L1 inhibitor. In embodiments, the checkpoint inhibitor is a CTLA-4 inhibitor. In embodiments, the checkpoint inhibitor is nivolumab, ipilimumab, pembrolizumab, cemiplimab, durvalumab, daclizumab, avelumab, or atezolizumab. In embodiments, the checkpoint inhibitor is pembrolizumab. In embodiments, the checkpoint inhibitor is cemiplimab. In embodiments, the checkpoint inhibitor is durvalumab. In embodiments, the checkpoint inhibitor is daclizumab. In embodiments, the checkpoint inhibitor is avelumab. In embodiments, the checkpoint inhibitor is atezolizumab. In embodiments, the checkpoint inhibitor is nivolumab or ipilimumab. In embodiments the checkpoint inhibitor is nivolumab. In embodiments the checkpoint inhibitor is ipilimumab.

In embodiments, the pharmaceutical composition further includes a second anti-cancer agent. In embodiments, the second anti-cancer agent is different from the first anti-cancer agent. In embodiments, the second anti-cancer agent is a second checkpoint inhibitor. In embodiments, the second checkpoint inhibitor is a PD-1, PD-L1 or CTLA-4 inhibitor. In embodiments, the second checkpoint inhibitor is a PD-1 inhibitor. In embodiments, the second checkpoint inhibitor is a PD-L1 inhibitor. In embodiments, the second checkpoint inhibitor is a CTLA-4 inhibitor. In embodiments, the second checkpoint inhibitor is nivolumab, ipilimumab, pembrolizumab, cemiplimab, durvalumab, daclizumab, avelumab, or atezolizumab. In embodiments, the second checkpoint inhibitor is pembrolizumab. In embodiments, the second checkpoint inhibitor is cemiplimab. In embodiments, the second checkpoint inhibitor is durvalumab. In embodiments, the second checkpoint inhibitor is daclizumab. In embodiments, the second checkpoint inhibitor is avelumab. In embodiments, the second checkpoint inhibitor is atezolizumab. In embodiments, the second checkpoint inhibitor is nivolumab or ipilimumab. In embodiments the second checkpoint inhibitor is nivolumab. In embodiments the second checkpoint inhibitor is ipilimumab.

In embodiments, the pharmaceutical composition provided herein includes an anti-cancer agent (e.g. a checkpoint inhibitor) and *Clostridium butyricum*, and does not include another active agent (e.g. another anti-cancer agent, live biotherapeutic product, microorganism, etc.). In embodiments, the pharmaceutical composition provided herein includes a first anti-cancer agent (e.g. a first checkpoint inhibitor), a second anti-cancer agent (e.g. a second checkpoint inhibitor) and *Clostridium butyricum*, and does not include another active agent (e.g. another anti-cancer agent, live biotherapeutic product, microorganism, etc.).

In another aspect is provided a pharmaceutical composition including an anti-cancer agent in a first dosage form and *Clostridium butyricum* MIYAIRI 588 live biotherapeutic product (CBM588 LBP) in a second dosage form. In embodiments, the pharmaceutical composition includes another strain of *Clostridium butyricum*, a strain from the genus *Bifidobacterium*, a strain from the genus *Dorea*, a strain from the genus *Blautia*, or *Akkermansia municiphila*. In embodiments, the pharmaceutical composition includes another strain of *Clostridium butyricum*. In embodiments, the pharmaceutical composition includes a strain from the genus *Bifidobacterium*. In embodiments, the pharmaceutical composition includes a strain from the genus *Dorea*. In embodiments, the pharmaceutical composition includes a strain from the genus *Blautia*. In embodiments, the pharmaceutical composition includes *Akkermansia municiphila*. In embodiments, the pharmaceutical composition includes CBM388 with of one or more of another bacterial species, including but not limited to one or more other strains of *Clostridium butyricum*, one or more strains from the genus *Bifidobacterium*, one or more strains from the genus *Dorea*, one or more strains from the genus *Blautia*, and/or *Akkermansia municiphila*.

In embodiments, the *Clostridium butyricum* is administered with a potency of about $0.1\times10^9$ colony forming unit (CFU)/dose to about $10\times10^9$ CFU/dose. In embodiments, the *Clostridium butyricum* is administered with a potency of about $0.5\times10^9$ CFU/dose to about $10\times10^9$ CFU/dose. In embodiments, the *Clostridium butyricum* is administered with a potency of about $1.0\times10^9$ CFU/dose to about $10\times10^9$ CFU/dose. In embodiments, the *Clostridium butyricum* is administered with a potency of about $1.5\times10^9$ CFU/dose to about $10\times10^9$ CFU/dose. In embodiments, the *Clostridium butyricum* is administered with a potency of about $2.0\times10^9$ CFU/dose to about $10\times10^9$ CFU/dose. In embodiments, the *Clostridium butyricum* is administered with a potency of about $2.5\times10^9$ CFU/dose to about $10\times10^9$ CFU/dose. In embodiments, the *Clostridium butyricum* is administered with a potency of about $3.0\times10^9$ CFU/dose to about $10\times10^9$ CFU/dose. In embodiments, the *Clostridium butyricum* is administered with a potency of about $3.5\times10^9$ CFU/dose to about $10\times10^9$ CFU/dose. In embodiments, the *Clostridium butyricum* is administered with a potency of about $4.0\times10^9$ CFU/dose to about $10\times10^9$ CFU/dose. In embodiments, the *Clostridium butyricum* is administered with a potency of about $4.5\times10^9$ CFU/dose to about $10\times10^9$ CFU/dose. In embodiments, the *Clostridium butyricum* is administered with a potency of about $5.0\times10^9$ CFU/dose to about $10\times10^9$ CFU/dose. In embodiments, the *Clostridium butyricum* is administered with a potency of about $5.5\times10^9$ CFU/dose to about $10\times10^9$ CFU/dose. In embodiments, the *Clostridium butyricum* is administered with a potency of about $6.0\times10^9$ CFU/dose to about $10\times10^9$ CFU/dose. In embodiments, the *Clostridium butyricum* is administered with a potency of about $6.5\times10^9$ CFU/dose to about $10\times10^9$ CFU/dose. In embodiments, the *Clostridium butyricum* is administered with a potency of about $7.0\times10^9$ CFU/dose to about $10\times10^9$ CFU/dose. In embodiments, the *Clostridium butyricum* is administered with a potency of about $7.5\times10^9$ CFU/dose to about $10\times10^9$ CFU/dose. In embodiments, the *Clostridium butyricum* is administered with a potency of about $8.0\times10^9$ CFU/dose to about $10\times10^9$ CFU/dose. In embodiments, the *Clostridium butyricum* is administered with a potency of about $8.5\times10^9$ CFU/dose to about $10\times10^9$ CFU/dose. In embodiments, the *Clostridium butyricum* is administered with a potency of about $9.0\times10^9$ CFU/dose to about $10\times10^9$ CFU/dose. In embodiments, the *Clostridium butyricum* is administered with a potency of about $9.5\times10^9$ CFU/dose to about $10\times10^9$ CFU/dose.

In embodiments, the *Clostridium butyricum* is administered with a potency of about $0.1\times10^9$ CFU/dose to about $9.5\times10^9$ CFU/dose. In embodiments, the *Clostridium butyricum* is administered with a potency of about $0.1\times10^9$ CFU/dose to about $9.0\times10^9$ CFU/dose. In embodiments, the *Clostridium butyricum* is administered with a potency of about $0.1\times10^9$ CFU/dose to about $8.5\times10^9$ CFU/dose. In embodiments, the *Clostridium butyricum* is administered with a potency of about $0.1\times10^9$ CFU/dose to about $8.0\times10^9$ CFU/dose. In embodiments, the *Clostridium butyricum* is administered with a potency of about $0.1\times10^9$ CFU/dose to about $7.5\times10^9$ CFU/dose. In embodiments, the *Clostridium butyricum* is administered with a potency of about $0.1\times10^9$ CFU/dose to about $7.0\times10^9$ CFU/dose. In embodiments, the *Clostridium butyricum* is administered with a potency of about $0.1\times10^9$ CFU/dose to about $6.5\times10^9$ CFU/dose. In embodiments, the *Clostridium butyricum* is administered with a potency of about $0.1\times10^9$ CFU/dose to about $6.0\times10^9$ CFU/dose. In embodiments, the *Clostridium butyricum* is administered with a potency of about $0.1\times10^9$ CFU/dose to about $5.5\times10^9$ CFU/dose. In embodiments, the *Clostridium butyricum* is administered with a potency of about $0.1\times10^9$ CFU/dose to about $5.0\times10^9$ CFU/dose. In embodiments, the *Clostridium butyricum* is administered with a potency of about $0.1\times10^9$ CFU/dose to about $4.5\times10^9$ CFU/dose. In embodiments, the *Clostridium butyricum* is administered with a potency of about $0.1\times10^9$ CFU/dose to about $4.0\times10^9$ CFU/dose. In embodiments, the *Clostridium butyricum* is administered with a potency of about $0.1\times10^9$ CFU/dose to about $3.5\times10^9$ CFU/dose. In embodiments, the *Clostridium butyricum* is administered with a potency of about $0.1\times10^9$ CFU/dose to about $3.0\times10^9$ CFU/dose. In embodiments, the *Clostridium butyricum* is administered with a potency of about $0.1\times10^9$ CFU/dose to about $2.5\times10^9$ CFU/dose. In embodiments, the *Clostridium butyricum* is administered with a potency of about $0.1\times10^9$ CFU/dose to about $2.0\times10^9$ CFU/dose. In embodiments, the *Clostridium butyricum* is administered with a potency of about $0.1\times10^9$ CFU/dose to about $1.5\times10^9$ CFU/dose. In embodiments, the *Clostridium butyricum* is administered with a potency of about $0.1\times10^9$ CFU/dose to about $1.0\times10^9$ CFU/dose. In embodiments, the *Clostridium butyricum* is administered with a potency of about $0.1\times10^9$ CFU/dose to about $0.5\times10^9$ CFU/dose.

In embodiments, the *Clostridium butyricum* is administered with a potency of about $0.1\times10^9$ CFU/dose, $0.5\times10^9$ CFU/dose, $1.5\times10^9$ CFU/dose, $2.0\times10^9$ CFU/dose, about $2.5\times10^9$ CFU/dose, $3.0\times10^9$ CFU/dose, $3.5\times10^9$ CFU/dose, $4.0\times10^9$ CFU/dose, $4.5\times10^9$ CFU/dose, $5.0\times10^9$ CFU/dose, $5.5\times10^9$ CFU/dose, about $6.0\times10^9$ CFU/dose, $6.5\times10^9$ CFU/dose, $7.0\times10^9$ CFU/dose, $7.5\times10^9$ CFU/dose, $8.0\times10^9$ CFU/dose, $8.5\times10^9$ CFU/dose, $9.0\times10^9$ CFU/dose, $9.5\times10^9$ CFU/dose, or $10\times10^9$ CFU/dose. In embodiments, the *Clostridium butyricum* is administered with a potency of about $2.5\times10^9$ CFU/dose. In embodiments, the *Clostridium butyricum* is administered with a potency of $2.5\times10^9$ CFU/dose. In embodiments, the *Clostridium butyricum* is administered with a potency of about $5.0\times10^9$ CFU/dose. In embodiments, the *Clostridium butyricum* is administered with a potency of $5.0 \times 10^9$ CFU/dose. The potency of *Clostridium butyricum* may be any value or subrange within the recited ranges, including endpoints, or any range between any of the recited values.

For the dosages of *Clostridium butyricum* provided herein, in embodiments the dosage may be divided for administration. In embodiments, the dosage may be divided by about ½, about ⅓, about ¼, about ⅕, or about ⅙ for administration. In embodiments, the dosage may be divided by about ½. In embodiments, the dosage may be divided by about ⅓. In embodiments, the dosage may be divided by about ¼. In embodiments, the dosage may be divided by about ⅕. In embodiments, the dosage may be divided by about ⅙.

In embodiments, each dosage contains about 20 mg to about 1020 mg of active pharmaceutical ingredient (API). In embodiments, each dosage contains about 120 mg to about 1020 mg of API. In embodiments, each dosage contains about 220 mg to about 1020 mg of API. In embodiments, each dosage contains about 320 mg to about 1020 mg of API. In embodiments, each dosage contains about 420 mg to about 1020 mg of API. In embodiments, each dosage contains about 520 mg to about 1020 mg of API. In embodiments, each dosage contains about 620 mg to about 1020 mg of API. In embodiments, each dosage contains about 720 mg to about 1020 mg of API. In embodiments, each dosage contains about 820 mg to about 1020 mg of API. In embodiments, each dosage contains about 920 mg to about 1020 mg of API.

In embodiments, each dosage contains about 20 mg to about 920 mg of active pharmaceutical ingredient (API). In embodiments, each dosage contains about 20 mg to about 820 mg of API. In embodiments, each dosage contains about 20 mg to about 720 mg of API. In embodiments, each dosage contains about 20 mg to about 620 mg of API. In embodiments, each dosage contains about 20 mg to about 520 mg of API. In embodiments, each dosage contains about 20 mg to about 420 mg of API. In embodiments, each dosage contains about 20 mg to about 320 mg of API. In embodiments, each dosage contains about 20 mg to about 220 mg of API. In embodiments, each dosage contains about 20 mg to about 120 mg of API.

In embodiments, each dosage contains about 20 mg API, 120 mg API, 220 mg API, 320 mg API, 420 mg API, 520 mg API, 620 mg API, 720 mg API, 820 mg API, 920 mg API, or 1020 mg API. In embodiments, each dosage contains about 320 mg API. In embodiments, each dosage contains 320 mg API. The API may be any value or subrange within the recited ranges, including endpoints, or any range between any of the recited values.

For the dosages of *Clostridium butyricum* provided herein, in embodiments, *Clostridium butyricum* may be administered for about 1 week to about 100 weeks. In embodiments, *Clostridium butyricum* may be administered for about 10 weeks to about 100 weeks. In embodiments, *Clostridium butyricum* may be administered for about 20 weeks to about 100 weeks. In embodiments, *Clostridium butyricum* may be administered for about 30 weeks to about 100 weeks. In embodiments, *Clostridium butyricum* may be administered for about 40 weeks to about 100 weeks. In embodiments, *Clostridium butyricum* may be administered for about 50 weeks to about 100 weeks. In embodiments, *Clostridium butyricum* may be administered for about 60 weeks to about 100 weeks. In embodiments, *Clostridium butyricum* may be administered for about 70 weeks to about 100 weeks. In embodiments, *Clostridium butyricum* may be administered for about 80 weeks to about 100 weeks. In embodiments, *Clostridium butyricum* may be administered for about 90 weeks to about 100 weeks.

In embodiments, *Clostridium butyricum* may be administered for about 1 week to about 90 weeks. In embodiments, *Clostridium butyricum* may be administered for about 1 week to about 80 weeks. In embodiments, *Clostridium butyricum* may be administered for about 1 week to about 70 weeks. In embodiments, *Clostridium butyricum* may be administered for about 1 week to about 60 weeks. In embodiments, *Clostridium butyricum* may be administered for about 1 week to about 50 weeks. In embodiments, *Clostridium butyricum* may be administered for about 1 week to about 40 weeks. In embodiments, *Clostridium butyricum* may be administered for about 1 week to about 30 weeks. In embodiments, *Clostridium butyricum* may be administered for about 1 week to about 20 weeks. In embodiments, *Clostridium butyricum* may be administered for about 1 week to about 10 weeks.

In embodiments, *Clostridium butyricum* may be administered for about 1 week, 10 weeks, 20 weeks, 30 weeks, 40 weeks, 50 weeks, 60 weeks, 70 weeks, 80 weeks, 90 weeks, or 100 weeks. The *Clostridium butyricum* administration time range may be any value or subrange within the recited ranges, including endpoints, or any range between any of the recited values.

For the dosages of *Clostridium butyricum* provided herein, in embodiments, *Clostridium butyricum* may be administered once daily for about 1 week to about 100 weeks. In embodiments, *Clostridium butyricum* may be administered once daily for about 10 weeks to about 100 weeks. In embodiments, *Clostridium butyricum* may be administered once daily for about 20 weeks to about 100 weeks. In embodiments, *Clostridium butyricum* may be administered once daily for about 30 weeks to about 100 weeks. In embodiments, *Clostridium butyricum* may be administered once daily for about 40 weeks to about 100 weeks. In embodiments, *Clostridium butyricum* may be administered once daily for about 50 weeks to about 100 weeks. In embodiments, *Clostridium butyricum* may be administered once daily for about 60 weeks to about 100 weeks. In embodiments, *Clostridium butyricum* may be administered once daily for about 70 weeks to about 100 weeks. In embodiments, *Clostridium butyricum* may be administered once daily for about 80 weeks to about 100 weeks.

In embodiments, *Clostridium butyricum* may be administered once daily for about 1 week to about 90 weeks. In embodiments, *Clostridium butyricum* may be administered once daily for about 1 week to about 80 weeks. In embodiments, *Clostridium butyricum* may be administered once daily for about 1 week to about 70 weeks. In embodiments, *Clostridium butyricum* may be administered once daily for about 1 week to about 60 weeks. In embodiments, *Clostridium butyricum* may be administered once daily for about 1 week to about 50 weeks. In embodiments, *Clostridium butyricum* may be administered once daily for about 1 week to about 40 weeks. In embodiments, *Clostridium butyricum* may be administered once daily for about 1 week to about 30 weeks. In embodiments, *Clostridium butyricum* may be administered once daily for about 1 week to about 20 weeks.

In embodiments, *Clostridium butyricum* may be administered once daily for about 1 week, about 10 weeks, about 20 weeks, about 30 weeks, about 40 weeks, about 50 weeks, about 60 weeks, about 70 weeks, about 80 weeks, about 90 weeks, or about 100 weeks. The *Clostridium butyricum* administration time points may be any value or subrange within the recited ranges, including endpoints, or any range between any of the recited values.

For the dosages of *Clostridium butyricum* provided herein, in embodiments, *Clostridium butyricum* may be administered twice daily for about 1 week to about 100 weeks. In embodiments, *Clostridium butyricum* may be administered twice daily for about 10 weeks to about 100 weeks. In embodiments, *Clostridium butyricum* may be administered twice daily for about 20 weeks to about 100 weeks. In embodiments, *Clostridium butyricum* may be administered twice daily for about 30 weeks to about 100 weeks. In embodiments, *Clostridium butyricum* may be administered twice daily for about 40 weeks to about 100 weeks. In embodiments, *Clostridium butyricum* may be administered twice daily for about 50 weeks to about 100 weeks. In embodiments, *Clostridium butyricum* may be administered twice daily for about 60 weeks to about 100 weeks. In embodiments, *Clostridium butyricum* may be administered twice daily for about 70 weeks to about 100 weeks. In embodiments, *Clostridium butyricum* may be administered twice daily for about 80 weeks to about 100 weeks.

In embodiments, *Clostridium butyricum* may be administered twice daily for about 1 week to about 90 weeks. In embodiments, *Clostridium butyricum* may be administered twice daily for about 1 week to about 80 weeks. In embodiments, *Clostridium butyricum* may be administered twice daily for about 1 week to about 70 weeks. In embodiments, *Clostridium butyricum* may be administered twice daily for about 1 week to about 60 weeks. In embodiments, *Clostridium butyricum* may be administered twice daily for about 1 week to about 50 weeks. In embodiments, *Clostridium butyricum* may be administered twice daily for about 1 week to about 40 weeks. In embodiments, *Clostridium butyricum* may be administered twice daily for about 1 week to about 30 weeks. In embodiments, *Clostridium butyricum* may be administered twice daily for about 1 week to about 20 weeks.

In embodiments, *Clostridium butyricum* may be administered twice daily for about 1 week, about 10 weeks, about 20 weeks, about 30 weeks, about 40 weeks, about 50 weeks, about 60 weeks, about 70 weeks, about 80 weeks, about 90 weeks, or about 100 weeks. The *Clostridium butyricum* administration time points may be any value or subrange within the recited ranges, including endpoints, or any range between any of the recited values.

For the dosages of *Clostridium butyricum* provided herein, in embodiments, *Clostridium butyricum* may be administered three times daily for about 1 week to about 100 weeks. In embodiments, *Clostridium butyricum* may be administered three times daily for about 10 weeks to about 100 weeks. In embodiments, *Clostridium butyricum* may be administered three times daily for about 20 weeks to about 100 weeks. In embodiments, *Clostridium butyricum* may be administered three times daily for about 30 weeks to about 100 weeks. In embodiments, *Clostridium butyricum* may be administered three times daily for about 40 weeks to about 100 weeks. In embodiments, *Clostridium butyricum* may be administered three times daily for about 50 weeks to about 100 weeks. In embodiments, *Clostridium butyricum* may be administered three times daily for about 60 weeks to about 100 weeks. In embodiments, *Clostridium butyricum* may be administered three times daily for about 70 weeks to about 100 weeks. In embodiments, *Clostridium butyricum* may be administered three times daily for about 80 weeks to about 100 weeks.

In embodiments, *Clostridium butyricum* may be administered three times daily for about 1 week to about 90 weeks. In embodiments, *Clostridium butyricum* may be administered three times daily for about 1 week to about 80 weeks. In embodiments, *Clostridium butyricum* may be administered three times daily for about 1 week to about 70 weeks. In embodiments, *Clostridium butyricum* may be administered three times daily for about 1 week to about 60 weeks. In embodiments, *Clostridium butyricum* may be administered three times daily for about 1 week to about 50 weeks. In embodiments, *Clostridium butyricum* may be administered three times daily for about 1 week to about 40 weeks. In embodiments, *Clostridium butyricum* may be administered three times daily for about 1 week to about 30 weeks. In embodiments, *Clostridium butyricum* may be administered three times daily for about 1 week to about 20 weeks.

In embodiments, *Clostridium butyricum* may be administered three times daily for about 1 week, about 10 weeks, about 20 weeks, about 30 weeks, about 40 weeks, about 50 weeks, about 60 weeks, about 70 weeks, about 80 weeks, about 90 weeks, or about 100 weeks. The *Clostridium butyricum* administration time points may be any value or subrange within the recited ranges, including endpoints, or any range between any of the recited values.

In embodiments, the *Clostridium butyricum* is administered once daily with a potency of about $0.1\times10^9$ CFU/dose to about $10\times10^9$ CFU/dose. In embodiments, the *Clostridium butyricum* is administered once daily with a potency of about $0.5\times10^9$ CFU/dose to about $10\times10^9$ CFU/dose. In embodiments, the *Clostridium butyricum* is administered once daily with a potency of about $1.0\times10^9$ CFU/dose to about $10\times10^9$ CFU/dose. In embodiments, the *Clostridium butyricum* is administered once daily with a potency of about $1.5\times10^9$ CFU/dose to about $10\times10^9$ CFU/dose. In embodiments, the *Clostridium butyricum* is administered once daily with a potency of about $2.0\times10^9$ CFU/dose to about $10\times10^9$ CFU/dose. In embodiments, the *Clostridium butyricum* is administered once daily with a potency of about $2.5\times10^9$ CFU/dose to about $10\times10^9$ CFU/dose. In embodiments, the *Clostridium butyricum* is administered once daily with a potency of about $3.0\times10^9$ CFU/dose to about $10\times10^9$ CFU/dose. In embodiments, the *Clostridium butyricum* is administered once daily with a potency of about $3.5\times10^9$ CFU/dose to about $10\times10^9$ CFU/dose. In embodiments, the *Clostridium butyricum* is administered once daily with a potency of about $4.0\times10^9$ CFU/dose to about $10\times10^9$ CFU/dose. In embodiments, the *Clostridium butyricum* is administered once daily with a potency of about $4.5\times10^9$ CFU/dose to about $10\times10^9$ CFU/dose. In embodiments, the *Clostridium butyricum* is administered once daily with a potency of about $5.0\times10^9$ CFU/dose to about $10\times10^9$ CFU/dose. In embodiments, the *Clostridium butyricum* is administered once daily with a potency of about $5.5\times10^9$ CFU/dose to about $10\times10^9$ CFU/dose. In embodiments, the *Clostridium butyricum* is administered once daily with a potency of about $6.0\times10^9$ CFU/dose to about $10\times10^9$ CFU/dose. In embodiments, the *Clostridium butyricum* is administered once daily with a potency of about $6.5\times10^9$ CFU/dose to about $10\times10^9$ CFU/dose. In embodiments, the *Clostridium butyricum* is administered once daily with a potency of about $7.0\times10^9$ CFU/dose to about $10\times10^9$ CFU/dose. In embodiments, the *Clostridium butyricum* is administered once daily with a potency of about $7.5\times10^9$ CFU/dose to about $10\times10^9$ CFU/dose. In embodiments, the *Clostridium butyricum* is administered once daily with a potency of about $8.0\times10^9$ CFU/dose to about $10\times10^9$ CFU/dose. In embodiments, the

*Clostridium butyricum* is administered once daily with a potency of about 8.5×10$^9$ CFU/dose to about 10×10$^9$ CFU/dose. In embodiments, the *Clostridium butyricum* is administered once daily with a potency of about 9.0×10$^9$ CFU/dose to about 10×10$^9$ CFU/dose.

In embodiments, the *Clostridium butyricum* is administered once daily with a potency of about 0.1×10$^9$ CFU/dose to about 9.5×10$^9$ CFU/dose. In embodiments, the *Clostridium butyricum* is administered once daily with a potency of about 0.1×10$^9$ CFU/dose to about 9.0×10$^9$ CFU/dose. In embodiments, the *Clostridium butyricum* is administered once daily with a potency of about 0.1×10$^9$ CFU/dose to about 8.5×10$^9$ CFU/dose. In embodiments, the *Clostridium butyricum* is administered once daily with a potency of about 0.1×10$^9$ CFU/dose to about 8.0×10$^9$ CFU/dose. In embodiments, the *Clostridium butyricum* is administered once daily with a potency of about 0.1×10$^9$ CFU/dose to about 7.5×10$^9$ CFU/dose. In embodiments, the *Clostridium butyricum* is administered once daily with a potency of about 0.1×10$^9$ CFU/dose to about 7.0×10$^9$ CFU/dose. In embodiments, the *Clostridium butyricum* is administered once daily with a potency of about 0.1×10$^9$ CFU/dose to about 6.5×10$^9$ CFU/dose. In embodiments, the *Clostridium butyricum* is administered once daily with a potency of about 0.1×10$^9$ CFU/dose to about 6.0×10$^9$ CFU/dose. In embodiments, the *Clostridium butyricum* is administered once daily with a potency of about 0.1×10$^9$ CFU/dose to about 5.5×10$^9$ CFU/dose. In embodiments, the *Clostridium butyricum* is administered once daily with a potency of about 0.1×10$^9$ CFU/dose to about 5.0×10$^9$ CFU/dose. In embodiments, the *Clostridium butyricum* is administered once daily with a potency of about 0.1×10$^9$ CFU/dose to about 4.5×10$^9$ CFU/dose. In embodiments, the *Clostridium butyricum* is administered once daily with a potency of about 0.1×10$^9$ CFU/dose to about 4.0×10$^9$ CFU/dose. In embodiments, the *Clostridium butyricum* is administered once daily with a potency of about 0.1×10$^9$ CFU/dose to about 3.5×10$^9$ CFU/dose. In embodiments, the *Clostridium butyricum* is administered once daily with a potency of about 0.1×10$^9$ CFU/dose to about 3.0×10$^9$ CFU/dose. In embodiments, the *Clostridium butyricum* is administered once daily with a potency of about 0.1×10$^9$ CFU/dose to about 2.5×10$^9$ CFU/dose. In embodiments, the *Clostridium butyricum* is administered once daily with a potency of about 0.1×10$^9$ CFU/dose to about 2.0×10$^9$ CFU/dose. In embodiments, the *Clostridium butyricum* is administered once daily with a potency of about 0.1×10$^9$ CFU/dose to about 1.5×10$^9$ CFU/dose. In embodiments, the *Clostridium butyricum* is administered once daily with a potency of about 0.1×10$^9$ CFU/dose to about 1.0×10$^9$ CFU/dose.

In embodiments, the *Clostridium butyricum* is administered once daily with a potency of about 0.1×10$^9$ CFU/dose, 0.5×10$^9$ CFU/dose, 1.5×10$^9$ CFU/dose, 2.0×10$^9$ CFU/dose, 2.5×10$^9$ CFU/dose, 3.0×10$^9$ CFU/dose, 3.5×10$^9$ CFU/dose, 4.0×10$^9$ CFU/dose, 4.5×10$^9$ CFU/dose, 5.0×10$^9$ CFU/dose, 5.5×10$^9$ CFU/dose, 6.0×10$^9$ CFU/dose, 6.5×10$^9$ CFU/dose, 7.0×10$^9$ CFU/dose, 7.5×10$^9$ CFU/dose, 8.0×10$^9$ CFU/dose, 8.5×10$^9$ CFU/dose, 9.0×10$^9$ CFU/dose, 9.5×10$^9$ CFU/dose or 10×10$^9$ CFU/dose. In embodiments, the *Clostridium butyricum* is administered once daily with a potency of about 2.5×10$^9$ CFU/dose. In embodiments, the *Clostridium butyricum* is administered once daily with a potency of 2.5×10$^9$ CFU/dose. In embodiments, the *Clostridium butyricum* is administered once daily with a potency of about 5.0×10$^9$ CFU/dose. In embodiments, the *Clostridium butyricum* is administered once daily with a potency of 5.0×10$^9$ CFU/dose. The potency of CBM588 LBP may be any value or subrange within the recited ranges, including endpoints, or any range between any of the recited values.

In embodiments, the *Clostridium butyricum* is administered twice daily with a potency of about 0.1×10$^9$ CFU/dose to about 10×10$^9$ CFU/dose. In embodiments, the *Clostridium butyricum* is administered twice daily with a potency of about 0.5×10$^9$ CFU/dose to about 10×10$^9$ CFU/dose. In embodiments, the *Clostridium butyricum* is administered twice daily with a potency of about 1.0×10$^9$ CFU/dose to about 10×10$^9$ CFU/dose. In embodiments, the *Clostridium butyricum* is administered twice daily with a potency of about 1.5×10$^9$ CFU/dose to about 10×10$^9$ CFU/dose. In embodiments, the *Clostridium butyricum* is administered twice daily with a potency of about 2.0×10$^9$ CFU/dose to about 10×10$^9$ CFU/dose. In embodiments, the *Clostridium butyricum* is administered twice daily with a potency of about 2.5×10$^9$ CFU/dose to about 10×10$^9$ CFU/dose. In embodiments, the *Clostridium butyricum* is administered twice daily with a potency of about 3.0×10$^9$ CFU/dose to about 10×10$^9$ CFU/dose. In embodiments, the *Clostridium butyricum* is administered twice daily with a potency of about 3.5×10$^9$ CFU/dose to about 10×10$^9$ CFU/dose. In embodiments, the *Clostridium butyricum* is administered twice daily with a potency of about 4.0×10$^9$ CFU/dose to about 10×10$^9$ CFU/dose. In embodiments, the *Clostridium butyricum* is administered twice daily with a potency of about 4.5×10$^9$ CFU/dose to about 10×10$^9$ CFU/dose. In embodiments, the *Clostridium butyricum* is administered twice daily with a potency of about 5.0×10$^9$ CFU/dose to about 10×10$^9$ CFU/dose. In embodiments, the *Clostridium butyricum* is administered twice daily with a potency of about 5.5×10$^9$ CFU/dose to about 10×10$^9$ CFU/dose. In embodiments, the *Clostridium butyricum* is administered twice daily with a potency of about 6.0×10$^9$ CFU/dose to about 10×10$^9$ CFU/dose. In embodiments, the *Clostridium butyricum* is administered twice daily with a potency of about 6.5×10$^9$ CFU/dose to about 10×10$^9$ CFU/dose. In embodiments, the *Clostridium butyricum* is administered twice daily with a potency of about 7.0×10$^9$ CFU/dose to about 10×10$^9$ CFU/dose. In embodiments, the *Clostridium butyricum* is administered twice daily with a potency of about 7.5×10$^9$ CFU/dose to about 10×10$^9$ CFU/dose. In embodiments, the *Clostridium butyricum* is administered twice daily with a potency of about 8.0×10$^9$ CFU/dose to about 10×10$^9$ CFU/dose. In embodiments, the *Clostridium butyricum* is administered twice daily with a potency of about 8.5×10$^9$ CFU/dose to about 10×10$^9$ CFU/dose. In embodiments, the *Clostridium butyricum* is administered twice daily with a potency of about 9.0×10$^9$ CFU/dose to about 10×10$^9$ CFU/dose.

In embodiments, the *Clostridium butyricum* is administered twice daily with a potency of about 0.1×10$^9$ CFU/dose to about 9.5×10$^9$ CFU/dose. In embodiments, the *Clostridium butyricum* is administered twice daily with a potency of about 0.1×10$^9$ CFU/dose to about 9.0×10$^9$ CFU/dose. In embodiments, the *Clostridium butyricum* is administered twice daily with a potency of about 0.1×10$^9$ CFU/dose to about 8.5×10$^9$ CFU/dose. In embodiments, the *Clostridium butyricum* is administered twice daily with a potency of about 0.1×10$^9$ CFU/dose to about 8.0×10$^9$ CFU/dose. In embodiments, the *Clostridium butyricum* is administered twice daily with a potency of about 0.1×10$^9$ CFU/dose to about 7.5×10$^9$ CFU/dose. In embodiments, the *Clostridium butyricum* is administered twice daily with a potency of about 0.1×10$^9$ CFU/dose to about 7.0×10$^9$ CFU/dose. In embodiments, the *Clostridium butyricum* is administered twice daily with a potency of about $0.1\times10^9$ CFU/dose to about $6.5\times10^9$ CFU/dose. In embodiments, the *Clostridium butyricum* is administered twice daily with a potency of about $0.1\times10^9$ CFU/dose to about $6.0\times10^9$ CFU/dose. In embodiments, the *Clostridium butyricum* is administered twice daily with a potency of about $0.1\times10^9$ CFU/dose to about $5.5\times10^9$ CFU/dose. In embodiments, the *Clostridium butyricum* is administered twice daily with a potency of about $0.1\times10^9$ CFU/dose to about $5.0\times10^9$ CFU/dose. In embodiments, the *Clostridium butyricum* is administered twice daily with a potency of about $0.1\times10^9$ CFU/dose to about $4.5\times10^9$ CFU/dose. In embodiments, the *Clostridium butyricum* is administered twice daily with a potency of about $0.1\times10^9$ CFU/dose to about $4.0\times10^9$ CFU/dose. In embodiments, the *Clostridium butyricum* is administered twice daily with a potency of about $0.1\times10^9$ CFU/dose to about $3.5\times10^9$ CFU/dose. In embodiments, the *Clostridium butyricum* is administered twice daily with a potency of about $0.1\times10^9$ CFU/dose to about $3.0\times10^9$ CFU/dose. In embodiments, the *Clostridium butyricum* is administered twice daily with a potency of about $0.1\times10^9$ CFU/dose to about $2.5\times10^9$ CFU/dose. In embodiments, the *Clostridium butyricum* is administered twice daily with a potency of about $0.1\times10^9$ CFU/dose to about $2.0\times10^9$ CFU/dose. In embodiments, the *Clostridium butyricum* is administered twice daily with a potency of about $0.1\times10^9$ CFU/dose to about $1.5\times10^9$ CFU/dose. In embodiments, the *Clostridium butyricum* is administered twice daily with a potency of about $0.1\times10^9$ CFU/dose to about $1.0\times10^9$ CFU/dose.

In embodiments, the *Clostridium butyricum* is administered twice daily with a potency of about $0.1\times10^9$ CFU/dose, $0.5\times10^9$ CFU/dose, $1.5\times10^9$ CFU/dose, $2.0\times10^9$ CFU/dose, $2.5\times10^9$ CFU/dose, $3.0\times10^9$ CFU/dose, $3.5\times10^9$ CFU/dose, $4.0\times10^9$ CFU/dose, $4.5\times10^9$ CFU/dose, $5.0\times10^9$ CFU/dose, $5.5\times10^9$ CFU/dose, $6.0\times10^9$ CFU/dose, $6.5\times10^9$ CFU/dose, $7.0\times10^9$ CFU/dose, $7.5\times10^9$ CFU/dose, $8.0\times10^9$ CFU/dose, $8.5\times10^9$ CFU/dose, $9.0\times10^9$ CFU/dose, $9.5\times10^9$ CFU/dose, or about $10\times10^9$ CFU/dose. In embodiments, the *Clostridium butyricum* is administered twice daily with a potency of about $2.5\times10^9$ CFU/dose. In embodiments, the *Clostridium butyricum* is administered twice daily with a potency of $2.5\times10^9$ CFU/dose. In embodiments, the *Clostridium butyricum* is administered twice daily with a potency of about $5.0\times10^9$ CFU/dose. In embodiments, the *Clostridium butyricum* is administered twice daily with a potency of $5.0\times10^9$ CFU/dose. The potency of *Clostridium butyricum* may be any value or subrange within the recited ranges, including endpoints, or any range between any of the recited values.

In embodiments, the *Clostridium butyricum* is administered three times daily with a potency of about $0.1\times10^9$ CFU/dose to about $10\times10^9$ CFU/dose. In embodiments, the *Clostridium butyricum* is administered three times daily with a potency of about $0.5\times10^9$ CFU/dose to about $10\times10^9$ CFU/dose. In embodiments, the *Clostridium butyricum* is administered three times daily with a potency of about $1.0\times10^9$ CFU/dose to about $10\times10^9$ CFU/dose. In embodiments, the *Clostridium butyricum* is administered three times daily with a potency of about $1.5\times10^9$ CFU/dose to about $10\times10^9$ CFU/dose. In embodiments, the *Clostridium butyricum* is administered three times daily with a potency of about $2.0\times10^9$ CFU/dose to about $10\times10^9$ CFU/dose. In embodiments, the *Clostridium butyricum* is administered three times daily with a potency of about $2.5\times10^9$ CFU/dose to about $10\times10^9$ CFU/dose. In embodiments, the *Clostridium butyricum* is administered three times daily with a potency of about $3.0\times10^9$ CFU/dose to about $10\times10^9$ CFU/dose. In embodiments, the *Clostridium butyricum* is administered three times daily with a potency of about $3.5\times10^9$ CFU/dose to about $10\times10^9$ CFU/dose. In embodiments, the *Clostridium butyricum* is administered three times daily with a potency of about $4.0\times10^9$ CFU/dose to about $10\times10^9$ CFU/dose. In embodiments, the *Clostridium butyricum* is administered three times daily with a potency of about $4.5\times10^9$ CFU/dose to about $10\times10^9$ CFU/dose. In embodiments, the *Clostridium butyricum* is administered three times daily with a potency of about $5.0\times10^9$ CFU/dose to about $10\times10^9$ CFU/dose. In embodiments, the *Clostridium butyricum* is administered three times daily with a potency of about $5.5\times10^9$ CFU/dose to about $10\times10^9$ CFU/dose. In embodiments, the *Clostridium butyricum* is administered three times daily with a potency of about $6.0\times10^9$ CFU/dose to about $10\times10^9$ CFU/dose. In embodiments, the *Clostridium butyricum* is administered three times daily with a potency of about $6.5\times10^9$ CFU/dose to about $10\times10^9$ CFU/dose. In embodiments, the *Clostridium butyricum* is administered three times daily with a potency of about $7.0\times10^9$ CFU/dose to about $10\times10^9$ CFU/dose. In embodiments, the *Clostridium butyricum* is administered three times daily with a potency of about $7.5\times10^9$ CFU/dose to about $10\times10^9$ CFU/dose. In embodiments, the *Clostridium butyricum* is administered three times daily with a potency of about $8.0\times10^9$ CFU/dose to about $10\times10^9$ CFU/dose. In embodiments, the *Clostridium butyricum* is administered three times daily with a potency of about $8.5\times10^9$ CFU/dose to about $10\times10^9$ CFU/dose. In embodiments, the *Clostridium butyricum* is administered three times daily with a potency of about $9.0\times10^9$ CFU/dose to about $10\times10^9$ CFU/dose.

In embodiments, the *Clostridium butyricum* is administered three times daily with a potency of about $0.1\times10^9$ CFU/dose to about $9.5\times10^9$ CFU/dose. In embodiments, the *Clostridium butyricum* is administered three times daily with a potency of about $0.1\times10^9$ CFU/dose to about $9.0\times10^9$ CFU/dose. In embodiments, the *Clostridium butyricum* is administered three times daily with a potency of about $0.1\times10^9$ CFU/dose to about $8.5\times10^9$ CFU/dose. In embodiments, the *Clostridium butyricum* is administered three times daily with a potency of about $0.1\times10^9$ CFU/dose to about $8.0\times10^9$ CFU/dose. In embodiments, the *Clostridium butyricum* is administered three times daily with a potency of about $0.1\times10^9$ CFU/dose to about $7.5\times10^9$ CFU/dose. In embodiments, the *Clostridium butyricum* is administered three times daily with a potency of about $0.1\times10^9$ CFU/dose to about $7.0\times10^9$ CFU/dose. In embodiments, the *Clostridium butyricum* is administered three times daily with a potency of about $0.1\times10^9$ CFU/dose to about $6.5\times10^9$ CFU/dose. In embodiments, the *Clostridium butyricum* is administered three times daily with a potency of about $0.1\times10^9$ CFU/dose to about $6.0\times10^9$ CFU/dose. In embodiments, the *Clostridium butyricum* is administered three times daily with a potency of about $0.1\times10^9$ CFU/dose to about $5.5\times10^9$ CFU/dose. In embodiments, the *Clostridium butyricum* is administered three times daily with a potency of about $0.1\times10^9$ CFU/dose to about $5.0\times10^9$ CFU/dose. In embodiments, the *Clostridium butyricum* is administered three times daily with a potency of about $0.1\times10^9$ CFU/dose to about $4.5\times10^9$ CFU/dose. In embodiments, the *Clostridium butyricum* is administered three times daily with a potency of about $0.1\times10^9$ CFU/dose to about $4.0\times10^9$ CFU/dose. In embodiments, the *Clostridium butyricum* is administered three times daily with a potency of about $0.1\times10^9$ CFU/dose to about $3.5\times10^9$ CFU/dose. In embodiments, the *Clostridium butyricum* is administered three times daily with a potency of about $0.1\times10^9$ CFU/dose to about $3.0\times10^9$ CFU/dose. In embodiments, the *Clostridium butyricum* is administered three times daily with a potency of about $0.1\times10^9$ CFU/dose to about $2.5\times10^9$ CFU/dose. In embodiments, the *Clostridium butyricum* is administered three times daily with a potency of about $0.1\times10^9$ CFU/dose to about $2.0\times10^9$ CFU/dose. In embodiments, the *Clostridium butyricum* is administered three times daily with a potency of about $0.1\times10^9$ CFU/dose to about $1.5\times10^9$ CFU/dose. In embodiments, the *Clostridium butyricum* is administered three times daily with a potency of about $0.1\times10^9$ CFU/dose to about $1.0\times10^9$ CFU/dose.

In embodiments, the *Clostridium butyricum* is administered three times daily with a potency of about $0.1\times10^9$ CFU/dose, $0.5\times10^9$ CFU/dose, $1.5\times10^9$ CFU/dose, $2.0\times10^9$ CFU/dose, $2.5\times10^9$ CFU/dose, $3.0\times10^9$ CFU/dose, $3.5\times10^9$ CFU/dose, $4.0\times10^9$ CFU/dose, $4.5\times10^9$ CFU/dose, $5.0\times10^9$ CFU/dose, $5.5\times10^9$ CFU/dose, $6.0\times10^9$ CFU/dose, $6.5\times10^9$ CFU/dose, $7.0\times10^9$ CFU/dose, $7.5\times10^9$ CFU/dose, $8.0\times10^9$ CFU/dose, $8.5\times10^9$ CFU/dose, $9.0\times10^9$ CFU/dose, $9.5\times10^9$ CFU/dose or about $10\times10^9$ CFU/dose. In embodiments, the *Clostridium butyricum* is administered three times daily with a potency of about $2.5\times10^9$ CFU/dose. In embodiments, the *Clostridium butyricum* is administered three times daily with a potency of $2.5\times10^9$ CFU/dose. In embodiments, the *Clostridium butyricum* is administered three times daily with a potency of about $5.0\times10^9$ CFU/dose. In embodiments, the *Clostridium butyricum* is administered three times daily with a potency of $5.0\times10^9$ CFU/dose. The potency of CBM588 LBP may be any value or subrange within the recited ranges, including endpoints, or any range between any of the recited values.

In embodiments, the *Clostridium butyricum* may be administered at about $5\times10^9$ CFU/dose. In embodiments, the *Clostridium butyricum* may be administered at $5\times10^9$ CFU/dose. In embodiments, the $5\times10^9$ CFU/dose of CBM588 LBP may be administered twice daily.

In embodiments, ipilimumab may be administered at a dose of about 0.25 mg/kg to about 5 mg/kg. In embodiments, ipilimumab may be administered at a dose of about 0.5 mg/kg to about 5 mg/kg. In embodiments, ipilimumab may be administered at a dose of about 0.75 mg/kg to about 5 mg/kg. In embodiments, ipilimumab may be administered at a dose of about 1 mg/kg to about 5 mg/kg. In embodiments, ipilimumab may be administered at a dose of about 1.25 mg/kg to about 5 mg/kg. In embodiments, ipilimumab may be administered at a dose of about 1.5 mg/kg to about 5 mg/kg. In embodiments, ipilimumab may be administered at a dose of about 1.75 mg/kg to about 5 mg/kg. In embodiments, ipilimumab may be administered at a dose of about 2 mg/kg to about 5 mg/kg. In embodiments, ipilimumab may be administered at a dose of about 2.25 mg/kg to about 5 mg/kg. In embodiments, ipilimumab may be administered at a dose of about 2.5 mg/kg to about 5 mg/kg. In embodiments, ipilimumab may be administered at a dose of about 2.75 mg/kg to about 5 mg/kg. In embodiments, ipilimumab may be administered at a dose of about 3.0 mg/kg to about 5 mg/kg. In embodiments, ipilimumab may be administered at a dose of about 3.25 mg/kg to about 5 mg/kg. In embodiments, ipilimumab may be administered at a dose of about 3.75 mg/kg to about 5 mg/kg. In embodiments, ipilimumab may be administered at a dose of about 4 mg/kg to about 5 mg/kg. In embodiments, ipilimumab may be administered at a dose of about 4.25 mg/kg to about 5 mg/kg. In embodiments, ipilimumab may be administered at a dose of about 4.5 mg/kg to about 5 mg/kg.

In embodiments, ipilimumab may be administered at a dose of about 0.25 mg/kg to about 4.5 mg/kg. In embodiments, ipilimumab may be administered at a dose of about 0.25 mg/kg to about 4.25 mg/kg. In embodiments, ipilimumab may be administered at a dose of about 0.25 mg/kg to about 4 mg/kg. In embodiments, ipilimumab may be administered at a dose of about 0.25 mg/kg to about 3.75 mg/kg. In embodiments, ipilimumab may be administered at a dose of about 0.25 mg/kg to about 3.25 mg/kg. In embodiments, ipilimumab may be administered at a dose of about 0.25 mg/kg to about 3 mg/kg. In embodiments, ipilimumab may be administered at a dose of about 0.25 mg/kg to about 2.75 mg/kg. In embodiments, ipilimumab may be administered at a dose of about 0.25 mg/kg to about 2.5 mg/kg. In embodiments, ipilimumab may be administered at a dose of about 0.25 mg/kg to about 2.25 mg/kg. In embodiments, ipilimumab may be administered at a dose of about 0.25 mg/kg to about 2 mg/kg. In embodiments, ipilimumab may be administered at a dose of about 0.25 mg/kg to about 1.75 mg/kg. In embodiments, ipilimumab may be administered at a dose of about 0.25 mg/kg to about 1.5 mg/kg. In embodiments, ipilimumab may be administered at a dose of about 0.25 mg/kg to about 1.25 mg/kg. In embodiments, ipilimumab may be administered at a dose of about 0.25 mg/kg to about 1 mg/kg. In embodiments, ipilimumab may be administered at a dose of about 0.25 mg/kg to about 0.75 mg/kg.

In embodiments, ipilimumab may be administered at a dose of 0.25 mg/kg, 0.5 mg/kg, 0.75 mg/kg, 1 mg/kg, 1.25 mg/kg, 1.5 mg/kg, 1.75 mg/kg, 2 mg/kg, 2.25 mg/kg, 2.5 mg/kg, 2.75 mg/kg, 3 mg/kg, 4.25 mg/kg, 4.5 mg/kg, 4.75 mg/kg, or 5 mg/kg. In embodiments, ipilimumab may be administered at a dose of about 1 mg/kg. In embodiments, ipilimumab may be administered at a dose of 1 mg/kg. The dosage of ipilimumab may be any value or subrange within the recited ranges, including endpoints, or any range between any of the recited values.

In embodiments, nivolumab may be administered at a dose of about 0.5 mg/kg to about 6 mg/kg. In embodiments, nivolumab may be administered at a dose of about 1 mg/kg to about 6 mg/kg. In embodiments, nivolumab may be administered at a dose of about 1.5 mg/kg to about 6 mg/kg. In embodiments, nivolumab may be administered at a dose of about 2 mg/kg to about 6 mg/kg. In embodiments, nivolumab may be administered at a dose of about 2.5 mg/kg to about 6 mg/kg. In embodiments, nivolumab may be administered at a dose of about 3 mg/kg to about 6 mg/kg. In embodiments, nivolumab may be administered at a dose of about 3.5 mg/kg to about 6 mg/kg. In embodiments, nivolumab may be administered at a dose of about 4 mg/kg to about 6 mg/kg. In embodiments, nivolumab may be administered at a dose of about 4.5 mg/kg to about 6 mg/kg. In embodiments, nivolumab may be administered at a dose of about 5 mg/kg to about 6 mg/kg.

In embodiments, nivolumab may be administered at a dose of about 0.5 mg/kg to about 5.5 mg/kg. In embodiments, nivolumab may be administered at a dose of about 0.5 mg/kg to about 4.5 mg/kg. In embodiments, nivolumab may be administered at a dose of about 0.5 mg/kg to about 4 mg/kg. In embodiments, nivolumab may be administered at a dose of about 0.5 mg/kg to about 3.5 mg/kg. In embodiments, nivolumab may be administered at a dose of about 0.5 mg/kg to about 3 mg/kg. In embodiments, nivolumab may be administered at a dose of about 0.5 mg/kg to about 2.5 mg/kg. In embodiments, nivolumab may be administered at a dose of about 0.5 mg/kg to about 2 mg/kg. In embodiments, nivolumab may be administered at a dose of about 0.5 mg/kg to about 1.5 mg/kg.

In embodiments, nivolumab may be administered at a dose of about 0.5 mg/kg, about 1 mg/kg, about 1.5 mg/kg, about 2 mg/kg, about 2.5 mg/kg, about 3 mg/kg, about 3.5 mg/kg, about 4 mg/kg, about 4.5 mg/kg, about 5 mg/kg, about 5.5 mg/kg, or about 6 mg/kg. In embodiments, nivolumab may be administered at a dose of about 3 mg/kg. The dosage of nivolumab may be any value or subrange within the recited ranges, including endpoints, or any range between any of the recited values.

In embodiments, nivolumab may be administered once every three weeks, wherein the three weeks is referred to as a "cycle". Nivolumab may be administered for about 1 cycle to about 10 cycles. Nivolumab may be administered for about 1 cycle, about 2 cycles, about 3 cycles, about 4 cycles, about 5 cycles, about 6 cycles, about 7 cycles, about 8 cycles, about 9 cycles, or about 10 cycles.

In embodiments, ipilimumab may be administered once every three weeks, wherein the three weeks is referred to as a "cycle". Ipilimumab may be administered for about 1 cycle to about 10 cycles. Ipilimumab may be administered for about 1 cycle, about 2 cycles, about 3 cycles, about 4 cycles, about 5 cycles, about 6 cycles, about 7 cycles, about 8 cycles, about 9 cycles, or about 10 cycles.

For the pharmaceutical composition provided herein, including embodiments thereof, the anti-cancer agent may be used in an amount typically considered to be a sub-therapeutic amount, but is a therapeutically effective amount with used in combination with *Clostridium butyricum*. In embodiments, the anti-cancer agent is one or more checkpoint inhibitors. Thus, in embodiments, the checkpoint inhibitor may be used in an amount typically considered to be a sub-therapeutic amount, but is a therapeutically effective amount with used in combination with *Clostridium butyricum*. In embodiments, the checkpoint inhibitor is nivolumab, ipilimumab, pembrolizumab, cemiplimab, durvalumab, daclizumab, avelumab, or atezolizumab. In embodiments, the checkpoint inhibitor is pembrolizumab. In embodiments, the checkpoint inhibitor is cemiplimab. In embodiments, the checkpoint inhibitor is durvalumab. In embodiments, the checkpoint inhibitor is daclizumab. In embodiments, the checkpoint inhibitor is avelumab. In embodiments, the checkpoint inhibitor is atezolizumab. In embodiments, the checkpoint inhibitor is nivolumab or ipilimumab. In embodiments the checkpoint inhibitor is nivolumab. In embodiments the checkpoint inhibitor is ipilimumab. In embodiments the checkpoint inhibitor is a combination of one or more of nivolumab, ipilimumab, pembrolizumab, talimogene laherparepvec, durvalumab, daclizumab, avelumab, or atezolizumab.

In embodiments, ipilimumab may be used in an amount typically considered to be a sub-therapeutic amount, but is a therapeutically effective amount with used in combination with *Clostridium butyricum*. In embodiments, nivolumab may be used in an amount typically considered to be a sub-therapeutic amount, but is a therapeutically effective amount with used in combination with *Clostridium butyricum*. In embodiments, nivolumab and ipilimumab may be used in amounts typically considered to be sub-therapeutic amounts, but are therapeutically effective amounts with used in combination with CBM588 LBP. In embodiments, when used in combination with *Clostridium butyricum* nivolumab is therapeutically effective in amounts typically considered to be sub-therapeutic amounts. In embodiments, when used in combination with *Clostridium butyricum* ipilimumab is therapeutically effective in amounts typically considered to be sub-therapeutic amounts. In embodiments, when used in combination with *Clostridium butyricum* nivolumab and ipilimumab are therapeutically effective in amounts typically considered to be sub-therapeutic amounts.

In embodiments, pembrolizumab may be used in an amount typically considered to be a sub-therapeutic amount, but is a therapeutically effective amount with used in combination with *Clostridium butyricum*. In embodiments, when used in combination with *Clostridium butyricum* pembrolizumab is therapeutically effective in amounts typically considered to be sub-therapeutic amounts. In embodiments, cemiplimab may be used in an amount typically considered to be a sub-therapeutic amount, but is a therapeutically effective amount with used in combination with *Clostridium butyricum*. In embodiments, when used in combination with *Clostridium butyricum* cemiplimab is therapeutically effective in amounts typically considered to be sub-therapeutic amounts. In embodiments, durvalumab may be used in an amount typically considered to be a sub-therapeutic amount, but is a therapeutically effective amount with used in combination with *Clostridium butyricum*. In embodiments, when used in combination with *Clostridium butyricum* durvalumab is therapeutically effective in amounts typically considered to be sub-therapeutic amounts. In embodiments, daclizumab may be used in an amount typically considered to be a sub-therapeutic amount, but is a therapeutically effective amount with used in combination with *Clostridium butyricum*. In embodiments, when used in combination with *Clostridium butyricum* daclizumab is therapeutically effective in amounts typically considered to be sub-therapeutic amounts. In embodiments, avelumab may be used in an amount typically considered to be a sub-therapeutic amount, but is a therapeutically effective amount with used in combination with *Clostridium butyricum*. In embodiments, when used in combination with *Clostridium butyricum* avelumab is therapeutically effective in amounts typically considered to be sub-therapeutic amounts. In embodiments, atezolizumab may be used in an amount typically considered to be a sub-therapeutic amount, but is a therapeutically effective amount with used in combination with *Clostridium butyricum*. In embodiments, when used in combination with *Clostridium butyricum* atezolizumab is therapeutically effective in amounts typically considered to be sub-therapeutic amounts.

In embodiments, ipilimumab may be used in an amount typically considered to be a sub-therapeutic amount, but is a therapeutically effective amount with used in combination with *Clostridium butyricum*. In embodiments, the amount may be about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% of the amount of ipilimumab when used separately from *Clostridium butyricum*. In embodiments, the therapeutically effective amount of ipilimumab may be about 0.1 mg/kg to about 2.2 mg/kg.

Thus, in embodiments, ipilimumab may be administered at a dose of about 0.1 mg/kg to about 2.2 mg/kg. In embodiments, ipilimumab may be administered at a dose of about 0.4 mg/kg to about 2.2 mg/kg. In embodiments, ipilimumab may be administered at a dose of about 0.7 mg/kg to about 2.2 mg/kg. In embodiments, ipilimumab may be administered at a dose of about 1 mg/kg to about 2.2 mg/kg. In embodiments, ipilimumab may be administered at a dose of about 1.3 mg/kg to about 2.2 mg/kg. In embodiments, ipilimumab may be administered at a dose of about 1.6 mg/kg to about 2.2 mg/kg.

In embodiments, ipilimumab may be administered at a dose of about 0.1 mg/kg to about 1.9 mg/kg. In embodiments, ipilimumab may be administered at a dose of about 0.1 mg/kg to about 1.6 mg/kg. In embodiments, ipilimumab may be administered at a dose of about 0.1 mg/kg to about 1.3 mg/kg. In embodiments, ipilimumab may be administered at a dose of about 0.1 mg/kg to about 1 mg/kg. In embodiments, ipilimumab may be administered at a dose of about 0.1 mg/kg to about 0.7 mg/kg.

In embodiments, ipilimumab may be administered at a dose of about 0.1 mg/kg, 0.4 mg/kg, 0.7 mg/kg, 1 mg/kg, 1.3 mg/kg, 1.6 mg/kg, 1.9 mg/kg, or 2.2 mg/kg. The dosage of ipilimumab may be any value or subrange within the recited ranges, including endpoints, or any range between any of the recited values.

In embodiments, nivolumab may be used in an amount typically considered to be a sub-therapeutic amount, but is a therapeutically effective amount with used in combination with *Clostridium butyricum*. In embodiments, the amount may be about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% of the amount of nivolumab when used separately from *Clostridium butyricum*. Thus, the therapeutically effective amount of nivolumab may be about 0.2 mg/kg to about 2 mg/kg.

Thus, in embodiments, nivolumab may be administered at a dose of about 0.2 mg/kg to about 2 mg/kg. In embodiments, nivolumab may be administered at a dose of about 0.4 mg/kg to about 2 mg/kg. In embodiments, nivolumab may be administered at a dose of about 0.6 mg/kg to about 2 mg/kg. In embodiments, nivolumab may be administered at a dose of about 0.8 mg/kg to about 2 mg/kg. In embodiments, nivolumab may be administered at a dose of about 1 mg/kg to about 2 mg/kg. In embodiments, nivolumab may be administered at a dose of about 1.2 mg/kg to about 2 mg/kg. In embodiments, nivolumab may be administered at a dose of about 1.4 mg/kg to about 2 mg/kg. In embodiments, nivolumab may be administered at a dose of about 1.6 mg/kg to about 2 mg/kg.

In embodiments, nivolumab may be administered at a dose of about 0.2 mg/kg to about 1.8 mg/kg. In embodiments, nivolumab may be administered at a dose of about 0.2 mg/kg to about 1.6 mg/kg. In embodiments, nivolumab may be administered at a dose of about 0.2 mg/kg to about 1.4 mg/kg. In embodiments, nivolumab may be administered at a dose of about 0.2 mg/kg to about 1.2 mg/kg. In embodiments, nivolumab may be administered at a dose of about 0.2 mg/kg to about 1 mg/kg. In embodiments, nivolumab may be administered at a dose of about 0.2 mg/kg to about 0.8 mg/kg. In embodiments, nivolumab may be administered at a dose of about 0.2 mg/kg to about 0.6 mg/kg.

In embodiments, nivolumab may be administered at a dose of about 0.2 mg/kg, 0.4 mg/kg, 0.8 mg/kg, 1 mg/kg, 1.2 mg/kg, 1.4 mg/kg, 1.6 mg/kg, 1.8 mg/kg, or 2 mg/kg. The dosage of nivolumab may be any value or subrange within the recited ranges, including endpoints, or any range between any of the recited values.

Kits

The pharmaceutical compositions provided herein, including embodiments thereof may be packaged in a kit for the treatment of cancer. Thus, in an aspect is provided a kit including: (a) a first pharmaceutical composition including an anticancer agent in a first dosage form and a pharmaceutically acceptable excipient in a suitable container or with suitable packaging; and (b) a second pharmaceutical composition including *Clostridium butyricum* in a second dosage form in a suitable container or with suitable packaging. In embodiments, the *Clostridium butyricum* is a live biotherapeutic product. In embodiments, the *Clostridium butyricum* live biotherapeutic product is *Clostridium butyricum* MIYAIRI 588 live biotherapeutic product (CBM588 LBP). As used herein, the term "dosage form" refers to a formulation that includes a predetermined dose of an agent (e.g. anti-cancer agent, *Clostridium butyricum*). The agent (e.g. anti-cancer agent, *Clostridium butyricum*) of the dosage form is present in an amount effective to treat the disease for which it is prescribed. In embodiments, the kit includes instructions for use. In embodiments, the kit includes (a) the first dosage form and the second dosage form; and (b) instructions for use of in the treatment, prevention, slowing the progression or delaying the onset and/or development of cancer or the recurrence of cancer.

In embodiments, the anti-cancer agent is a checkpoint inhibitor. In embodiments, the checkpoint inhibitor is a PD-1, PD-L1 or CTLA-4 inhibitor. In embodiments, the checkpoint inhibitor is a PD-1 inhibitor. In embodiments, the checkpoint inhibitor is a PD-L1 inhibitor. In embodiments, the checkpoint inhibitor is a CTLA-4 inhibitor. In embodiments, the checkpoint inhibitor is nivolumab, ipilimumab, pembrolizumab, cemiplimab, durvalumab, daclizumab, avelumab, or atezolizumab. In embodiments, the checkpoint inhibitor is pembrolizumab. In embodiments, the checkpoint inhibitor is cemiplimab. In embodiments, the checkpoint inhibitor is durvalumab. In embodiments, the checkpoint inhibitor is daclizumab. In embodiments, the checkpoint inhibitor is avelumab. In embodiments, the checkpoint inhibitor is atezolizumab. In embodiments the checkpoint inhibitor is nivolumab. In embodiments the checkpoint inhibitor is ipilimumab. In embodiments the checkpoint inhibitor is nivolumab or ipilimumab.

In embodiments, the kit further includes (c) a third pharmaceutical composition including a second anti-cancer agent and a pharmaceutically acceptable excipient in a suitable container or with suitable packaging. In embodiments, the second anti-cancer agent is a second checkpoint inhibitor. In embodiments, the second checkpoint inhibitor is a PD-1, PD-L1 or CTLA-4 inhibitor. In embodiments, the second checkpoint inhibitor is a PD-1 inhibitor. In embodiments, the second checkpoint inhibitor is a PD-L1 inhibitor. In embodiments, the second checkpoint inhibitor is a CTLA-4 inhibitor. In embodiments, the second checkpoint inhibitor is nivolumab, ipilimumab, pembrolizumab, cemiplimab, durvalumab, daclizumab, avelumab, or atezolizumab. In embodiments, the second checkpoint inhibitor is pembrolizumab. In embodiments, the second checkpoint inhibitor is cemiplimab. In embodiments, the second checkpoint inhibitor is durvalumab. In embodiments, the second checkpoint inhibitor is daclizumab. In embodiments, the second checkpoint inhibitor is avelumab. In embodiments, the second checkpoint inhibitor is atezolizumab. In embodiments, the second checkpoint inhibitor is nivolumab or ipilimumab. In embodiments the second checkpoint inhibitor is nivolumab. In embodiments the second checkpoint inhibitor is ipilimumab.

Thus, in an aspect is provided a kit including: (a) a first pharmaceutical composition including an anticancer agent in a first dosage form and a pharmaceutically acceptable excipient in a suitable container or with suitable packaging; and (b) a second pharmaceutical composition including a *Clostridium butyricum* MIYAIRI 588 live biotherapeutic product (CBM588 LBP) preparation in a second dosage form in a suitable container or with suitable packaging. In embodiments, the CBM588 LBP is CBM588 in combination with another strain of *Clostridium butyricum*, a strain from the genus *Bifidobacterium*, a strain from the genus *Dorea*, a strain from the genus *Blautia*, or *Akkermansia municiphila*. In embodiments, the CBM588 LBP is CBM588 with another strain of *Clostridium butyricum*. In embodiments, the CBM588 LBP is CBM588 with a strain from the genus *Bifidobacterium*. In embodiments, the CBM588 LBP is CBM588 with a strain from the genus *Dorea*. In embodiments, the CBM588 LBP is CBM588 with a strain from the genus *Blautia*. In embodiments, the CBM588 LBP is CBM588 with *Akkermansia municiphila*. In embodiments the CBM388 LBP is a combination CBM388 with of one or more of other bacterial species, including but not limited to one or more other strains of *Clostridium butyricum*, one or more strains from the genus *Bifidobacterium*, one or more strains from the genus *Dorea*, one or more strains from the genus *Blautia*, and/or *Akkermansia municiphila*.

P Embodiments

P Embodiment 1. A method for treating cancer in a subject in need thereof, said method comprising administering to said subject an effective amount of an anti-cancer agent and *Clostridium butyricum* MIYAIRI 588 live biotherapeutic product (CBM588 LBP).

P Embodiment 2. The method of P embodiment 1, wherein the anti-cancer agent is a checkpoint inhibitor.

P Embodiment 3. The method of P embodiment 2, wherein the checkpoint inhibitor is a PD-1, PDL-1 or CTLA-4 inhibitor.

P Embodiment 4. The method of P embodiment 2 or 3, wherein said checkpoint inhibitor is nivolumab, ipilimumab, pembrolizumab, cemiplimab, durvalumab, daclizumab, avelumab, or atezolizumab.

P Embodiment 5. The method of any one of P embodiments 2 to 4, wherein said checkpoint inhibitor is nivolumab.

P Embodiment 6. The method of any one of P embodiments 2 to 4, wherein said checkpoint inhibitor is ipilimumab.

P Embodiment 7. The method of any one of P embodiments 1 to 6, further comprising a second anticancer agent.

P Embodiment 8. The method of P embodiment 7, wherein the second anti-cancer agent is a second checkpoint inhibitor.

P Embodiment 9. The method of P embodiment 8, wherein the second checkpoint inhibitor is nivolumab, ipilimumab, pembrolizumab, cemiplimab, durvalumab, daclizumab, avelumab, or atezolizumab.

P Embodiment 10. The method of P embodiment 8 or 9, wherein the second checkpoint inhibitor is nivolumab.

P Embodiment 11. The method of P embodiment 8 or 9, wherein the second checkpoint inhibitor is ipilimumab.

P Embodiment 12. The method of any one of P embodiments 1 to 11, wherein said cancer is a microsatellite-instability high (MSI-H) cancer.

P Embodiment 13. The method of any one of P embodiments 1 to 12, wherein said cancer is metastatic renal cell carcinoma (mRCC), non-small cell lung cancer, melanoma, sarcoma, lymphoma, breast cancer, bladder cancer, cervical cancer, colon cancer, head and neck cancer, liver cancer, stomach cancer, or rectal cancer.

P Embodiment 14. The method of P embodiment 13, wherein said cancer is mRCC.

P Embodiment 15. The method of any one of P embodiments 1 to 14, wherein said cancer is a recurrence of cancer.

P Embodiment 16. The method of any one of P embodiments 1 to 15, wherein said cancer is chemotherapeutic resistant cancer.

P Embodiment 17. The method of any one of P embodiments 1 to 16, wherein said cancer is a metastatic cancer.

P Embodiment 18. A pharmaceutical composition comprising an anti-cancer agent in a first dosage form and CBM588 LBP in a second dosage form.

P Embodiment 19. The pharmaceutical composition of P embodiment 18, wherein the anti-cancer agent is at a dosage below its therapeutically effective amount when used in the absence of CBM588 LBP for cancer treatment.

P Embodiment 20. The pharmaceutical composition of P embodiment 18 or 19, wherein the anti-cancer agent is a checkpoint inhibitor.

P Embodiment 21. The pharmaceutical composition of P embodiment 20, wherein the checkpoint inhibitor is a PD-1, PDL-1 or CTLA-4 inhibitor.

P Embodiment 22. The pharmaceutical composition of P embodiment 20 or 21, wherein the checkpoint inhibitor is nivolumab, ipilimumab, pembrolizumab, cemiplimab, durvalumab, daclizumab, avelumab, or atezolizumab.

P Embodiment 23. The pharmaceutical composition of any one of P embodiments 20 to 22, wherein said checkpoint inhibitor is nivolumab.

P Embodiment 24. The pharmaceutical composition of any one of P embodiments 20 to 22, wherein said checkpoint inhibitor is ipilimumab.

P Embodiment 25. The pharmaceutical composition of any one of P embodiments 18 to 24, further comprising a second anti-cancer agent.

P Embodiment 26. The pharmaceutical composition of P embodiment 25, wherein the second anti-cancer agent is a second checkpoint inhibitor.

P Embodiment 27. The pharmaceutical composition of P embodiment 26, wherein the second checkpoint inhibitor is nivolumab, ipilimumab, pembrolizumab, cemiplimab, durvalumab, daclizumab, avelumab, or atezolizumab.

P Embodiment 28. The pharmaceutical composition of P embodiment 26 or 27, wherein the second checkpoint inhibitor is nivolumab.

P Embodiment 29. The pharmaceutical composition of P embodiment 26 or 27, wherein the second checkpoint inhibitor is ipilimumab.

P Embodiment 30. A kit comprising: (a) a first pharmaceutical composition comprising an anticancer agent in a first dosage form and a pharmaceutically acceptable excipient in a suitable container or with suitable packaging; and (b) a second pharmaceutical composition comprising a CBM588 LBP preparation in a second dosage form in a suitable container or with suitable packaging.

P Embodiment 31. The kit of P embodiment 30, wherein the anti-cancer agent is a checkpoint inhibitor.

P Embodiment 32. The kit of P embodiment 31, wherein the checkpoint inhibitor is a PD-1, PDL-1 or CTLA-4 inhibitor.

P Embodiment 33. The kit of P embodiment 31 or 32, wherein the checkpoint inhibitor is nivolumab, ipilimumab, pembrolizumab, cemiplimab, durvalumab, daclizumab, avelumab, or atezolizumab.

P Embodiment 34. The kit of any one of P embodiments 31 to 33, wherein said checkpoint inhibitor is nivolumab.

P Embodiment 35. The kit of P embodiments 31 to 33, wherein said checkpoint inhibitor is ipilimumab.

P Embodiment 36. The kit of any one of P embodiments 30 to 35, further comprising (c) a third pharmaceutical composition comprising a second anti-cancer agent and a pharmaceutically acceptable excipient in a suitable container or with suitable packaging.

P Embodiment 37. The kit of P embodiment 36, wherein the second anti-cancer agent is a second checkpoint inhibitor.

P Embodiment 38. The kit of P embodiment 37, wherein the second checkpoint inhibitor is nivolumab, ipilimumab, pembrolizumab, cemiplimab, durvalumab, daclizumab, avelumab, or atezolizumab.

P Embodiment 39. The kit of P embodiment 37 or 38, wherein the second checkpoint inhibitor is nivolumab.

P Embodiment 40. The kit of P embodiment 37 or 38, wherein the second checkpoint inhibitor is ipilimumab.

Embodiments

Embodiment 1. A method for treating cancer in a subject in need thereof, said method comprising administering to said subject a therapeutically effective amount of an anti-cancer agent and *Clostridium butyricum.*

Embodiment 2. The method of embodiment 1, wherein said *Clostridium butyricum* is a live biotherapeutic product.

Embodiment 3. The method of embodiment 2, wherein said *Clostridium butyricum* live biotherapeutic product is *Clostridium butyricum* MIYAIRI 588 live biotherapeutic product (CBM588 LBP).

Embodiment 4. The method of any one of embodiments 1 to 3, wherein the anti-cancer agent is a checkpoint inhibitor.

Embodiment 5. The method of embodiment 4, wherein the checkpoint inhibitor is a PD-1, PD-L1 or CTLA-4 inhibitor.

Embodiment 6. The method of embodiment 4 or 5, wherein said checkpoint inhibitor is nivolumab, ipilimumab, pembrolizumab, cemiplimab, durvalumab, daclizumab, avelumab, or atezolizumab.

Embodiment 7. The method of any one of embodiments 4 to 6, wherein said checkpoint inhibitor is nivolumab.

Embodiment 8. The method of any one of embodiments 4 to 6, wherein said checkpoint inhibitor is ipilimumab.

Embodiment 9. The method of any one of embodiments 1 to 8, further comprising administering a second anticancer agent.

Embodiment 10. The method of embodiment 9, wherein said second anti-cancer agent is a second checkpoint inhibitor.

Embodiment 11. The method of embodiment 10, wherein said second checkpoint inhibitor is nivolumab, ipilimumab, pembrolizumab, cemiplimab, durvalumab, daclizumab, avelumab, or atezolizumab.

Embodiment 12. The method of embodiment 10 or 11, wherein the second checkpoint inhibitor is nivolumab.

Embodiment 13. The method of embodiment 10 or 11, wherein the second checkpoint inhibitor is ipilimumab.

Embodiment 14. The method of any one of embodiments 1 to 13, wherein said cancer is a microsatellite-instability high (MSI-H) cancer.

Embodiment 15. The method of any one of embodiments 1 to 14, wherein said cancer is metastatic renal cell carcinoma (mRCC), non-small cell lung cancer, melanoma, sarcoma, lymphoma, breast cancer, bladder cancer, cervical cancer, colon cancer, head and neck cancer, liver cancer, stomach cancer, or rectal cancer.

Embodiment 16. The method of embodiment 15, wherein said cancer is mRCC.

Embodiment 17. The method of any one of embodiments 1 to 16, wherein said cancer is a recurrence of cancer.

Embodiment 18. The method of any one of embodiments 1 to 17, wherein said cancer is chemotherapeutic resistant cancer.

Embodiment 19. The method of any one of embodiments 1 to 18, wherein said cancer is a metastatic cancer.

Embodiment 20. A pharmaceutical composition comprising an anti-cancer agent in a first dosage form and *Clostridium butyricum* in a second dosage form.

Embodiment 21. The pharmaceutical composition of embodiment 20, wherein said *Clostridium butyricum* is a live biotherapeutic product.

Embodiment 22. The pharmaceutical composition of embodiment 21, wherein said *Clostridium butyricum* live biotherapeutic product is *Clostridium butyricum* MIYAIRI 588 live biotherapeutic product (CBM588 LBP).

Embodiment 23. The pharmaceutical composition of any one of embodiments 20 to 22, wherein said anti-cancer agent is at a dosage below its therapeutically effective amount when used in the absence of CBM588 LBP for treating cancer.

Embodiment 24. The pharmaceutical composition of any one of embodiments 20 to 23, wherein said anti-cancer agent is a checkpoint inhibitor.

Embodiment 25. The pharmaceutical composition of embodiment 24, wherein said checkpoint inhibitor is a PD-1, PD-L1 or CTLA-4 inhibitor.

Embodiment 26. The pharmaceutical composition of embodiment 24 or 23, wherein said checkpoint inhibitor is nivolumab, ipilimumab, pembrolizumab, cemiplimab, durvalumab, daclizumab, avelumab, or atezolizumab.

Embodiment 27. The pharmaceutical composition of any one of embodiments 24 to 26, wherein said checkpoint inhibitor is nivolumab.

Embodiment 28. The pharmaceutical composition of any one of embodiments 24 to 26, wherein said checkpoint inhibitor is ipilimumab.

Embodiment 29. The pharmaceutical composition of any one of embodiments 20 to 28, further comprising a second anti-cancer agent.

Embodiment 30. The pharmaceutical composition of embodiment 29, wherein the second anti-cancer agent is a second checkpoint inhibitor.

Embodiment 31. The pharmaceutical composition of embodiment 30, wherein the second checkpoint inhibitor is nivolumab, ipilimumab, pembrolizumab, cemiplimab, durvalumab, daclizumab, avelumab, or atezolizumab.

Embodiment 32. The pharmaceutical composition of embodiment 30 or 31, wherein the second checkpoint inhibitor is nivolumab.

Embodiment 33. The pharmaceutical composition of embodiment 30 or 31, wherein the second checkpoint inhibitor is ipilimumab.

Embodiment 34. A kit comprising: (a) a first pharmaceutical composition comprising an anticancer agent in a first dosage form and a pharmaceutically acceptable excipient in a suitable container or with suitable packaging; and (b) a second pharmaceutical composition comprising *Clostridium butyricum* in a second dosage form in a suitable container or with suitable packaging.

Embodiment 35. The kit of embodiment 34, wherein said *Clostridium butyricum* is a live biotherapeutic product.

Embodiment 36. The kit of embodiment 35, wherein said *Clostridium butyricum* live biotherapeutic product is *Clostridium butyricum* MIYAIRI 588 live biotherapeutic product (CBM588 LBP).

Embodiment 37. The kit of any one of embodiments 34 to 36, wherein said anti-cancer agent is a checkpoint inhibitor.

Embodiment 38. The kit of embodiment 37, wherein said checkpoint inhibitor is a PD-1, PD-L1 or CTLA-4 inhibitor.

Embodiment 39. The kit of embodiment 37 or 38, wherein the checkpoint inhibitor is nivolumab, ipilimumab, pembrolizumab, cemiplimab, durvalumab, daclizumab, avelumab, or atezolizumab.

Embodiment 40. The kit of any one of embodiments 37 to 39, wherein said checkpoint inhibitor is nivolumab.

Embodiment 41. The kit of any one of embodiments 37 to 39, wherein said checkpoint inhibitor is ipilimumab.

Embodiment 42. The kit of any one of embodiments 34 to 41, further comprising (c) a third pharmaceutical composition comprising a second anti-cancer agent and a pharmaceutically acceptable excipient in a suitable container or with suitable packaging.

Embodiment 43. The kit of embodiment 42, wherein the second anti-cancer agent is a second checkpoint inhibitor.

Embodiment 44. The kit of embodiment 43, wherein the second checkpoint inhibitor is nivolumab, ipilimumab, pembrolizumab, cemiplimab, durvalumab, daclizumab, avelumab, or atezolizumab.

Embodiment 45. The kit of embodiment 43 or 44, wherein the second checkpoint inhibitor is nivolumab.

EXAMPLES

Example 1: Evaluation of the Biologic Effect of *Clostridium butyricum* MIYAIRI 588 Live Biotherapeutic Product (CBM588 LBP) in Combination with Nivolumab/Ipilimumab for Patients with Metastatic Renal Cell Carcinoma (mRCC)

Background of Studies Described Herein

The landscape of therapy for mRCC has changed drastically over the past decade. Most recently, nivolumab/ipilimumab has been introduced in the front-line setting based on data from the CheckMate214 trial, showing an overall survival benefit relative to sunitinib. Although the data are encouraging for this strategy of dual checkpoint inhibition, the vast majority of patients are not cured of their disease. Only a minority (46%) of patients respond to immunotherapy, and approximately 20% of patients will progress through therapy.

Recent studies suggest that the gut microbiome may play a key role in modulating responses to immunotherapy. In murine models, Vetizou and colleagues have reported that the activity of cytotoxic T-lymphocyte associated protein 4 (CTLA4)-blocking therapies is dependent upon the presence of *Bacteroides* spp.[5] In the context of PD-1, Sivan and colleagues have shown that the clinical activity of anti-PD-1 agents is related to *Bifidobacterium* spp.[6] Gopalakrishnan and colleagues reported a correlation between the microbiome composition and response to anti-PD1 agents in 43 patients with metastatic melanoma.[7] Routy et al showed that the relative abundance of *Akkermansia municiphila* was closely linked to response.[8]

Applicants therefore proposed assessing *Clostridium butyricum* MIYAIRI 588 live biotherapeutic product (CBM588 LBP) in combination with the checkpoint inhibitors nivolumab/ipilimumab to determine anti-cancer effects.

The Microbiome in mRCC

Applicants first interrogated the role of the microbiome in mRCC patients receiving nivolumab and TKIs. Patients receiving sunitinib or nivolumab were enrolled through two separate, IRB-approved protocols (COH IRB 16088 and COH IRB 16323, respectively). In these studies, Applicants utilized stool samples for DNA extraction and analysis.

The first protocol randomized patients receiving sunitinib to either a diet excluding yogurt or any bacterial fortified foods, or mandated that patients take a standard 4 ounces of a standard yogurt supplement (Activia™) twice daily for the 12-week study period. The second protocol mandated exclusion of yogurt or bacterial fortified foods for the 12-week study period.

At the end of the 12-week study period, the response was characterized using RECIST 1.1 criteria. For purposes of that study, responders were defined as patients achieving a complete response (CR), partial response (PR) or stable disease (SD) by 3 months of therapy, while non-responders were defined as those with progressive disease (PD) as the best response.

Fecal samples were processed using protocols established by the Earth Microbiome Project (EMP). Briefly, DNA from 250 mg of fecal material for each sample was extracted using the DNeasy PowerSoil kit (MoBio Laboratories, Qiagen Company, Carlsbad, CA). The manufacturer's protocol was followed with the exception of a 10 minute incubation at 65 C after the addition of solution Cl per the EMP protocol. 16S amplicon libraries with barcoded adapters corresponding to the Illumina chemistry were prepared from the extracted DNA using previously described methods. Each library was quantified with qPCR (Kapa Biosystems; Wilmington, MA). The quantified libraries were pooled at equimolar concentrations. The pool was quantified and run on the Illumina MiSeq using version 3 chemistry (Illumina Inc.; San Diego, CA).

Sequence reads were processed by Mothur software, as described in MiSeq SOP, assembled in OUTs, taxonomically annotated to the level of genus and used to construct Bray-Curtis dissimilarity matrix. The similarity of samples was visualized by PCoA and further confirmed by ANOSIM tests, differentially abundant taxa were determined by METASTATS software.

Processed fecal DNA was subject to PCR using universal primers. The PCR amplicons were sequenced, rarefied to 10,000 sequences/sample and low-quality sequences were trimmed. Chimeric sequences were removed and assembled in 7,097 operating taxonomic units (OTUs) and taxonomically annotated to the genera level. OTU size ranged from 1 sequence for median and minimal sizes, 37 for average sizes, and 30,878 for maximum sizes. The OTUs were used to assess the structure, membership, and dynamics of the gut microbial community. OTU abundances were standardized and used to calculate distances between samples using Bray-Curtis dissimilarity measure, and visualized by PCoA plot. Distribution of samples confirmed that the structure of gut microbiota was patient specific (ANOSIM, p=0.001) and that the treatment response was among significant factors affecting sample separation (ANOSIM, p=0.01).

Figure 1A:
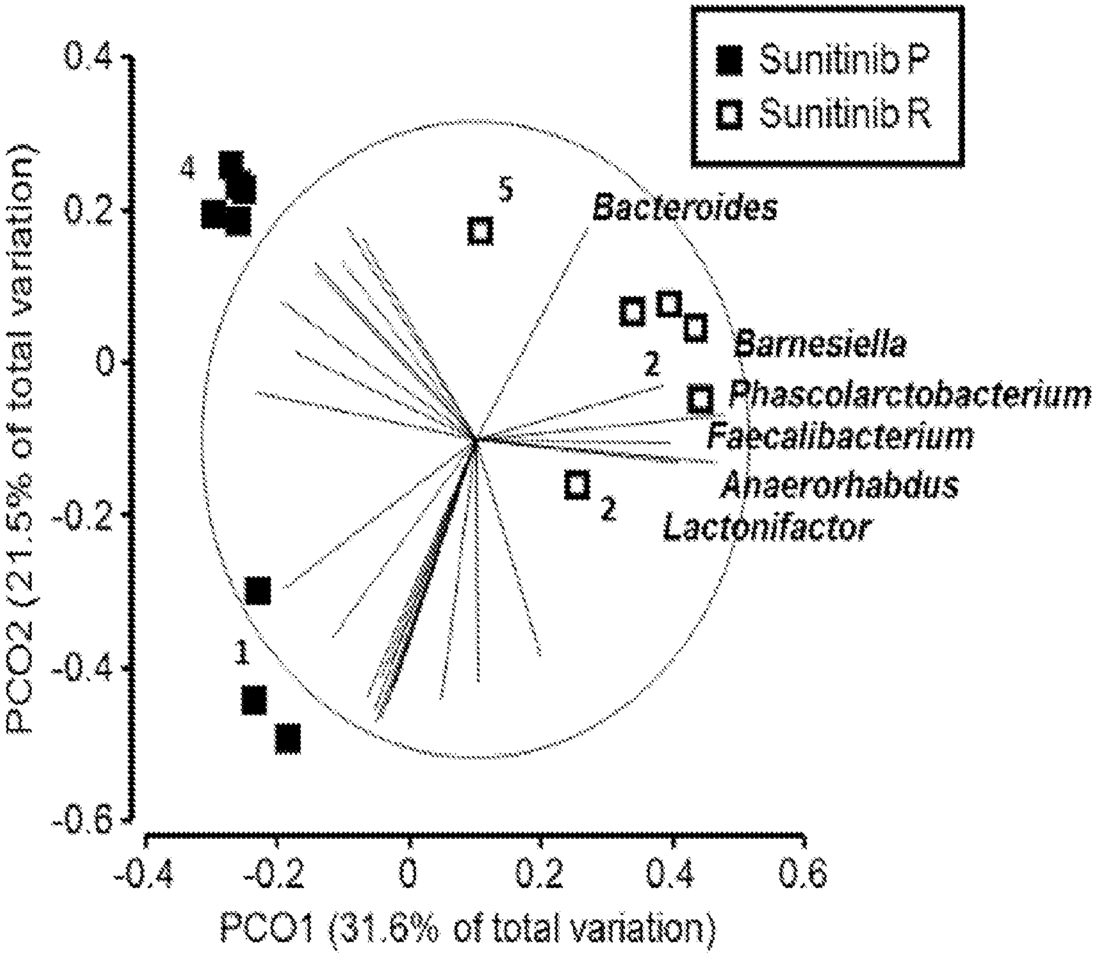
FIGS. 1A and 1B are Principal Coordinates Analysis (PCoA) plots showing the microbial community of patients responding to sunitinib (FIG. 1A) and nivolumab (FIG. 1B). "P" indicates tumor progression and "R" indicates responding to treatment.
Figure 1B:
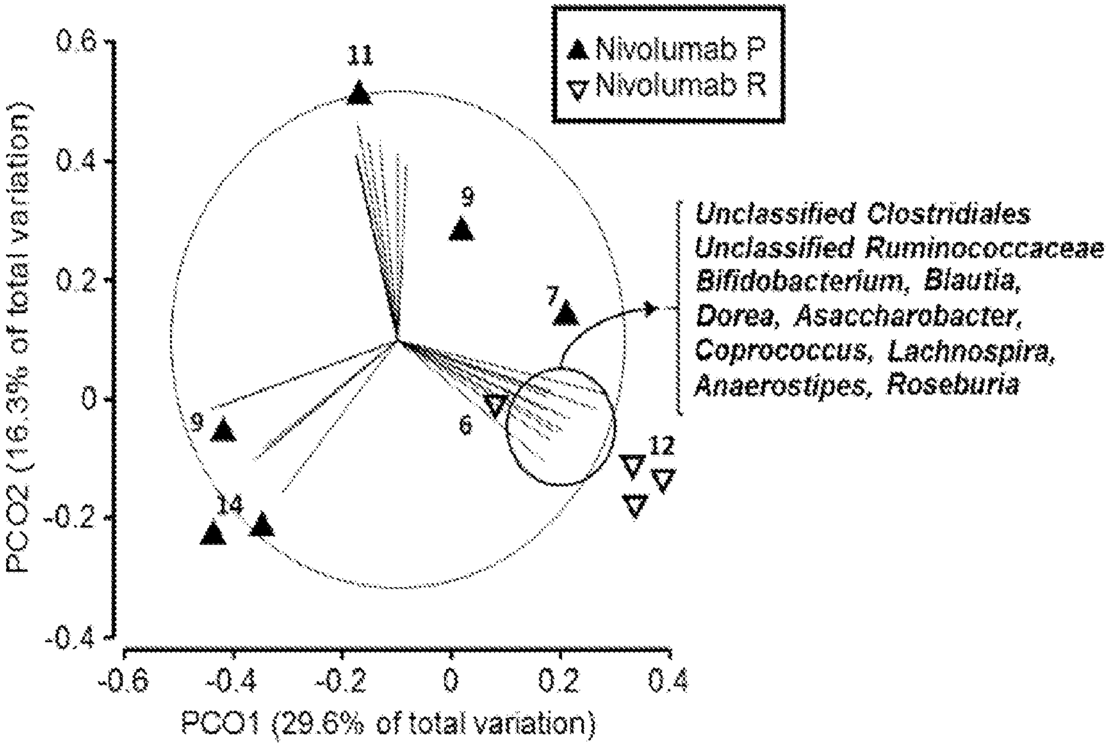

The structure of microbial community was compared between patients responding to nivolumab and sunitinib treatment and patients with progressing tumor using 8 samples collected before the initiation of treatment (time point 1 [T1]), as illustrated in FIGS. 1A and 1B. The Gini-Simpson index suggested that the complexity of gut microbiota was not significantly different between the response groups (Wilcoxon rank-sum test p=0.25). At the same time, the observed trend suggested that the microbiota of patients responding to the treatment has higher complexity. The structure of gut microbiota was resolved to the level of phylum and genus. METASTATS identified phylum Bacteroidetes, genera Barnesiella, and *Bacteroides* as elevated among responders (p<0.05 for each). Although phylum Proteobacteria was elevated in non-responders, METASTATS analysis suggested that this difference was not significant (p=0.29).

Taken together, the data suggested that specific bacterial species (e.g., *Bifidobacterium*, Clostridiales, etc) are associated with the clinical efficacy associated with immunotherapy in mRCC. Applicants therefore proposed the combination of nivolumab/ipilimumab with CBM588 LBP in patients with mRCC as a novel approach of enhancing subpopulations of bacteria, such as *Bifidobacterium.*

CBM588 LBP

CBM588 is a strain of *Clostridium butyricum* used commercially in Japan as a live biotherapeutic product in humans and a feed additive in animals. CBM588 was authorized by the European Union as a novel food ingredient in 2014, and as a feed additive for turkeys, chickens, and related minor avian species.[9] In a pediatric study including 110 children with upper respiratory tract infection or gastroenteritis, CBM588 administered as an LBP was safe and well-tolerated. Furthermore, the incidence of antibiotic-related diarrhea was markedly reduced in patients who received CBM588 LBP (59% vs 5%).[10] In a study of ulcerative colitis, CBM588 LBP was administered at a dose of 60 mg oral tid.[11,12]

There is a lack of data documenting the safety, tolerability and efficacy of the combination of CBM588 LBP with immunotherapy in patients with advanced cancer. Applicants therefore assessed CBM588 LBP as an adjunct to nivolumab/ipilimumab in patients with mRCC in a phase I protocol. The OBED represents the dose that results in the greatest increase in *Bifidobacterium* from baseline to week 6 of therapy. *Bifidobacterium* was selected amongst other putative bacteria that are associated with response to immunotherapy, since CBM588 LBP may specifically increase levels of this genus.

Eligibility Criteria

Inclusion Criteria:

Participants must meet all of the following criteria on screening examination to be eligible to participate in the study: histological confirmation of RCC with a clear-cell component; advanced (not amenable to curative surgery or radiation therapy) or metastatic (AJCC Stage IV) RCC; no prior systemic therapy for RCC with the following exception: one prior adjuvant or neoadjuvant therapy for completely resectable RCC if such therapy did not include an agent that targets PD-1 or PD-L1 and if recurrence occurred at least 6 months after the last dose of adjuvant or neoadjuvant therapy; ECOG Performance Status<2; measurable disease as per RECIST 1.1.

Key Exclusion Criteria:

Presence of untreated brain metastases. Patients with treated brain metastases must be stable for 4 weeks after completion of treatment and have documented stability on pre-study imaging. Patients must have no clinical symptoms from brain metastases and have no requirement for systemic corticosteroids amounting to >10 mg/day of prednisone or its equivalent for at least 2 weeks prior to first dose of study drug. Patients with known leptomeningeal metastases are excluded, even if treated.

Prior treatment with an anti-PD-1, anti-PD-L1, anti-PD-L2, anti-CD137, or anti-CTLA-4 antibody, or any other antibody or drug specifically targeting T-cell co-stimulation or checkpoint pathways.

Any active or recent history of a known or suspected autoimmune disease or recent history of a syndrome that required systemic corticosteroids (>10 mg daily prednisone equivalent) or immunosuppressive medications except for syndromes which would not be expected to recur in the absence of an external trigger. Subjects with vitiligo or type I diabetes mellitus or residual hypothyroidism due to autoimmune thyroiditis only requiring hormone replacement are permitted to enroll.

Current use, or intent to use, probiotics, yogurt or bacterial fortified foods during the period of treatment.

Any condition requiring systemic treatment with corticosteroids (>10 mg daily prednisone equivalents) or other immunosuppressive medications within 14 days prior to first dose of study drug. Inhaled steroids and adrenal replacement steroid doses >10 mg daily prednisone equivalents are permitted in the absence of active autoimmune disease.

Uncontrolled Adrenal Insufficiency.

Known medical condition (e.g., a condition associated with diarrhea or acute diverticulitis) that, in the investigator's opinion, would increase the risk associated with study participation or study drug administration or interfere with the interpretation of safety results.

Grade 1 (NCI CTCAE v4) or baseline before administration of study drug.

Any of the following laboratory test findings: WBC<2,000/$mm^3$, Neutrophils<1,500/$mm^3$, Platelets<100,000/$mm^3$, AST or ALT>3×ULN (>5×ULN if liver metastases are present), total bilirubin>1.5×ULN (except subjects with Gilbert Syndrome, who can have total bilirubin 3.0 mg/dL), serum creatinine>1.5×upper limit of normal (ULN).

Treatment Program Overview

TABLE 1

Treatment groups were randomized (2:1) to nivolumab/ipilimumab with CBM588 LBP or nivolumab/ipilimumab alone.

| | Treatment Arms | | |
|---|---|---|---|
| | Number | Dose | |
| | of Patients | CBM588 LBP | Nivolumab/Ipilimumab |
| Arm 1 | 10 | None | 3 mg/kg/1 mg/kg |
| Arm 2 | 20 | 80 mg bid | 3 mg/kg/1 mg/kg |

The primary objective of this study was (1) to determine the effect of CBM588 LBP (in combination with nivolumab/ipilimumab) in modulation of gut microbiome in patients with mRCC. Secondary objectives were: (1) to evaluate the effect of CBM588 LBP on the clinical efficacy of the nivolumab/ipilimumab combination and (2) to determine the effect of CBM588 LBP on systemic immunodulation of the nivolumab/ipilimumab combination in patients with mRCC.

Evaluation criteria and endpoints were as follows, and are shown in Tables 2 and 3. The primary endpoint was (1) change in *Bifidobacterium* composition of stool from baseline to week 12 of therapy on the CBM588 LBP+nivolumab/ipilimumab vs nivolumab/ipilimumab alone. Secondary endpoints were (1) comparison of the Shannon index (a measure of microbial diversity) from baseline to week 12 of therapy on the CBM588 LBP+nivolumab/ipilimumab vs nivolumab/ipilimumab alone, (2a) best overall response, by RECIST criteria, with nivolumab/ipilimumab alone vs nivolumab/ipilimumab with CBM588 LBP, (2b) progression-free survival (PFS), assessed as the duration of time from enrollment to progression, with nivolumab/ipilimumab alone vs nivolumab/ipilimumab with CBM588 LBP, (3a) comparison of the proportion of circulating Tregs at baseline to levels of circulating Tregs with nivolumab/ipilimumab alone vs nivolumab/ipilimumab with CBM588 LBP, (3b) comparison of the proportion of circulating MDSCs with nivolumab/ipilimumab alone versus nivolumab/ipilimumab with CBM588 LBP, and (3c) comparison of IL-6, IL-8 and other cytokines/chemokines with nivolumab/ipilimumab alone versus nivolumab/ipilimumab with CBM588 LBP.

TABLE 2

| Primary Objectives | |
|---|---|
| Objectives | Endpoints/Measurements of Effect |
| To determine the effect of CBM588 LBP (in combination with nivolumab/ipilimumab) on the gut microbiome in patients with mRCC | Primary: Change in *Bifidobacterium* composition of stool from baseline to week 6 of therapy<br>Secondary: Comparison of the Shannon index (a measure of microbial diversity) from baseline to week 6 of therapy |

TABLE 3

| Secondary Objectives | |
|---|---|
| Objectives | Endpoints/Measurements of Effect |
| To evaluate the effect of CBM588 LBP on the clinical efficacy of the nivolumab/ipilimumab combination | Best overall response, by RECIST criteria, with nivolumab/ipilimumab alone versus nivolumab/ipilimumab with CBM588 LBP<br>Progression-free survival (PFS), assessed as the duration of time from enrollment to progression, with nivolumab/ipilimumab alone vs nivolumab/ipilimumab with CBM588 LBP |
| To assess the effect of CBM588 LBP on systemic immunodulation of the nivolumab/ipilimumab combination in patients with mRCC | Comparison of the proportion of circulating Tregs at baseline to levels of circulating Tregs with nivolumab/ipilimumab alone versus nivolumab/ipilimumab with CBM588 LBP<br>Comparison of the proportion of circulating MDSCs with nivolumab/ipilimumab alone versus nivolumab/ipilimumab with CBM588 LBP<br>Comparison of IL-6, IL-8 and other cytokines/chemokines with nivolumab/ipilimumab alone versus nivolumab/ipilimumab with CBM588 LBP |

One cycle of therapy constituted an every-3-week regimen of nivolumab with ipilimumab for the first 12 weeks. Thereafter, a cycle was considered 4 weeks, as nivolumab was administered on a monthly schedule thereafter. The treatment cycle is shown in Table 4.

CBM588 LBP: CBM588 LBP was administered orally on a daily basis at a dose of 80 mg twice daily in 100 ml of water (the contents of two sachets), and should be given indefinitely while on protocol.

Nivolumab: Nivolumab was administered at a dose of 3 mg/kg intravenously prior to administration of ipilimumab for the first 4 cycles followed by monthly dosing at 3 mg/kg.

Ipilimumab: Ipilimumab was administered after nivolumab administration, at a dose of 1 mg/kg intravenously for only the first 4 cycles, after which point, it was discontinued.

Agent Administration

CBM588:

CBM588 Fine Granules can be manufactured as an orally available live biotherapeutic comprised of *Clostridium butyricum* and packaged in 1 g sachets. Each sachet contains 40 mg of CBM588. CBM588 was administered orally at a dose of 80 mg twice daily in 100 ml of water (the contents of two sachets), and should be given indefinitely while on protocol. Subjects can take CBM588 with or without food. CBM588 should be taken at home, not in clinic. A cycle of defined administration is for 21 days.

Nivolumab:

Nivolumab injection is a clear opalescent, colorless to pale yellow, sterile, non-pyrogenic, single-use, isotonic aqueous solution formulated in sodium citrate, sodium chloride, mannitol, diethylenetriamine pentacetic acid (pentetic acid) and polysorbate 80 (Tween® 80), pH 6.0. Each vial is 100 mg (10 mg/mL) with a 0.7 mL overfill in 10 mL type I flint glass vials, with butyl rubber stoppers and aluminum seals. Vials of Nivolumab injection must be stored at 2°-8° C. (36° F.-46° F.) and protected from light, freezing and shaking. If a storage temperature excursion is identified, promptly return Nivolumab to 2° C. to 8° C. and quarantine the supplies.

Nivolumab can be infused undiluted (10 mg/mL) or diluted with 0.9% Sodium Chloride injection, USP or 5% dextrose, USP to drug concentrations no less than 0.35 mg/mL. Nivolumab injection is to be administered as a 60 minute IV infusion through a 0.2 micron to 1.2 micron pore size, low protein binding polyethersulfone membrane in-line filter. No compatibilities between nivolumab and polyvinyl chloride (PVC), nonPVC DHEP (di(2-ethylhexyl)phthalate) IV components, or glass bottles have been observed.

The administration of undiluted and diluted solutions of nivolumab must be completed within 24 hours preparation.

If not used immediately, the infusion solution may be stored up to 24 hours in a refrigerator at 2° C.-8° C. (36° F.-46° F.) and a maximum of 4 hours of the total 24 hours can be at room temperature (20° C.-25° C. (68° F.-77° F.)) and room light. The maximum 4-hour period under room temperature and room light conditions includes the product administration period. The single-use dosage form contains no anti-bacterial preservative or bacteriostatic agent. Therefore, it is advised that the product be discarded 8 hours after initial entry.

Ipilimumab:

Ipilimumab injection is supplied as 200 mg/40 mL (5 mg/mL). It is formulated as a clear to slightly opalescent, colorless to pale yellow, sterile, non-pyrogenic, single-use, isotonic aqueous solution that may contain particles. Vials of ipilimumab injection must be stored at 2° C.-8° C. (36° F.-46° F.) and protected from light, freezing. If a storage temperature excursion is identified, promptly return ipilimumab to 2° C. to 8° C. and quarantine the supplies.

Ipilimumab is given undiluted (10 mg/mL) or further diluted in 0.9% Sodium Chloride injection, USP or 5% dextrose, USP in concentrations between 1 mg/mL and 4 mg/mL. Ipilimumab is stable in polyvinyl chloride (PVC), nonPVC DHEP (di(2-ethylhexyl)phthalate) IV bag or glass container up to 24 hours refrigerate at 2° C.-8° C. (36° F.-46° F.) or at room temperature/room light. The product may be infused using a volumetric pump at the protocol specific dose(s), nonpyrogenic, low-protein-binding filter (pore size of 0.2 micrometer or 1.2 micrometer). Prepared IV ipilimumab solution is stable up to 24 hours refrigerated at 2°–8° C. (36° F.-46° F.) or at room temperature/room light. Each vial is a type I flint glass vial with gray butyl stoppers and sealed with aluminum seals. Partially used vials or empty vials of ipilimumab injection should be discarded at the site according to appropriate drug disposal procedures.

TABLE 4

| Regiment Description | | | | | |
|---|---|---|---|---|---|
| Agent | Premedications and/or Precautions | Dose | Route | Schedule | Cycle Length |
| CBM588 LBP | No prophylactic medication should be given. | 80 mg | Oral | Twice per day on days 1-21 (and should be given indefinitely while on protocol). | 21 days (3 weeks) for two cycles |
| Nivolumab | No prophylactic medication should be given unless indicated by previous indication. | 3 mg/kg | 60 minute IV infusion | Day 1 | 21 days (3 weeks) for first 4 cycles 14 days (2 weeks) for cycles 5+ |
| Ipilimumab | No prophylactic medication should be given unless indicated by previous indication. | 1 mg/kg | 60 minutes IV infusion | Day 1 | 21 days (3 weeks) for 4 cycles |

Participants received protocol therapy until one of the below criteria are met: Disease progression, completed protocol therapy, participant is deemed intolerant to protocol therapy because of toxicity, despite dose modification/delay (if one agent is discontinued due to toxicity, then the participant may continue to receive the other study agents), general or specific changes in the patient's condition which render the patient unacceptable for further treatment in the judgment of the investigator, or withdrawal of consent for further protocol therapy.

Figure 2:
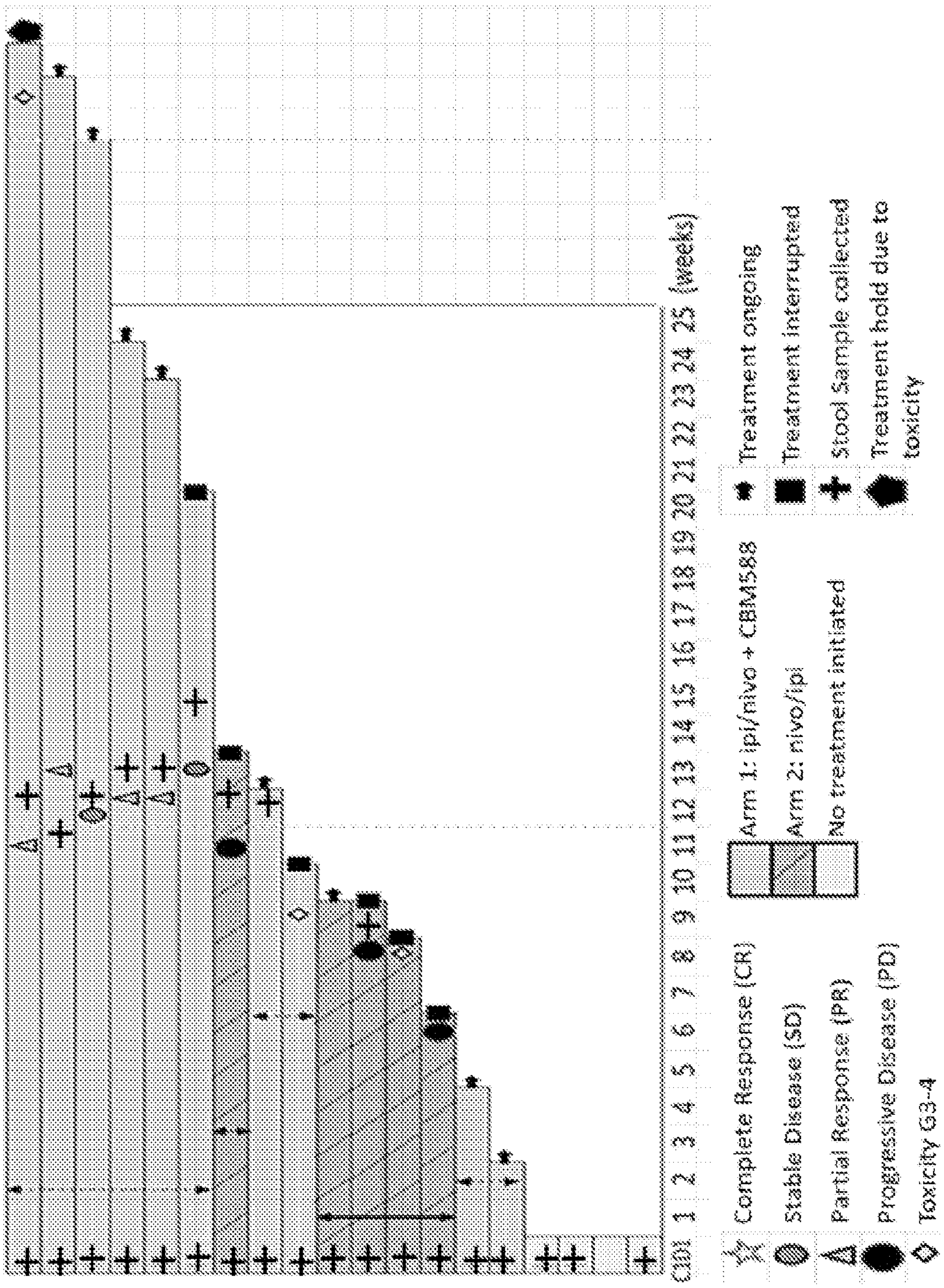
FIG. 2 illustrates the response of patients receiving nivolumab/ipilimumab treatment, nivolumab/ipilimumab+CBM588 LBP treatment, or no treatment (control group). The nivolumab/ipilimumab+CBM588 LBP treatment group is marked by dotted arrows, the nivolumab/ipilimumab treatment group is marked by solid arrows, and the no treatment group is unmarked by arrows.

Study participation concluded when any of the following occurred: Completion of study activities, withdrawal of consent, participant is lost to follow-up, at the discretion of the investigator for safety, behavioral, study termination or administrative reasons. Patient responses and study continuation for each treatment group are shown in FIG. 2.

Correlative/Special Studies and Laboratory Processing and Analysis

Assessment of Stool Microbiome

Samples were collected at pre-specified time points. Fecal material was collected in a 100 mL collection container by patients at two time points, before starting treatment (baseline) and at the start of week 13.

Total genomic DNA was isolated from 0.25 g of feces using the PowerSoil DNA isolation kit (Mo Bio, USA). Purified DNA will be separated on a 1% agarose gel and quantified by densitometry and spectrophotometry (NanoDrop 1000; Thermo Scientific, USA). As described by Stearns et al, a PCR protocol will be used to amplify bacterial 16S rRNA genes from all samples.12 Following PCR primers including Illumina part of adapter sequences were used to amplify V4 and V5 regions. In the below sequences M can be A or C.

```
SEQ ID NO: 1 V4-F:
ACACTCTTTCCCTACACGACGCTCTTCCGATCTGTGCCAGCMGCC

GCGGTAA.

SEQ ID NO: 2 V4-R:
ACACTCTTTCCCTACACGACGCTCTTCCGATCTGTGCCAGCMGCC

GCGGTAA.

SEQ ID NO: 3 V5-F:
ACACTCTTTCCCTACACGACGCTCTTCCGATCTGATTAGATACCC

TGGTAG.
```

-continued

```
SEQ ID NO: 4 V5-R:
GTGACTGGAGTTCAGACGTGTGCTCTTCCGATCTCCGTCAATTCM

TTTGAGTTT.
```

Complete Illumina adapter and barcodes were added by another 5 cycles of PCR to make Illumina library. After bioanalyzer and qPCR checking for QC. Multiple libraries were mixed equally. Paired-end of sequencing 2×100 bp will be performed by Illumina HiSeq 2000. Sequences were clustered at a variety of percent identities using USEARCH algorithm against the closed=reference.13 Taxonomy were then assigned using the RDP 2.4 classifier as described in Smith et. al.

Illumina/Solexa high throughput sequencing were used to sequence the 16S rRNA gene. Libraries were constructed for all samples by amplification of V3 region of bacterial 16S rRNA. Barcodes were created to uniquely index and label each sample for multiplex Illumina sequencing with paired end reads. Multiple test runs were first created to ensure the validity in 16S rRNA extraction and amplification from the fecal samples and standard QC were performed to examine the quality of multiplex Illumina sequencing. Low-quality reads were removed and only reads that perfectly matched the assembly were kept for further downstream analysis.

Assessment of Serum Cytokines

One 10 mL CPT tube was collected within 7 days before start of nivolumab and ipilimumab, during weeks 7, 13, 17 and 25 (+/−1 week). The pre-treatment sample may be collected on the morning of initiation of therapy, so long as the sample precedes ipilimumab/nivolumab administration. Efforts were made to collect the sample at the time of routine blood sample collection. Blood was collected into 10 mL CPT vacuum tube, inverted slowly about 8-10 times, maintained at room temperature.

The 10 mL CPT tube samples were processed ASAP, ideally within a window of 4-6 hours. CPT tubes were centrifuged at 1800×g (approximately 2800 rpm on a Sorvall RT6000 centrifuge) for 20 minutes at room temperature. After centrifugation, plasma in the CPT tubes were gently pipetted against the gel plug to dislodge cells stuck to the top of the gel. The cell suspension were transferred to a 50 mL conical polypropylene tube. cRPMI was added to a total of 40 mL. A 10 mL aliquot of cell suspension for counting was removed. The 50 mL tubes were then centrifuged at 250×g for seven minutes at room temperature. When centrifugation was complete, the supernatant was aspirated. PMBCs were either cryopreserved or used fresh.

Relevant WBC subset isolation was conducted through previously reported techniques. PBMCs were immersed in a mixture of PBS, 2% FCS and 0.1% (wt/vol) sodium azide with Fc III/IIR-specific antibody to block nonspecific binding and stained the cells with different combinations of fluorochrome-coupled antibodies to CD11c, I-Ab (MHC class II), CD86, CD11b, Gr1, CD49b, CD3, CD25 or Lag-3, or with annexin V (BD Biosciences). Fluorescence data on FACSCalibur (Beckton Dickinson) was collected and analyzed using FlowJo software (Tree Star). This method has been previously published by Chalmin et al.

Endpoint Measurements of Effect

Change in *Bifidobacterium* Composition of Stool from Baseline to Week 13 of Therapy Applicants assessed the proportion *Bifidobacterium* spp at baseline (relative to the cumulative assessment of microbial species) and compared this to the proportion observed after completion of 12 weeks of therapy.

Best Overall Response, by RECIST Criteria

Figure 3:
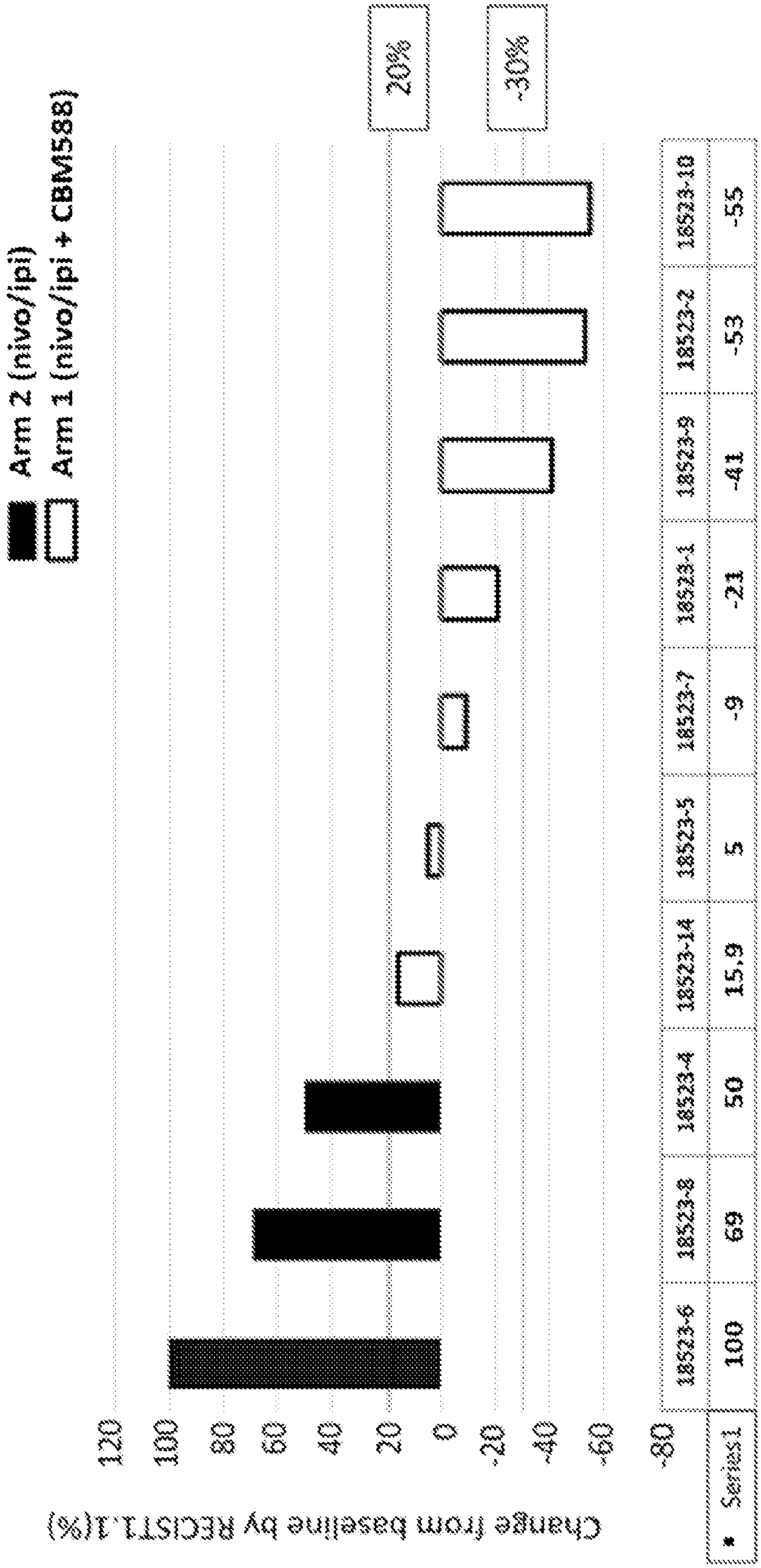
FIG. 3 is a bar graph showing response of patients receiving nivolumab/ipilimumab treatment (Arm 2) or nivolumab/ipilimumab+CBM588 LBP treatment (Arm 1). Patient response was measured based on RECIST, and percent change of target lesion from baseline are indicated on the lower panel.
Figure 4:
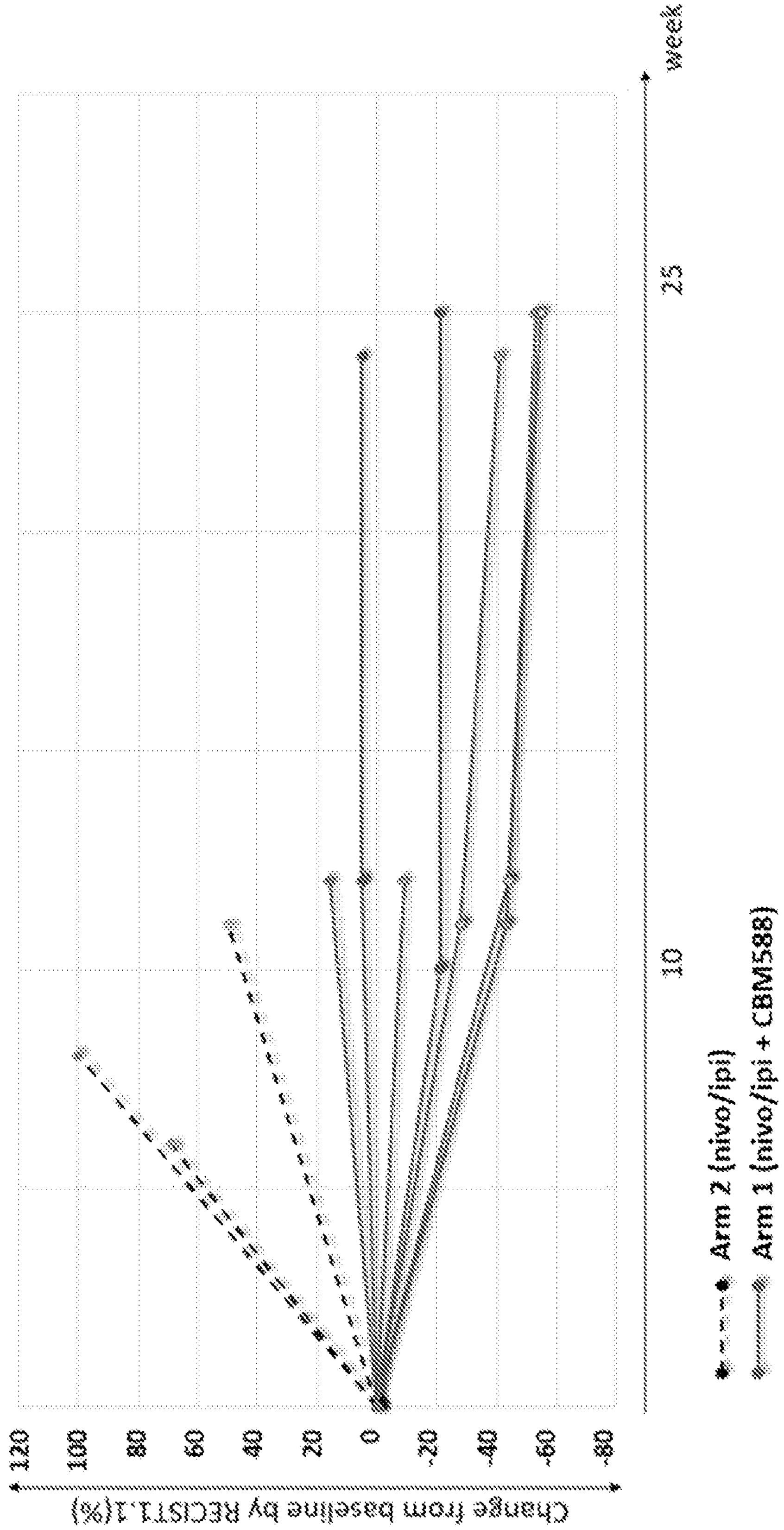
FIG. 4 is a graph showing response of tumors as measured by RECIST for patients undergoing nivolumab/ipilimumab treatment (Arm 2) or nivolumab/ipilimumab+CBM588 LBP treatment (Arm 1).

Response was a secondary endpoint in this trial. For this purpose of this study, patients were re-evaluated for response every 12 weeks. Response and progression, as shown in FIGS. 3 and 4, were evaluated in this study using the new international criteria proposed by the revised Response Evaluation Criteria in Solid Tumors (RECIST) guideline (version 1.1).[14] The results illustrate that the majority of patients receiving Nivolumab/Ipilimumab treatment displayed progressive disease, while patients receiving Nivolumab/Ipilimumab+CBM588 LBP treatment had characteristics of either stable disease or partial response to the treatment. The published RECIST document is available at website: eortc.be/RECIST. Changes in the largest diameter (unidimensional measurement) of the tumor lesions and the shortest diameter in the case of malignant lymph nodes were used in the RECIST criteria.

Evaluable for Toxicity. All Patients were Evaluable for Toxicity from the Time of their First Treatment with VV2003 Alone or in Combination with and Nivolumab and Ipilimumab Evaluable for objective response. Only those patients who have measurable disease present at baseline, have received at least one cycle of therapy, and have had their disease re-evaluated were considered evaluable for response. These patients had their response classified according to the definitions stated below. (Note: Patients who exhibit objective disease progression prior to the end of cycle 1 were considered evaluable.)

Evaluable Non-Target Disease Response. Patients who have lesions present at baseline that are evaluable but do not meet the definitions of measurable disease, have received at least one cycle of therapy, and have had their disease re-evaluated will be considered evaluable for non-target disease. The response assessment was based on the presence, absence, or unequivocal progression of the lesions.

Measurable disease. Measurable lesions are defined as those that can be accurately measured in at least one dimension (longest diameter to be recorded) as ≥20 mm by chest x-ray or as ≥10 mm with CT scan, MRI, or calipers by clinical exam. All tumor measurements were recorded in millimeters (or decimal fractions of centimeters).

Tumor lesions that are situated in a previously irradiated area were considered measurable.

Malignant lymph nodes. To be considered pathologically enlarged and measurable, a lymph node must be ≥15 mm in short axis when assessed by CT scan (CT scan slice thickness recommended to be no greater than 5 mm). At baseline and in follow-up, only the short axis was be measured and followed.

Non-measurable disease. All other lesions (or sites of disease), including small lesions (longest diameter <10 mm or pathological lymph nodes with ≥10 to <15 mm short axis), were considered non-measurable disease. Bone lesions, leptomeningeal disease, ascites, pleural/pericardial effusions, lymphangitis cutis/pulmonitis, inflammatory breast disease, and abdominal masses (not followed by CT or MRI), were considered as non-measurable.

Target lesions. All measurable lesions up to a maximum of 2 lesions per organ and 5 lesions in total, representative of all involved organs, were identified as target lesions and recorded and measured at baseline. Target lesions were selected on the basis of their size (lesions with the longest diameter), be representative of all involved organs, but in addition should be those that lend themselves to reproducible repeated measurements. It may be the case that, on occasion, the largest lesion does not lend itself to reproducible measurement in which circumstance the next largest lesion, which can be measured reproducibly should be selected. A sum of the diameters (longest for non-nodal lesions, short axis for nodal lesions) for all target lesions will be calculated and reported as the baseline sum diameters. If lymph nodes are to be included in the sum, then only the short axis is added into the sum. The baseline sum diameters will be used as reference to further characterize any objective tumor regression in the measurable dimension of the disease.

Non-target lesions. All other lesions (or sites of disease) including any measurable lesions over and above the 5 target lesions should be identified as non-target lesions and should also be recorded at baseline. Measurements of these lesions are not required, but the presence, absence, or in rare cases unequivocal progression of each should be noted throughout follow-up.

Methods for Evaluation of Measurable Disease

All measurements should be taken and recorded in metric notation using a ruler or calipers. All baseline evaluations should be performed as closely as possible to the beginning of treatment and never more than 4 weeks before the beginning of the treatment.

The same method of assessment and the same technique should be used to characterize each identified and reported lesion at baseline and during follow-up. Imaging-based evaluation is preferred to evaluation by clinical examination unless the lesion(s) being followed cannot be imaged but are assessable by clinical exam.

Clinical lesions: Clinical lesions will only be considered measurable when they are superficial (e.g., skin nodules and palpable lymph nodes) and >10 mm diameter as assessed using calipers (e.g., skin nodules). In the case of skin lesions, documentation by color photography, including a ruler to estimate the size of the lesion, is recommended.

Chest x-ray: Lesions on chest x-ray are acceptable as measurable lesions when they are clearly defined and surrounded by aerated lung. However, CT is preferable.

Conventional CT and MRI: This guideline has defined measurability of lesions on CT scan based on the assumption that CT slice thickness is 5 mm or less. If CT scans have slice thickness greater than 5 mm, the minimum size for a measurable lesion should be twice the slice thickness. MRI is also acceptable in certain situations (e.g. for body scans).

Use of MRI remains a complex issue. MRI has excellent contrast, spatial, and temporal resolution; however, there are many image acquisition variables involved in MRI, which greatly impact image quality, lesion conspicuity, and measurement. Furthermore, the availability of MRI is variable globally. As with CT, if an MRI is performed, the technical specifications of the scanning sequences used should be optimized for the evaluation of the type and site of disease. Furthermore, as with CT, the modality used at follow-up should be the same as was used at baseline and the lesions should be measured/assessed on the same pulse sequence. It is beyond the scope of the RECIST guidelines to prescribe specific MRI pulse sequence parameters for all scanners, body parts, and diseases. Ideally, the same type of scanner should be used and the image acquisition protocol should be followed as closely as possible to prior scans. Body scans should be performed with breath-hold scanning techniques, if possible.

PET-CT: At present, the low dose or attenuation correction CT portion of a combined PET-CT is not always of optimal diagnostic CT quality for use with RECIST measurements. However, if the site can document that the CT performed as part of a PET-CT is of identical diagnostic quality to a diagnostic CT (with IV and oral contrast), then the CT portion of the PET-CT can be used for RECIST measurements and can be used interchangeably with conventional CT in accurately measuring cancer lesions over time. Note, however, that the PET portion of the CT introduces additional data which may bias an investigator if it is not routinely or serially performed.

Ultrasound: Ultrasound is not useful in assessment of lesion size and should not be used as a method of measurement. Ultrasound examinations cannot be reproduced in their entirety for independent review at a later date and, because they are operator dependent, it cannot be guaranteed that the same technique and measurements will be taken from one assessment to the next. If new lesions are identified by ultrasound in the course of the study, confirmation by CT or MRI is advised. If there is concern about radiation exposure at CT, MRI may be used instead of CT in selected instances.

Evaluation of Target Lesions

Complete Response (CR): Disappearance of all target lesions. Any pathological lymph nodes (whether target or non-target) must have reduction in short axis to <10 mm. Partial Response (PR): At least a 30% decrease in the sum of the diameters of target lesions, taking as reference the baseline sum diameters. Progressive Disease (PD): At least a 20% increase in the sum of the diameters of target lesions, taking as reference the smallest sum on study (this includes the baseline sum if that is the smallest on study). In addition to the relative increase of 20%, the sum must also demonstrate an absolute increase of at least 5 mm. (Note: the appearance of one or more new lesions is also considered progressions). Stable Disease (SD): Neither sufficient shrinkage to qualify for PR nor sufficient increase to qualify for PD, taking as reference the smallest sum diameters while on study.

Evaluation of Non-Target Lesions

Complete Response (CR): Disappearance of all non-target lesions. All lymph nodes must be non-pathological in size (<10 mm short axis). Non-CR/Non-PD: Persistence of one or more non-target lesion(s) and/or maintenance of tumor marker level above the normal limits. Progressive Disease (PD): Appearance of one or more new lesions and/or unequivocal progression of existing non-target lesions. Unequivocal progression should not normally trump target lesion status. It must be representative of overall disease status change, not a single lesion increase. Although a clear progression of "non-target" lesions only is exceptional, the opinion of the treating physician should prevail in such circumstances, and the progression status should be confirmed at a later time by the review panel (or Principal Investigator).

Evaluation of Best Overall Response

The best overall response is the best response recorded from the start of the treatment until disease progression/recurrence (taking as reference for progressive disease the smallest measurements recorded since the treatment started). The patient's best response assignment will depend on the achievement of both measurement and confirmation criteria.

Duration of Time from Enrollment to Progression

PFS is defined as the duration of time from start of treatment to time of progression or death, whichever occurs first.

Comparison of the Shannon Index (a Measure of Microbial Diversity) from Baseline to Week 13 of Therapy Using translational methods described in Section 9.1, we will compute the Shannon index at baseline and at week 12 for a comparison of microbial diversity at these two timepoints.

Comparison of the Proportion of Circulating Tregs at Baseline to Levels of Circulating Tregs on Treatment Using translational methods described in Section 9.2, we will estimate the proportion of Tregs in the blood. This will be assessed graphically across serial timepoints of blood collection (see Study Calendar) to ascertain any trends.

Comparison of the Proportion of Circulating MDSCs at Baseline to Levels of Circulating MDSCs on Treatment Using translational methods described in Section 9.2, we will estimate the proportion of MDSCs in the blood. This will be assessed graphically across serial timepoints of blood collection (see Study Calendar) to ascertain any trends.

Comparison of IL-6, IL-8 and Other Cytokines at Baseline to Levels of the Same Cytokines on Treatment Using translational methods, Applicants will estimate the proportion of serum cytokines in the blood. This will be assessed graphically across serial timepoints of blood collection (see Study Calendar) to ascertain any trends.

Study Design

Described is a randomized study of nivolumab/ipilimumab alone or in combination with CBM588. The objective is to define the biologic effect of CBM588 when used in combination with nivolumab/ipilimumab. Applicants' preclinical data indicates that *Bifidobacterium* spp are associated with responses to immunotherapy; thus it is thought that CBM588 will increase levels of *Bifidobacterium* spp. Applicants compared the proportional increase in *Bifidobacterium* spp with the addition of CBM588 to CBM588 and identified the cohort that achieved the largest such increase relative to patients receiving nivolumab/ipilimumab alone.

Sample Size and Accrual Rate 30 patients are randomized in a 1:2 fashion to receive nivolumab/ipilimumab alone [Arm 1] or with CBM588 [Arm 2]. It is anticipated that accrual of 30 patients over a 2 year span (approximately 1.5 patients per month), with approximately 12 months of follow-up on average (based on PFS estimates for nivolumab/ipilimumab). Given an anticipated 80% rate of consent to this study based on existing studies in patients with newly diagnosed mRCC, we would have to approach approximately 2 patients per month. This is feasible with current rates of new patient volume at our institution.

Statistical Analysis Plan

Primary endpoint: Change in *Bifidobacterium* composition of stool from baseline to week 12 of therapy. Comparison of the Shannon index (a measure of microbial diversity) from baseline to week 12 of therapy. Analysis plan: Change in the *Bifidobacterium* from baseline to week 12 will be assessed for patients on both arms. With 20 on the CBM588 containing arm, and 10 on the non-CBM588 containing arm, Applicants will have 80% power to detect a 1 standard deviation (common standard deviation of the change in *Bifidobacterium*) difference between the mean change detected in the two groups using a two-group t-test with a one-sided type I error of 0.05.

Comparison of the Shannon index (a measure of microbial diversity) from baseline to week 12 of therapy will be conducted in a similar fashion. As this is a secondary measure, any conclusions will discuss the multiple comparison issue inherent in this second analysis.

Secondary endpoint: (1a) Best overall response, by RECIST criteria, with nivolumab/ipilimumab alone versus nivolumab/ipilimumab with CBM588. The association between treatment arm and overall response as per RECIST criteria (response observed vs not observed) will be examined using Fisher's exact test. (1b) Progression-free survival (PFS), assessed as the duration of time from enrollment to progression, with nivolumab/ipilimumab alone versus nivolumab/ipilimumab with CBM588. Analysis plan: The difference in progression free survival across the two groups will be explored graphically using Kaplan-Meier survival plots. Median progression-free survival time for each of the two arms will be reported and Cox Proportional Hazards model will be used to estimate the hazard ratio and its confidence interval.

An exploratory analysis of the following will be conducted, with no adjustment for the multiple comparison issue although any conclusion will include a discussion of the limitations of any conclusions drawn due to the multiple comparisons concern: (2a) Comparison of the proportion of circulating Tregs at baseline to levels of circulating Tregs with nivolumab/ipilimumab alone versus nivolumab/ipilimumab with CBM588. (2b) Comparison of the proportion of circulating myeloid-derived suppressor cells (MDSC) with nivolumab/ipilimumab alone versus nivolumab/ipilimumab with CBM588. (2c) Comparison of IL-6, IL-8 and other cytokines/chemokines with nivolumab/ipilimumab alone versus nivolumab/ipilimumab with CBM588.

Example 2: Analysis of the Anti-Cancer Effect of CBM588 LBP in Combination with Nivolumab/Ipilimumab for Patients with Metastatic Renal Cell Carcinoma (mRCC)

Applicants further assessed anti-cancer effects of the combination treatment including nivolumab/ipilimumab and CBM588 LBP described in Example 1. The median follow-up time for patients undergoing the treatment trials was 89 weeks. Characteristics of patients who were enrolled in the trial are as shown in Table 5.

TABLE 5

Patient Characteristics

| | Overall n = 29 | Nivolumab/ ipilimumab n = 10 | Nivolumab/ ipilimumab/ CBM588 n = 19 |
|---|---|---|---|
| Baseline patient characteristics | | | |
| Age, median (range) | 66 (45-90) | 64 (46-79) | 64 (45-90) |
| Gender | | | |
| Male | 21 (72%) | 7 (%) | 14 (70%) |
| Female | 8 (28%) | 2 (%) | 6 (30%) |
| Histology | | | |
| Clear cell RCC | 19 (63%) | 6 (%) | 12 (60%) |
| Clear cell RCC with sarcomatoid features | 6 (20%) | 2 (%) | 4 (20%) |
| Non-clear cell RCC | | | |
| Papillary RCC | 1 (3%) | 1 (%) | |
| Papillary RCC with sarcomatoid features | 2 (7%) | | 2 (10%) |
| Sarcomatoid RCC | 2 (7%) | 0 | 2 (10%) |
| IMDC risk category | | | |
| Favorable | 1 (3%) | 0 | 0 |
| Intermediate | 23 (77%) | 7 (%) | 17 (80%) |
| Poor | 6 (20%) | 2 (%) | 3 (15%) |
| Nephrectomy, yes | 13 (43%) | 4 (%) | 9 (45%) |
| Metastatic sites | | | |
| Lung | 19 (63%) | 6 (%) | 13 (65%) |
| Mediastinal in | 10 (33%) | 5 (%) | 5 (25%) |
| Retroperitoneal in | 9 (30%) | 5 (%) | 4 (20%) |
| Supraclavicular | 2 (6%) | 0 | 2 (10%) |
| Bone | 11 (37%) | 4 (%) | 7 (35%) |
| Adrenal | 4 (13%) | 2 (%) | 2 (10%) |
| liver | 5 (17%) | 2 (%) | 3 (15%) |
| Soft tissue | 11 (37%) | 2 (%) | 8 (40%) |
| Pancreas | 3 (10%) | 1 (%) | 2 (10%) |
| Nephrectomy bed | 1 (3%) | 1 (%) | 0 |

Figure 5:
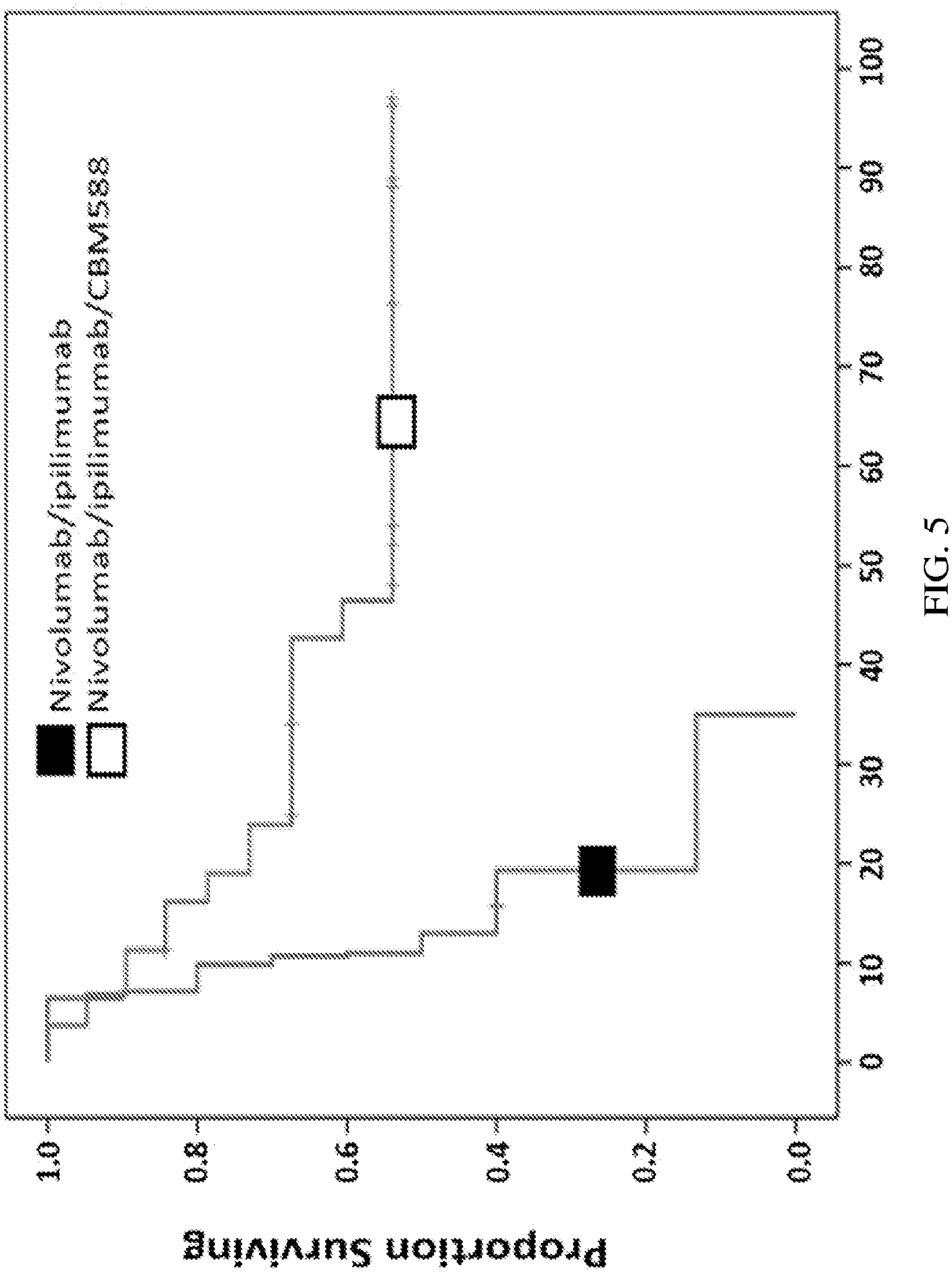
FIG. 5 is a graph illustrating the proportion of patients each week who had progression free survival. The patients were administered nivolumab/ipilimumab treatment or nivolumab/ipilimumab+CBM588 LBP treatment.
Figure 6:
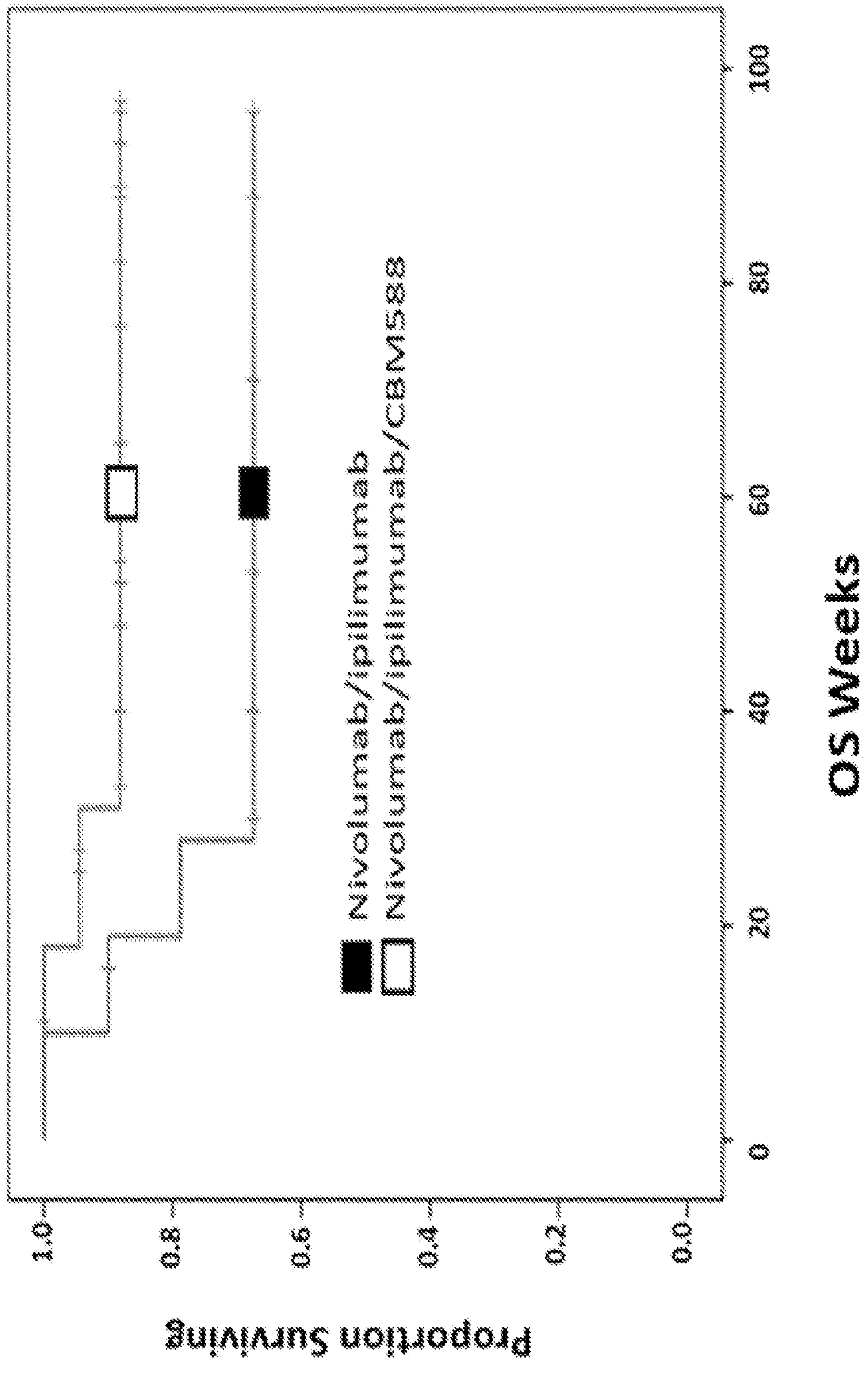
FIG. 6 is a graph illustrating the overall survival of patients who underwent nivolumab/ipilimumab treatment or nivolumab/ipilimumab+CBM588 LBP treatment. Overall survival time was measured in weeks.

For patients enrolled the trial, a significant number of patients administered nivolumab/ipilimumab in combination with CBM588 advanced with progression free survival as compared to patients administered nivolumab/ipilimumab without CBM588 (FIG. 5). Similarly, overall survival increased in patients administered the combination therapy of checkpoint inhibitors with CBM588 compared to patients who took checkpoint inhibitors without CBM588 (FIG. 6).

TABLE 6

| Progression free survival. | | | | | | | | |
|---|---|---|---|---|---|---|---|---|
| | Mean[a] | | | | Median | | | |
| | | | 95% Confidence Interval | | | | 95% Confidence Interval | |
| NI1NIC2 | Estimate | Std. Error | Lower Bound | Upper Bound | Estimate | Std. Error | Lower Bound | Upper Bound |
| 1.00 | 15.625 | 3.095 | 9.558 | 21.692 | 11.000 | 1.810 | 7.452 | 14.548 |
| 2.00 | 62.746 | 9.183 | 44.748 | 80.744 | . | . | . | . |
| Overall | 47.167 | 7.588 | 32.296 | 62.039 | 23.860 | 11.074 | 2.155 | 45.565 |

[a]Estimation is limited to the largest survival time if it is censored.

TABLE 7

Progression free Survival: Test of equality of survival distributions for different levels of NI1NIC2.
Overall Comparisons

| | Chi-Square | df | Sig. |
|---|---|---|---|
| Log Rank (Mantel-Cox) | 11.159 | 1 | .001 |

TABLE 8

| Overall Survival. | | | | | | | | |
|---|---|---|---|---|---|---|---|---|
| | Mean[a] | | | | Median | | | |
| | | | 95% Confidence Interval | | | | 95% Confidence Interval | |
| NI1NIC2 | Estimate | Std. Error | Lower Bound | Upper Bound | Estimate | Std. Error | Lower Bound | Upper Bound |
| 1.00 | 71.088 | 11.906 | 47.751 | 94.424 | . | . | . | . |
| 2.00 | 88.456 | 5.687 | 77.309 | 99.602 | . | . | . | . |
| Overall | 82.567 | 5.832 | 71.136 | 93.998 | . | . | . | . |

[a]Estimation is limited to the largest survival time if it is censored.

TABLE 9

Overall survival: Test of equality of survival distributions for different levels of NI1NIC2.
Overall Comparisons

| | Chi-Square | df | Sig. |
|---|---|---|---|
| Log Rank (Mantel-Cox) | 2.007 | 1 | .157 |

Figure 7:
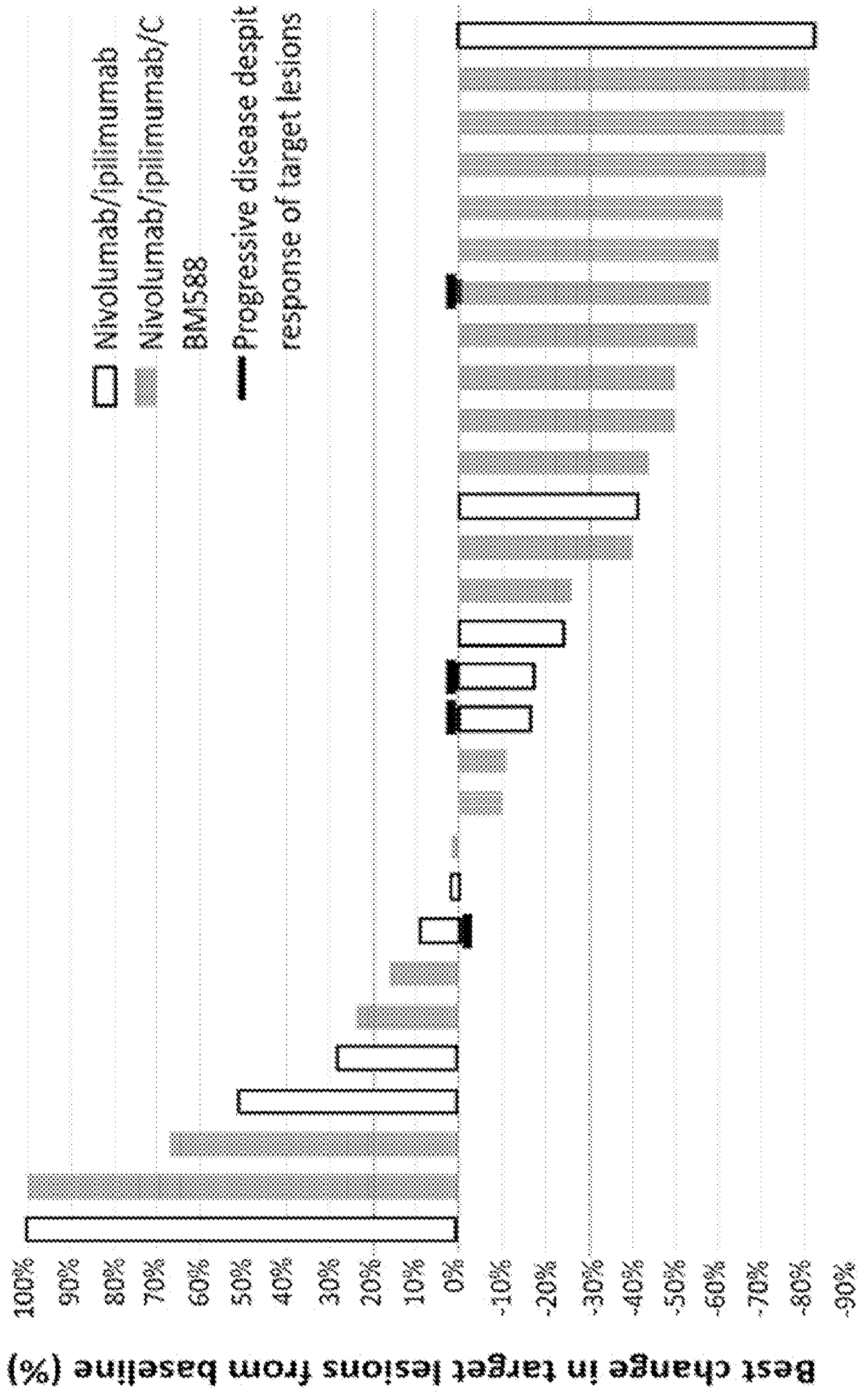
FIG. 7 is a graph illustrating the change in target lesions in patients who underwent nivolumab/ipilimumab treatment or nivolumab/ipilimumab+CBM588 LBP treatment.

Further, more patients receiving the combination nivolumab/ipilimumab/CBM588 therapy showed responsiveness to the therapy, as measured by changes in cancerous lesions (FIG. 7 and Table 10). Similarly, the overall response was higher in patients receiving the combination therapy including CBM588, as compared to patients receiving the checkpoint inhibitors by themselves (Table 11).

TABLE 10

Responsiveness of target lesions in patients receiving Nivo/Ipi or Nivo/Ipi/CBM.

| Response in target lesions | All (n = 29) | Arm 1 - Nivo/Ipi (n = 10) | Arm 2- Nivo/Ipi/CBM (n = 19) |
|---|---|---|---|
| Complete response | 0 | 0 | 0 |
| Partial response | 13 | 2 | 11 |
| Stable disease | 10 | 5 | 5 |
| Progressive disease | 6 | 3 | 3 |

TABLE 11

Overall response of patients receiving Nivo/Ipi or Nivo/Ipi/CBM.

| Overall response | All (n = 29) | Arm 1 - Nivo/Ipi (n = 10) | Arm 2 - Nivo/Ipi/CBM (n = 19) | P value |
|---|---|---|---|---|
| ORR | 12(41%) | 2 (20%) | 10 (53%) | 0.096 |
| CR | 0 | 0 | 0 | |
| PR | 12 | 2 | 10 | |

TABLE 11-continued

Overall response of patients receiving Nivo/Ipi or Nivo/Ipi/CBM.

| Overall response | All (n = 29) | Arm 1 - Nivo/Ipi (n = 10) | Arm 2 - Nivo/Ipi/CBM (n = 19) | P value |
|---|---|---|---|---|
| SD | 6 | 2 | 5 | |
| PD | 9 | 6 | 4 | |

Figure 8:
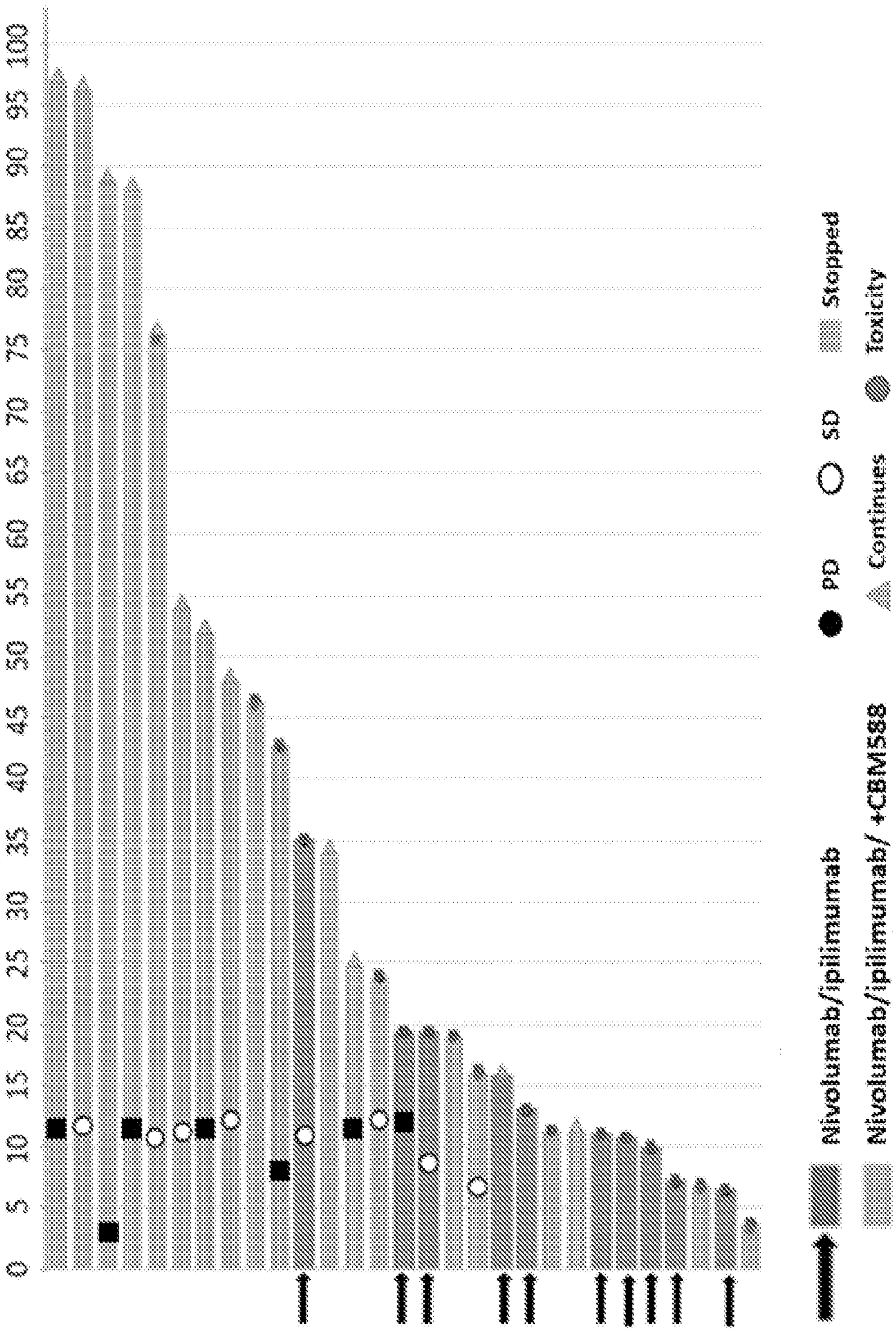
FIG. 8 illustrates responsiveness and disease progression of patients undergoing nivolumab/ipilimumab or nivolumab/ipilimumab+CBM588 LBP treatment.
Figure 9A:
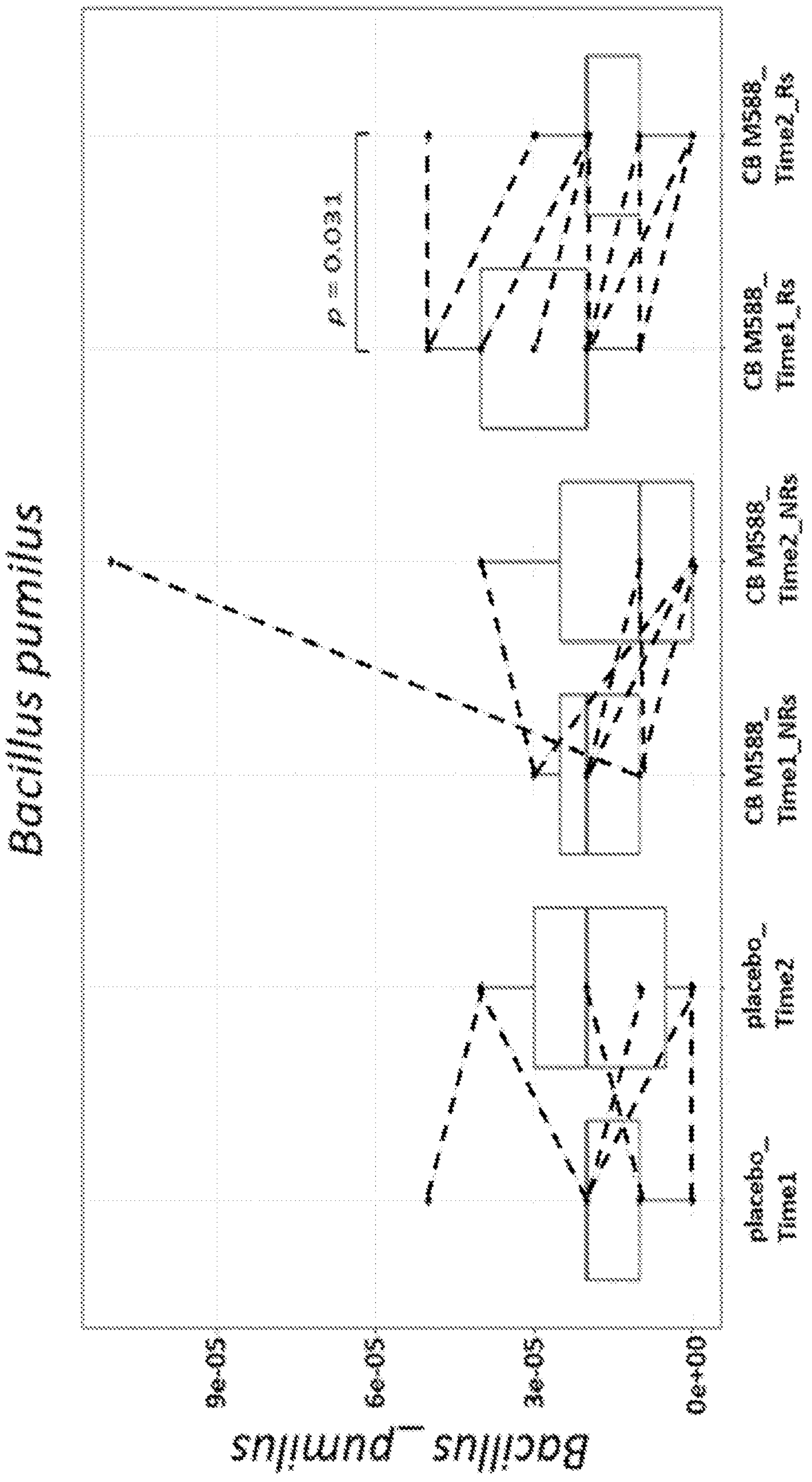
FIGS. 9A and 9B are graphs showing relative abundance of bacterial species *Bacillus pumilus* (FIG. 9A) and *Bacillus* velezensis (FIG. 9B) in patients who were responsive (Rs) to CBM588 treatment as compared to patients who were non-responsive (NRs) to CBM588 treatment at Time 1 and Time 2.
Figure 9B:
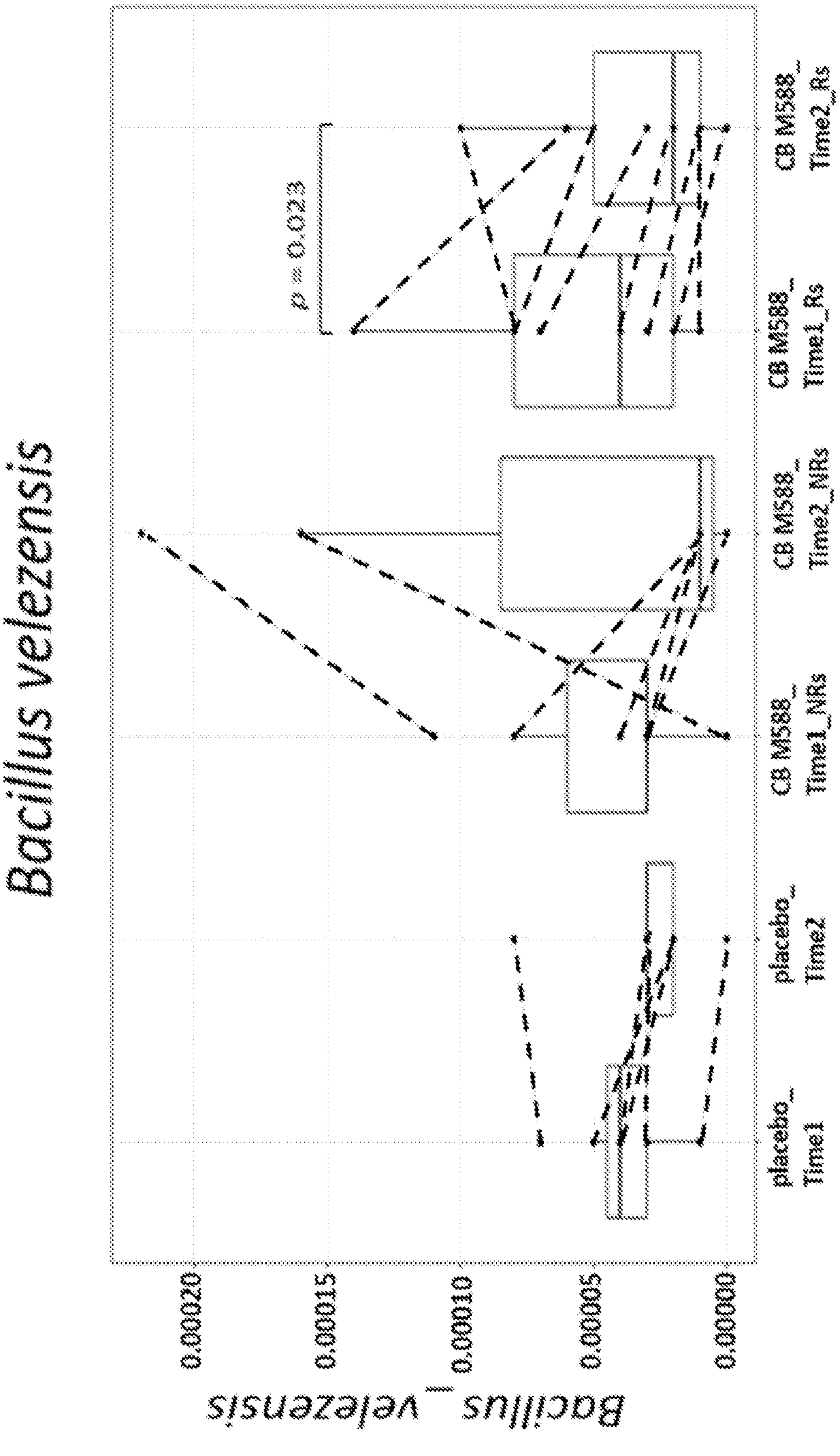
Figure 10A:
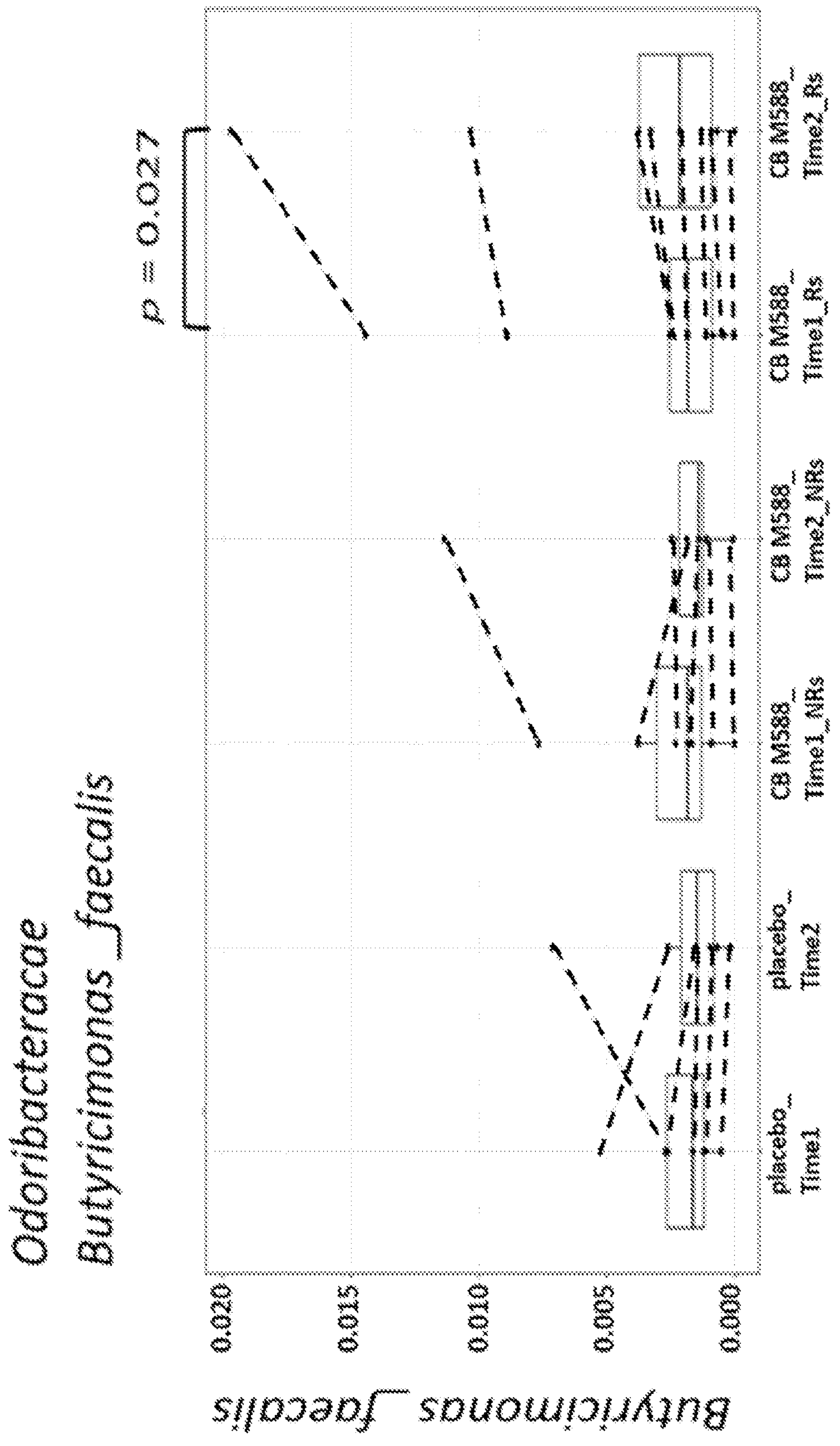
Figure 10B:
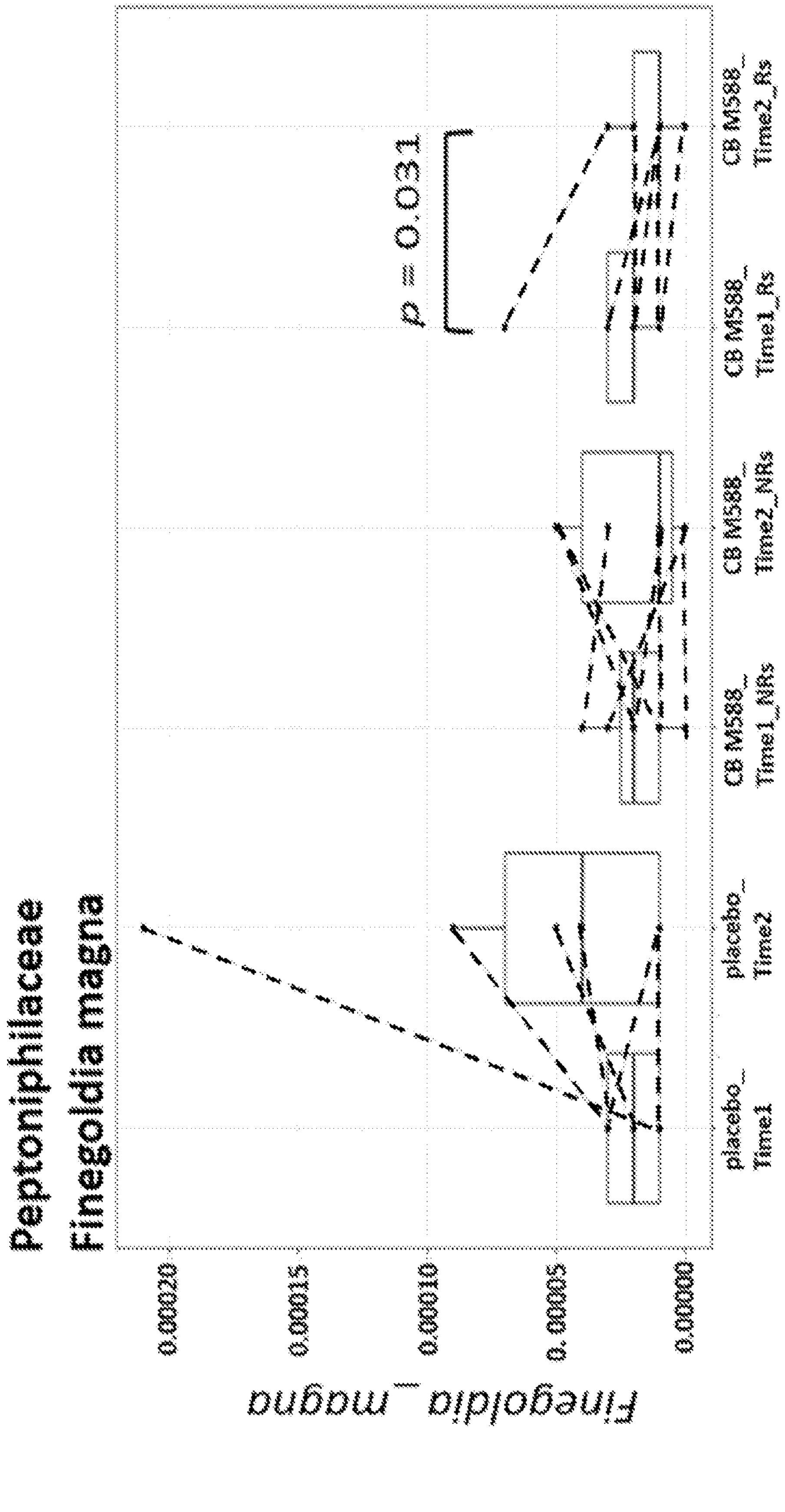
Figure 10C:
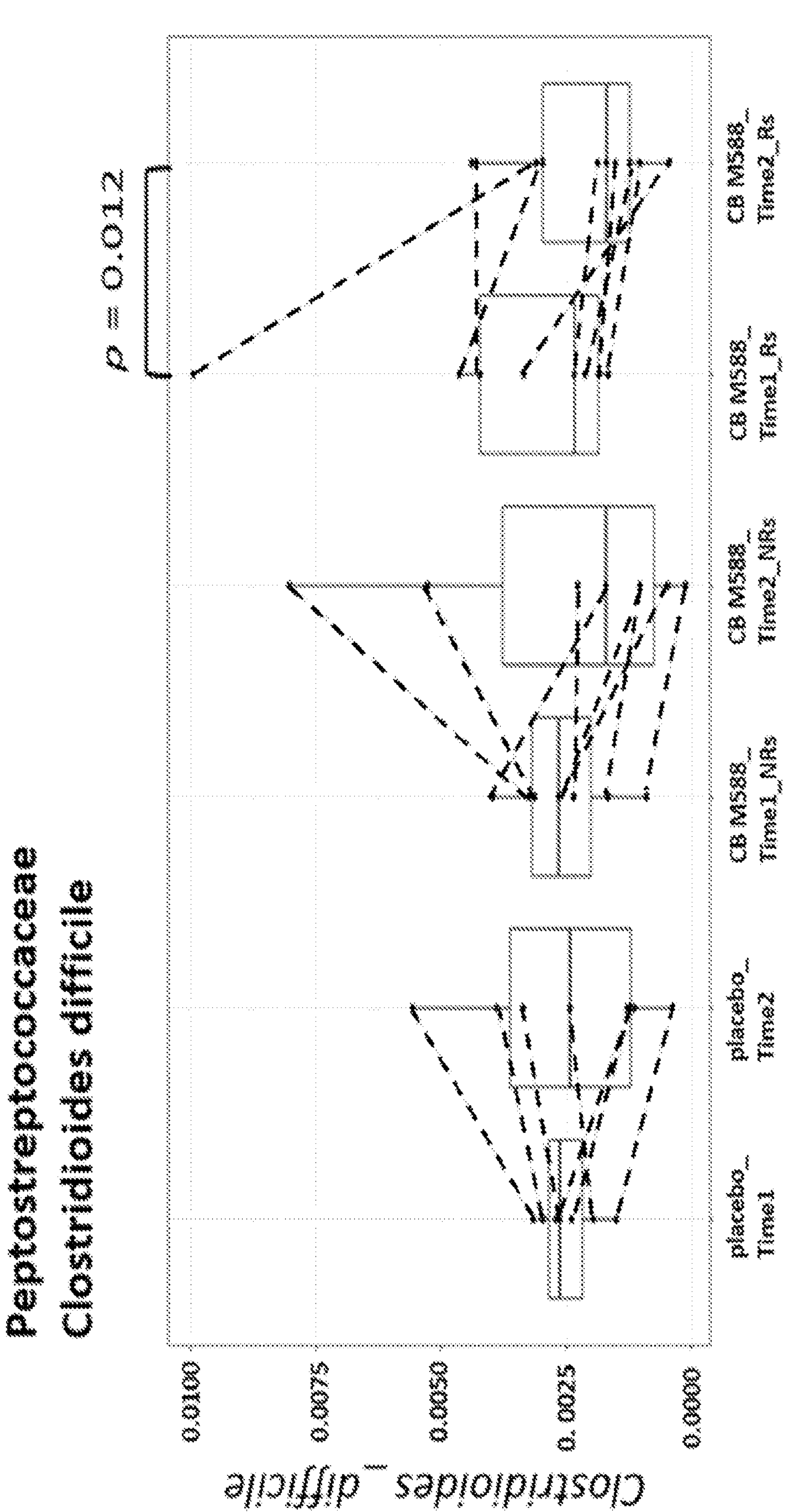
Figure 10D:
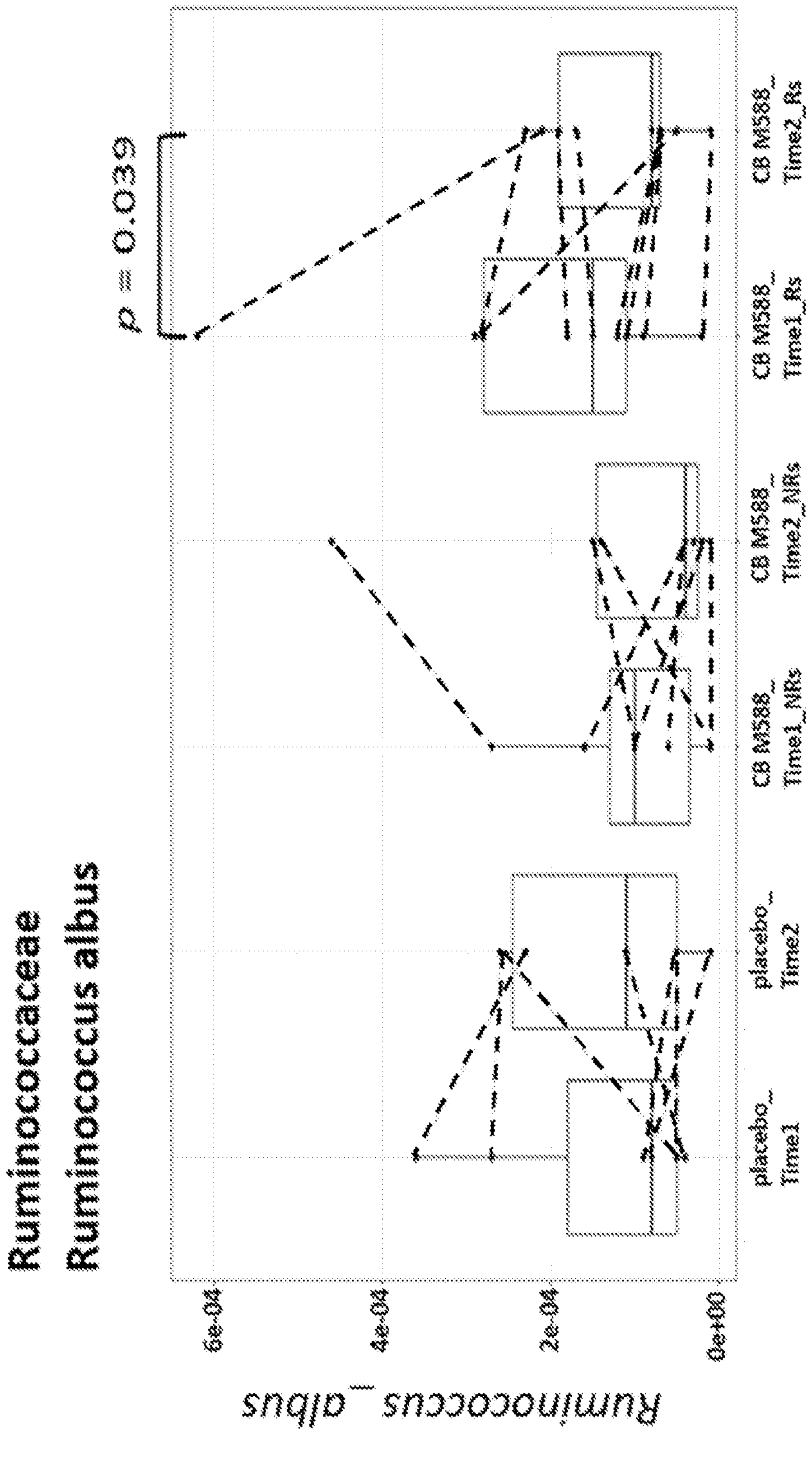
Figure 10E:
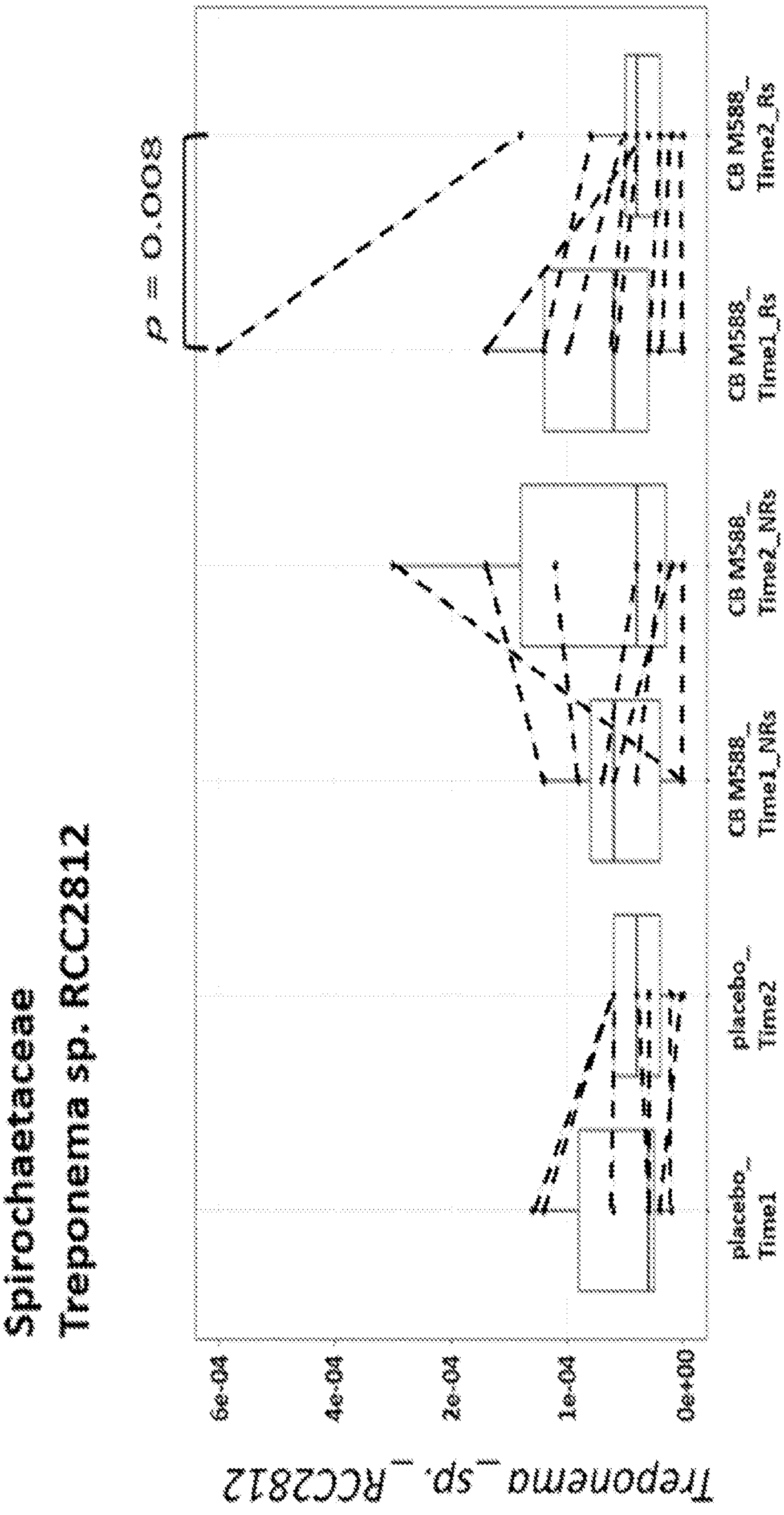
Figure 10F:
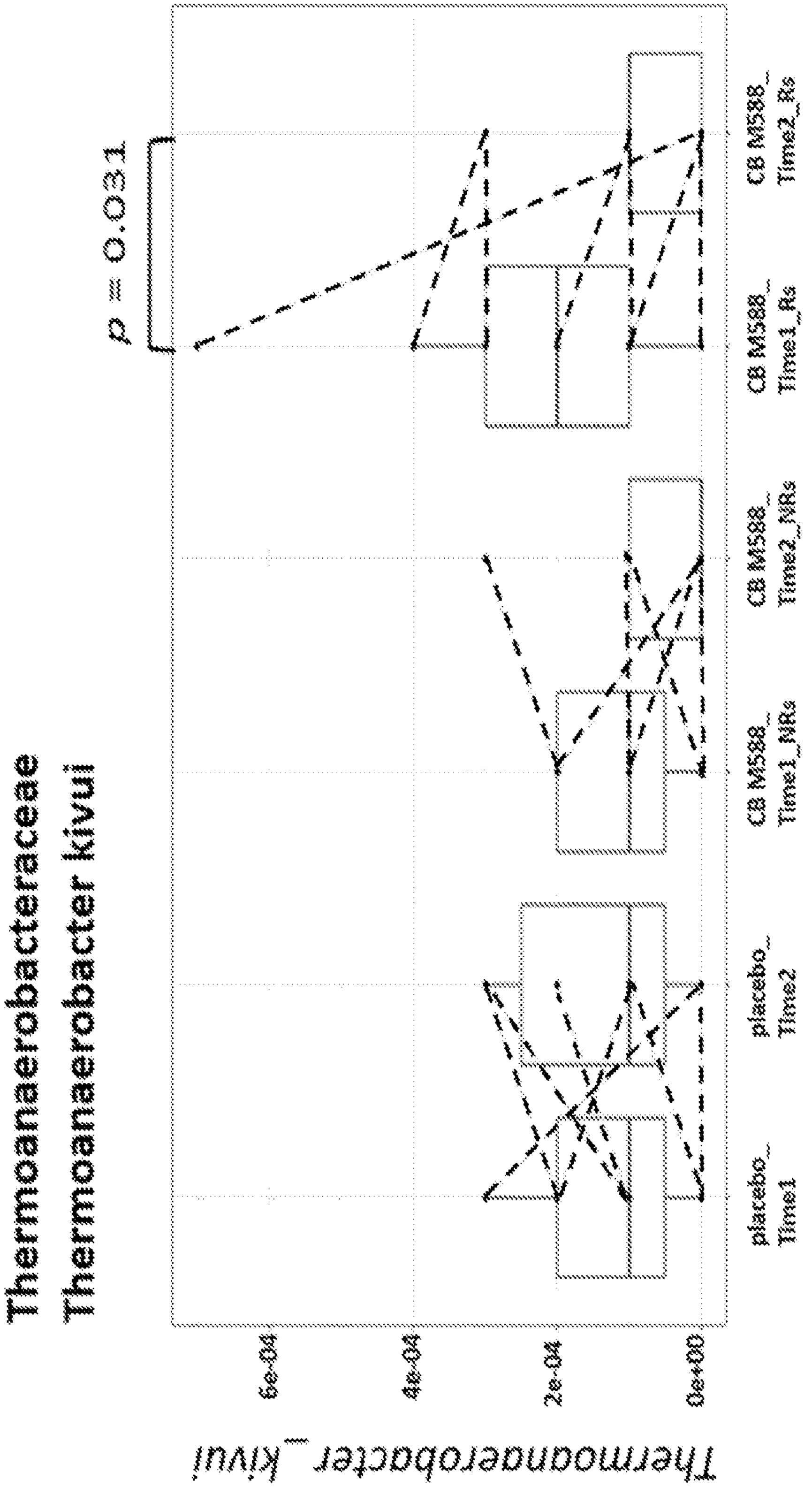

Results from the study further show that more patients are able to continue treatment when administered the combination therapy including CBM588, compared to patients who received only the checkpoint inhibitor treatment. Moreover, more patients that received the combination therapy showed either stable disease or partial response to the treatment (FIG. 8).

Example 3: Analysis of Gastrointestinal Tract Modulation by CBM588

Without wishing to be bound by scientific theory, Applicants' rationale for the clinical study described herein was that CBM588 can modify the GI microbiome to enhance host immune function against cancer. The precise bacterial populations within the GI tract that can enhance or dampen host immune function are not well understood. Thus, Wilcoxon signed rank test was performed to compare the relative abundance at species level only between Time1 and Time2 data of the CBM588 Responder group. Significant differences in relative abundances of 44 species were detected and their relative abundances in each group were shown as a boxplot (multiplicity adjustment not considered) (FIGS. 9A-9B, 10A-10F, 11A-11C, 12A-12C and 13A).

One possible group of bacteria within the GI tract associated with improved response to immune checkpoint therapy against cancer is *Bifidobacterium*. The microbiome data indeed show a trend towards increase in *Bifidobacterium* within the GI tract before (T1) to after (T2) CBM588 treatment. This effect was not observed in placebo subjects. In addition, there are increases and decreases in other bacterial populations specifically in CBM588 treated subjects that may underlie the immune benefits against cancer (FIGS. 9A-9B, 10A-10F, 11A-11C, 12A-12C and 13A).

REFERENCES

1. Surveillance, Epidemiology, and End Results Program. SEER stat fact sheets: kidney and renal pelvis cancer. Bethesda, MD, National Cancer Institute
2. Choueiri T K, Motzer R J: Systemic Therapy for Metastatic Renal-Cell Carcinoma. N Engl J Med 376:354-366, 2017
3. Motzer R J, Tannir N M, McDermott D F, et al: Nivolumab plus Ipilimumab versus Sunitinib in Advanced Renal-Cell Carcinoma. N Engl J Med 378: 1277-1290, 2018
4. Motzer R J, Tannir N M, McDermott D F, et al: Nivolumab plus Ipilimumab versus Sunitinib in Advanced Renal-Cell Carcinoma. New England Journal of Medicine 378:1277-1290, 2018
5. Vetizou M, Pitt J M, Daillere R, et al: Anticancer immunotherapy by CTLA-4 blockade relies on the gut microbiota. Science 350:1079-84, 2015
6. Sivan A, Corrales L, Hubert N, et al: Commensal *Bifidobacterium* promotes antitumor immunity and facilitates anti-PD-L1 efficacy. Science 350:1084-9, 2015
7. Gopalakrishnan V, Spencer C N, Nezi L, et al: Gut microbiome modulates response to anti-PD-1 immunotherapy in melanoma patients. Science 359:97-103, 2018
8. Derosa L, Hellmann M D, Spaziano M, et al: Negative association of antibiotics on clinical activity of immune checkpoint inhibitors in patients with advanced renal cell and non-small-cell lung cancer. Ann Oncol 29:1437-1444, 2018
9. Isa K, Oka K, Beauchamp N, et al: Safety assessment of the *Clostridium butyricum* MIYAIRI 588(R) probiotic strain including evaluation of antimicrobial sensitivity and presence of *Clostridium* toxin genes in vitro and teratogenicity in vivo. Hum Exp Toxicol 35:818-32, 2016
10. Seki H, Shiohara M, Matsumura T, et al: Prevention of antibiotic-associated diarrhea in children by *Clostridium butyricum* MIYAIRI. Pediatr Int 45:86-90, 2003
11. Yasueda A, Mizushima T, Nezu R, et al: The effect of *Clostridium butyricum* MIYAIRI on the prevention of pouchitis and alteration of the microbiota profile in patients with ulcerative colitis. Surg Today 46:939-49, 2016
12. Sato S, Nagai H, Igarashi Y: Effect of probiotics on serum bile acids in patients with ulcerative colitis. Hepatogastroenterology 59:1804-8, 2012
13. Chalmin F, Ladoire S, Mignot G, et al: Membrane-associated Hsp72 from tumor-derived exosomes mediates STATS-dependent immunosuppressive function of mouse and human myeloid-derived suppressor cells. J Clin Invest 120:457-71, 2010
14. Eisenhauer E A, Therasse P, Bogaerts J, et al: New response evaluation criteria in solid tumours: revised RECIST guideline (version 1.1). Eur J Cancer 45:228-47, 2009
15. Oken M M, Creech R H, Tormey D C, et al: Toxicity and response criteria of the Eastern Cooperative Oncology Group. Am J Clin Oncol 5:649-55, 1982

What is claimed is:

1. A method for treating cancer in a subject in need thereof, said method comprising administering to said subject a therapeutically effective amount of an anti-cancer agent and a *Clostridium butyricum* live biotherapeutic product but without another live biotherapeutic product.

2. The method of claim 1, wherein said *Clostridium butyricum* live biotherapeutic product is *Clostridium butyricum* MIYAIRI 588 live biotherapeutic product (CBM588 LBP).

3. The method of claim 1, wherein the anti-cancer agent is a checkpoint inhibitor.

4. The method of claim 3, wherein the checkpoint inhibitor is a PD-1, PD-L1 or CTLA-4 inhibitor.

5. The method of claim 3, wherein said checkpoint inhibitor is nivolumab, ipilimumab, pembrolizumab, cemiplimab, durvalumab, daclizumab, avelumab, or atezolizumab.

6. The method of claim 1, further comprising administering a second anticancer agent.

7. The method of claim 6, wherein said second anti-cancer agent is a second checkpoint inhibitor.

8. The method of claim 1, wherein said cancer is a microsatellite-instability high (MSI-H) cancer.

9. The method of claim 1, wherein said cancer is metastatic renal cell carcinoma (mRCC), non-small cell lung cancer, melanoma, sarcoma, lymphoma, breast cancer, bladder cancer, cervical cancer, colon cancer, head and neck cancer, liver cancer, stomach cancer, or rectal cancer.

10. The method of claim 1, comprising administering said anti-cancer agent in a first dosage form and said *Clostridium butyricum* live biotherapeutic product in a second dosage form.

11. The method of claim 10, wherein said anti-cancer agent is at a dosage below its therapeutically effective amount when used in the absence of said *Clostridium butyricum* live biotherapeutic product for treating cancer.

12. The method of claim 1, comprising administering to said subject a therapeutically effective amount of (1) a PD-1 inhibitor or a PD-L1 inhibitor; (2) a CTLA-4 inhibitor; and (3) a *Clostridium butyricum* live biotherapeutic product.

13. The method of claim 12, comprising administering to said subject a therapeutically effective amount of (1) nivolumab; (2) ipilimumab; and (3) a *Clostridium butyricum* live biotherapeutic product.

14. The method of claim 13, wherein said *Clostridium butyricum* live biotherapeutic product is *Clostridium butyricum* MIYAIRI 588 live biotherapeutic product (CBM588 LBP).

15. The method of claim 14, wherein said cancer is metastatic renal cell carcinoma (mRCC).

* * * * *

SEQUENCE LISTING

```
<160> NUMBER OF SEQ ID NOS: 4

<210> SEQ ID NO 1
<211> LENGTH: 52
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (42)..(42)
<223> OTHER INFORMATION: m is a or c

<400> SEQUENCE: 1

acactctttc cctacacgac gctcttccga tctgtgccag cmgccgcggt aa            52


<210> SEQ ID NO 2
<211> LENGTH: 52
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (42)..(42)
<223> OTHER INFORMATION: m is a or c

<400> SEQUENCE: 2
```

-continued

```
acactctttc cctacacgac gctcttccga tctgtgccag cmgccgcggt aa            52


<210> SEQ ID NO 3
<211> LENGTH: 51
<212> TYPE: DNA
<213> ORGANISM: Artificial Sequence
<220> FEATURE:
<223> OTHER INFORMATION: Synthetic polynucleotide

<400> SEQUENCE: 3

acactctttc cctacacgac gctcttccga tctgattaga taccctggta g             51


<210> SEQ ID NO 4
<211> LENGTH: 54
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (45)..(45)
<223> OTHER INFORMATION: m is a or c

<400> SEQUENCE: 4

gtgactggag ttcagacgtg tgctcttccg atctccgtca attcmtttga gttt          54
```